US011206005B2

(12) United States Patent
Luo

(10) Patent No.: US 11,206,005 B2
(45) Date of Patent: Dec. 21, 2021

(54) COMPOSITIONS OF INFLUENZA HEMAGGLUTININ WITH HETEROLOGOUS EPITOPES AND/OR ALTERED MATURATION CLEAVAGE SITES AND METHODS OF USE THEREOF

(71) Applicant: CG Discovery, Inc., San Diego, CA (US)

(72) Inventor: Chun Luo, San Diego, CA (US)

(73) Assignee: CG Discovery, Inc., San Diego, CA (US)

(*) Notice: Subject to any disclaimer, the term of this patent is extended or adjusted under 35 U.S.C. 154(b) by 0 days.

(21) Appl. No.: 16/410,998

(22) Filed: May 13, 2019

(65) Prior Publication Data
US 2019/0341901 A1 Nov. 7, 2019

Related U.S. Application Data

(63) Continuation of application No. 15/556,555, filed as application No. PCT/US2017/016251 on Feb. 2, 2017, now Pat. No. 10,291,197.

(60) Provisional application No. 62/290,894, filed on Feb. 3, 2016.

(51) Int. Cl.
*A61K 39/145* (2006.01)
*C07K 14/11* (2006.01)
*H03H 7/01* (2006.01)
*H01L 23/50* (2006.01)
*H01L 23/522* (2006.01)
*H01L 23/66* (2006.01)
*A61K 39/12* (2006.01)
*H03F 1/02* (2006.01)
*H03F 1/56* (2006.01)
*H03F 3/193* (2006.01)
*H03F 3/195* (2006.01)
*C07K 14/005* (2006.01)
*H04B 1/40* (2015.01)
*A61K 39/00* (2006.01)

(52) U.S. Cl.
CPC ........... *H03H 7/0115* (2013.01); *A61K 39/12* (2013.01); *C07K 14/005* (2013.01); *H01L 23/50* (2013.01); *H01L 23/5223* (2013.01); *H01L 23/5227* (2013.01); *H01L 23/66* (2013.01); *H03F 1/0222* (2013.01); *H03F 1/565* (2013.01); *H03F 3/193* (2013.01); *H03F 3/195* (2013.01); *H04B 1/40* (2013.01); *A61K 2039/5256* (2013.01); *C07K 2319/40* (2013.01); *C07K 2319/50* (2013.01); *C12N 2760/16121* (2013.01); *C12N 2760/16122* (2013.01); *C12N 2760/16134* (2013.01); *C12N 2760/16222* (2013.01); *H03F 2200/294* (2013.01); *H03F 2200/408* (2013.01); *H03F 2200/451* (2013.01)

(58) Field of Classification Search
None
See application file for complete search history.

(56) References Cited

U.S. PATENT DOCUMENTS

| 5,591,823 A | 1/1997 | Hung et al. |
| 2004/0234552 A1 | 11/2004 | Peeters et al. |
| 2011/0177117 A1 | 7/2011 | Blais et al. |

FOREIGN PATENT DOCUMENTS

| RU | 2011 105 885 | 8/2012 |
| WO | WO-2004/034956 | 4/2004 |
| WO | WO-2010/006452 | 1/2010 |
| WO | WO-2015/020913 | 2/2015 |
| WO | WO-2016/205347 | 12/2016 |

OTHER PUBLICATIONS

Yan et al. An epitope on the stem region of hemagglutinin of H1N1 influenza A virus recognized by neutralizing monoclonal antibody. Biochemical and Biophysical Research Communications 518 (2019) 319-324.*
Wang et al. Vaccination with a synthetic peptide from the influenza virus hemagglutinin provides protection against distinct viral subtypes. P.N.A.S., 2010, 107: 18979-18984.*
Biao et al., "An Influenza DNA Vaccine Based on a Fusion Gene of HA Stalk and M2e Domains," Life Science Research (2013) 17(4):325-330.
Callan et al., "Cleavage of Influenza A Virus H1 Hemagglutinin by Swine Respiratory Bacterial Proteases," J. Virol. (1997) 71:7579-7585.
International Search Report and Written Opinion for PCT/US17/16251, dated Apr. 21, 2017, 16 pages.
Lu et al., "Reassortment and Modification of Hemagglutinin Cleavage Motif of Avian/WSN Influenza Viruses Generated by Reverse Genetics That Correlate With Attenuation," Acta virologica (2006) 50:243-249.
Lu et al., "Production and stabilization of the trimeric influenza hemagglutinin stem domain for potentially broadly protective influenza vaccines," PNAS (2013) 6 pages.
Ravin et al., "Development of a Candidate Influenza Vaccine Based on Virus-like Particles Displaying Influenza M2e Peptide into the Immunodominant Loop Region of Hepatitis B Core Antigen: Insertion of Multiple Copies of M2e Increases Immunogenicity and Protective Efficiency," Vaccine (2015) 33(29):3392-3397.
Stech et al., "A new approach to an influenza live vaccine: modification of the cleavage site of hemagglutinin," Nature Medicine (2005) 11:683-689.
Stevens et al., "Structure and Receptor Specificity of the Hemagglutinin from an H5N1 Influenza Virus," Science (2006) 312:404-410.

(Continued)

Primary Examiner — Nianxiang Zou
(74) Attorney, Agent, or Firm — Morrison & Foerster LLP

(57) ABSTRACT

Modified forms of hemagglutinin (HA) protein including those with modified immunodominant regions and with modified maturation cleavage sites, and virus and virus-like particles containing them are disclosed.

14 Claims, 10 Drawing Sheets
Specification includes a Sequence Listing.

(56) References Cited

OTHER PUBLICATIONS

Supplementary European Search Report for EP 17748171.0, dated Oct. 31, 2019, 13 pages.
Klausberger et al., "Globular Head-Displayed Conserved Influenza H1 Hemagglutinin Stalk Epitopes Confer Protection against Heterologous H1 N1 Virus," PLOS ONE (2016) 21 pages.

\* cited by examiner

SEQUENCE LISTING

```
<160> NUMBER OF SEQ ID NOS: 65

<210> SEQ ID NO 1
<211> LENGTH: 566
<212> TYPE: PRT
<213> ORGANISM: Influenza A virus

<400> SEQUENCE: 1

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
```

```
            100                 105                110
Ile Asp Tyr Glu Glu Leu Arg Glu Gln Leu Ser Ser Val Ser Ser Phe
            115                 120                125

Glu Arg Phe Glu Ile Phe Pro Lys Thr Ser Ser Trp Pro Asn His Asp
            130                 135                140

Ser Asn Lys Gly Val Thr Ala Ala Cys Pro His Ala Gly Ala Lys Ser
145                     150                 155                160

Phe Tyr Lys Asn Leu Ile Trp Leu Val Lys Lys Gly Asn Ser Tyr Pro
            165                 170                175

Lys Leu Ser Lys Ser Tyr Ile Asn Asp Lys Gly Lys Glu Val Leu Val
            180                 185                190

Leu Trp Gly Ile His His Pro Ser Thr Ser Ala Asp Gln Gln Ser Leu
            195                 200                205

Tyr Gln Asn Ala Asp Ala Tyr Val Phe Val Gly Ser Ser Arg Tyr Ser
            210                 215                220

Lys Lys Phe Lys Pro Glu Ile Ala Ile Arg Pro Lys Val Arg Asp Gln
225                     230                 235                240

Glu Gly Arg Met Asn Tyr Tyr Trp Thr Leu Val Glu Pro Gly Asp Lys
                245                 250                255

Ile Thr Phe Glu Ala Thr Gly Asn Leu Val Val Pro Arg Tyr Ala Phe
                260                 265                270

Ala Met Glu Arg Asn Ala Gly Ser Gly Ile Ile Ile Ser Asp Thr Pro
                275                 280                285

Val His Asp Cys Asn Thr Thr Cys Gln Thr Pro Lys Gly Ala Ile Asn
                290                 295                300

Thr Ser Leu Pro Phe Gln Asn Ile His Pro Ile Thr Ile Gly Lys Cys
305                     310                 315                320

Pro Lys Tyr Val Lys Ser Thr Lys Leu Arg Leu Ala Thr Gly Leu Arg
                325                 330                335

Asn Ile Pro Ser Ile Gln Ser Arg Gly Leu Phe Gly Ala Ile Ala Gly
                340                 345                350

Phe Ile Glu Gly Gly Trp Thr Gly Met Val Asp Gly Trp Tyr Gly Tyr
                355                 360                365

His His Gln Asn Glu Gln Gly Ser Gly Tyr Ala Ala Asp Leu Lys Ser
                370                 375                380

Thr Gln Asn Ala Ile Asp Glu Ile Thr Asn Lys Val Asn Ser Val Ile
385                     390                 395                400

Glu Lys Met Asn Thr Gln Phe Thr Ala Val Gly Lys Glu Phe Asn His
                405                 410                415

Leu Glu Lys Arg Ile Glu Asn Leu Asn Lys Lys Val Asp Asp Gly Phe
                420                 425                430

Leu Asp Ile Trp Thr Tyr Asn Ala Glu Leu Leu Val Leu Leu Glu Asn
                435                 440                445

Glu Arg Thr Leu Asp Tyr His Asp Ser Asn Val Lys Asn Leu Tyr Glu
                450                 455                460

Lys Val Arg Ser Gln Leu Lys Asn Asn Ala Lys Glu Ile Gly Asn Gly
465                     470                 475                480

Cys Phe Glu Phe Tyr His Lys Cys Asp Asn Thr Cys Met Glu Ser Val
                485                 490                495

Lys Asn Gly Thr Tyr Asp Tyr Pro Lys Tyr Ser Glu Glu Ala Lys Leu
                500                 505                510

Asn Arg Glu Glu Ile Asp Gly Val Lys Leu Glu Ser Thr Arg Ile Tyr
                515                 520                525
```

```
Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 2
<211> LENGTH: 20
<212> TYPE: PRT
<213> ORGANISM: Artificial Sequence
<220> FEATURE:
<223> OTHER INFORMATION: Synthetic

<400> SEQUENCE: 2

Met Val Ser Ala Ile Val Leu Tyr Val Leu Leu Ala Ala Ala Ala His
1               5                  10                  15

Ser Ala Phe Ala
            20

<210> SEQ ID NO 3
<211> LENGTH: 49
<212> TYPE: PRT
<213> ORGANISM: Artificial Sequence
<220> FEATURE:
<223> OTHER INFORMATION: Synthetic

<400> SEQUENCE: 3

Gly Ala Glu Asn Leu Tyr Phe Gln Gly Gly Ser Gly Tyr Ile Pro Glu
1               5                  10                  15

Ala Pro Arg Asp Gly Gln Ala Tyr Val Arg Lys Asp Gly Glu Trp Val
            20                  25                  30

Leu Leu Ser Thr Phe Leu Gly His His His His His His His His
        35                  40                  45

His

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Glu Asn Leu Tyr Phe Gln Gly
1               5

<210> SEQ ID NO 5
<211> LENGTH: 29
<212> TYPE: PRT
<213> ORGANISM: Artificial Sequence
<220> FEATURE:
<223> OTHER INFORMATION: Synthetic

<400> SEQUENCE: 5

Gly Ser Gly Tyr Ile Pro Glu Ala Pro Arg Asp Gly Gln Ala Tyr Val
1               5                  10                  15

Arg Lys Asp Gly Glu Trp Val Leu Leu Ser Thr Phe Leu
            20                  25

<210> SEQ ID NO 6
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 6

His His His His His His His His His
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Synthetic

<400> SEQUENCE: 7

Met Lys Ala Ile Leu Val Val Leu Leu Tyr Thr Phe Ala Thr Ala Asn
1               5                   10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Ile Pro Ser Ile Gln Ser Arg
1               5

<210> SEQ ID NO 9
<211> LENGTH: 581
<212> TYPE: PRT
<213> ORGANISM: Artificial Sequence
<220> FEATURE:
<223> OTHER INFORMATION: Synthetic

<400> SEQUENCE: 9

Met Val Ser Ala Ile Val Leu Tyr Val Leu Leu Ala Ala Ala Ala His
1               5                   10                  15

Ser Ala Phe Ala Asp Thr Leu Cys Ile Gly Tyr His Ala Asn Asn Ser
                20                  25                  30

Thr Asp Thr Val Asp Thr Val Leu Glu Lys Asn Val Thr Val Thr His
            35                  40                  45

Ser Val Asn Leu Leu Glu Asp Lys His Asn Gly Lys Leu Cys Lys Leu
        50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
                100                 105                 110

Gly Asp Phe Ile Asp Tyr Glu Glu Leu Arg Glu Gln Leu Ser Ser Val
            115                 120                 125

Ser Ser Phe Glu Arg Phe Glu Ile Phe Pro Lys Thr Ser Ser Trp Pro
        130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
```

```
                165                 170                 175
Ser Tyr Pro Lys Leu Ser Lys Ser Tyr Ile Asn Asp Lys Gly Lys Glu
            180                 185                 190

Val Leu Val Leu Trp Gly Ile His His Pro Ser Thr Ser Ala Asp Gln
            195                 200                 205

Gln Ser Leu Tyr Gln Asn Ala Asp Ala Tyr Val Phe Val Gly Ser Ser
            210                 215                 220

Arg Tyr Ser Lys Lys Phe Lys Pro Glu Ile Ala Ile Arg Pro Lys Val
225                 230                 235                 240

Arg Asp Gln Glu Gly Arg Met Asn Tyr Tyr Trp Thr Leu Val Glu Pro
                245                 250                 255

Gly Asp Lys Ile Thr Phe Glu Ala Thr Gly Asn Leu Val Val Pro Arg
                260                 265                 270

Tyr Ala Phe Ala Met Glu Arg Asn Ala Gly Ser Gly Ile Ile Ile Ser
                275                 280                 285

Asp Thr Pro Val His Asp Cys Asn Thr Cys Gln Thr Pro Lys Gly
                290                 295                 300

Ala Ile Asn Thr Ser Leu Pro Phe Gln Asn Ile His Pro Ile Thr Ile
305                 310                 315                 320

Gly Lys Cys Pro Lys Tyr Val Lys Ser Thr Lys Leu Arg Leu Ala Thr
                325                 330                 335

Gly Leu Arg Asn Ile Pro Ser Ile Gln Ser Arg Gly Leu Phe Gly Ala
                340                 345                 350

Ile Ala Gly Phe Ile Glu Gly Gly Trp Thr Gly Met Val Asp Gly Trp
                355                 360                 365

Tyr Gly Tyr His His Gln Asn Glu Gln Gly Ser Gly Tyr Ala Ala Asp
                370                 375                 380

Leu Lys Ser Thr Gln Asn Ala Ile Asp Glu Ile Thr Asn Lys Val Asn
385                 390                 395                 400

Ser Val Ile Glu Lys Met Asn Thr Gln Phe Thr Ala Val Gly Lys Glu
                405                 410                 415

Phe Asn His Leu Glu Lys Arg Ile Glu Asn Leu Asn Lys Lys Val Asp
                420                 425                 430

Asp Gly Phe Leu Asp Ile Trp Thr Tyr Asn Ala Glu Leu Leu Val Leu
                435                 440                 445

Leu Glu Asn Glu Arg Thr Leu Asp Tyr His Asp Ser Asn Val Lys Asn
450                 455                 460

Leu Tyr Glu Lys Val Arg Ser Gln Leu Lys Asn Asn Ala Lys Glu Ile
465                 470                 475                 480

Gly Asn Gly Cys Phe Glu Phe Tyr His Lys Cys Asp Asn Thr Cys Met
                485                 490                 495

Glu Ser Val Lys Asn Gly Thr Tyr Asp Tyr Pro Lys Tyr Ser Glu Glu
                500                 505                 510

Ala Lys Leu Asn Arg Glu Glu Ile Asp Gly Val Lys Leu Glu Ser Thr
                515                 520                 525

Arg Ile Tyr Gln Gly Ala Glu Asn Leu Tyr Phe Gln Gly Gly Ser Gly
                530                 535                 540

Tyr Ile Pro Glu Ala Pro Arg Asp Gly Gln Ala Tyr Val Arg Lys Asp
545                 550                 555                 560

Gly Glu Trp Val Leu Leu Ser Thr Phe Leu Gly His His His His
                565                 570                 575

His His His His His
                580
```

<210> SEQ ID NO 10
<211> LENGTH: 1757
<212> TYPE: DNA
<213> ORGANISM: Artificial Sequence
<220> FEATURE:
<223> OTHER INFORMATION: Synthetic

<400> SEQUENCE: 10

| | |
|---|---|
| ccatggtaag cgctattgtt ttatatgtgc ttttggcggc ggcggcgcat tctgcctttg | 60 |
| cggatacact gtgtattggc taccacgcca acaatagcac cgataccgtg gatacagtgc | 120 |
| tggagaagaa tgtgaccgtg acccactctg tgaatctgct ggaggataag cacaatggca | 180 |
| agctgtgtaa gctgagagga gttgcccctc tgcacctggg caaatgtaat attgccggct | 240 |
| ggattctggg aaatcctgaa tgtgaaagcc tgtctacagc cagcagctgg tcttatatcg | 300 |
| tggaaacccc tagcagcgac aatggcacct gttaccctgg cgacttcatc gattacgagg | 360 |
| agctgagaga acagctgtct agcgtgtcca gcttcgagag attcgagatc ttccctaaga | 420 |
| caagcagctg gcctaatcac gattctaata agggagtgac agccgcctgt cctcatgccg | 480 |
| gagccaagtc cttttacaag aacctgatct ggctggtgaa aagggcaac agctacccta | 540 |
| agctgtctaa gagctacatc aacgacaagg gcaaagaagt gctggtgctg tggggaatcc | 600 |
| accaccctag cacaagcgcc gatcagcaga gcctgtacca gaatgccgat gcctatgtgt | 660 |
| tcgtgggcag cagcagatac agcaaaaagt tcaagcctga aattgccatt agacccaaag | 720 |
| tgagagatca ggaaggcaga atgaattact actggaccct ggtggaacct ggcgataaga | 780 |
| tcacatttga ggccaccgga atctggtgg tgcctagata tgcatttgct atggagagaa | 840 |
| atgctggctc tggcatcatt atctctgata ccctgtgca cgactgtaat accacctgtc | 900 |
| agacacctaa gggcgccatt aataccagcc tgcccttcca gaatattcac cctatcacca | 960 |
| tcggcaagtg tcctaagtat gtgaagagca ccaagctgag actggctacc ggtctgagaa | 1020 |
| atatccctag catccagagc agaggcctgt ttggagccat cgccggcttt attgagggag | 1080 |
| gatggaccgg aatggtggat ggctggtacg gctatcacca ccagaatgag cagggatccg | 1140 |
| gatatgccgc cgatctgaag tctacacaga acgccatcga cgagatcaca aacaaggtga | 1200 |
| acagcgtgat cgagaagatg aacacccagt ttacagctgt gggcaaggag ttcaaccacc | 1260 |
| tggagaagag aatcgagaac ctgaacaaga agtggacga cggcttcctg gatatttgga | 1320 |
| cctacaatgc cgagctgctc gtgctcctgg agaatgagag aaccctggac taccacgaca | 1380 |
| gcaatgtgaa gaacctgtac gagaaggtga aagccagct gaagaacaat gccaaggaga | 1440 |
| tcggcaacgg ctgctttgag ttctaccaca gtgtgacaa cacctgtatg gagtctgtga | 1500 |
| agaacggcac ctacgactac cctaagtata gcgaggaggc caagctgaat agagaggaga | 1560 |
| tcgacggcgt gaaactggaa agcacaagaa tctatcaggg cgctgaaaac ctgtatttc | 1620 |
| agggcggttc tggttacatc ccggaagctc cgcgtgacgg tcaggcttac gttcgtaaag | 1680 |
| acggtgaatg ggttctgctg tctaccttcc tgggtcacca tcatcaccac catcaccatc | 1740 |
| atcactgata aaagctt | 1757 |

<210> SEQ ID NO 11
<211> LENGTH: 584
<212> TYPE: PRT
<213> ORGANISM: Artificial Sequence
<220> FEATURE:
<223> OTHER INFORMATION: Synthetic

<400> SEQUENCE: 11

```
Met Val Ser Ala Ile Val Leu Tyr Val Leu Leu Ala Ala Ala Ala His
1               5                   10                  15
Ser Ala Phe Ala Asp Thr Leu Cys Ile Gly Tyr His Ala Asn Asn Ser
            20                  25                  30
Thr Asp Thr Val Asp Thr Val Leu Glu Lys Asn Val Thr Val Thr His
        35                  40                  45
Ser Val Asn Leu Leu Glu Asp Lys His Asn Gly Lys Leu Cys Lys Leu
    50                  55                  60
Arg Gly Val Ala Pro Leu His Leu Gly Lys Cys Asn Ile Ala Gly Trp
65                  70                  75                  80
Ile Leu Gly Asn Pro Glu Cys Glu Ser Leu Ser Thr Ala Ser Ser Trp
                85                  90                  95
Ser Tyr Ile Val Glu Thr Pro Ser Ser Asp Asn Gly Thr Cys Tyr Pro
            100                 105                 110
Gly Asp Phe Ile Asp Tyr Glu Glu Leu Arg Glu Gln Leu Ser Ser Val
        115                 120                 125
Ser Ser Phe Glu Arg Phe Glu Ile Phe Pro Lys Thr Ser Ser Trp Pro
    130                 135                 140
Asn His Asp Ser Asn Lys Gly Val Thr Ala Ala Cys Pro His Ala Gly
145                 150                 155                 160
Ala Lys Ser Phe Tyr Lys Asn Leu Ile Trp Leu Val Lys Lys Gly Asn
                165                 170                 175
Ser Tyr Pro Lys Leu Ser Lys Ser Tyr Ile Asn Asp Lys Gly Lys Glu
            180                 185                 190
Val Leu Val Leu Trp Gly Ile His His Pro Ser Thr Ser Ala Asp Gln
        195                 200                 205
Gln Ser Leu Tyr Gln Asn Ala Asp Ala Tyr Val Phe Val Gly Ser Ser
    210                 215                 220
Arg Tyr Ser Lys Lys Phe Lys Pro Glu Ile Ala Ile Arg Pro Lys Val
225                 230                 235                 240
Arg Asp Gln Glu Gly Arg Met Asn Tyr Tyr Trp Thr Leu Val Glu Pro
                245                 250                 255
Gly Asp Lys Ile Thr Phe Glu Ala Thr Gly Asn Leu Val Val Pro Arg
            260                 265                 270
Tyr Ala Phe Ala Met Glu Arg Asn Ala Gly Ser Gly Ile Ile Ile Ser
        275                 280                 285
Asp Thr Pro Val His Asp Cys Asn Thr Cys Gln Thr Pro Lys Gly
    290                 295                 300
Ala Ile Asn Thr Ser Leu Pro Phe Gln Asn Ile His Pro Ile Thr Ile
305                 310                 315                 320
Gly Lys Cys Pro Lys Tyr Val Lys Ser Thr Lys Leu Arg Leu Ala Thr
                325                 330                 335
Gly Leu Arg Asn Ser Pro Gln Arg Glu Arg Arg Lys Lys Arg Gly Leu
            340                 345                 350
Phe Gly Ala Ile Ala Gly Phe Ile Glu Gly Gly Trp Thr Gly Met Val
        355                 360                 365
Asp Gly Trp Tyr Gly Tyr His His Gln Asn Glu Gln Gly Ser Gly Tyr
    370                 375                 380
Ala Ala Asp Leu Lys Ser Thr Gln Asn Ala Ile Asp Glu Ile Thr Asn
385                 390                 395                 400
Lys Val Asn Ser Val Ile Glu Lys Met Asn Thr Gln Phe Thr Ala Val
                405                 410                 415
```

```
Gly Lys Glu Phe Asn His Leu Glu Lys Arg Ile Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Tyr His Asp Ser Asn
    450                 455                 460

Val Lys Asn Leu Tyr Glu Lys Val Arg Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Thr Cys Met Glu Ser Val Lys Asn Gly Thr Tyr Asp Tyr Pro Lys Tyr
            500                 505                 510

Ser Glu Glu Ala Lys Leu Asn Arg Glu Glu Ile Asp Gly Val Lys Leu
        515                 520                 525

Glu Ser Thr Arg Ile Tyr Gln Gly Ala Glu Asn Leu Tyr Phe Gln Gly
    530                 535                 540

Gly Ser Gly Tyr Ile Pro Glu Ala Pro Arg Asp Gly Gln Ala Tyr Val
545                 550                 555                 560

Arg Lys Asp Gly Glu Trp Val Leu Leu Ser Thr Phe Leu Gly His His
                565                 570                 575

His His His His His His
            580

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Gln Arg Glu Arg Arg Lys Lys Arg
1               5

<210> SEQ ID NO 13
<211> LENGTH: 1766
<212> TYPE: DNA
<213> ORGANISM: Artificial Sequence
<220> FEATURE:
<223> OTHER INFORMATION: Synthetic

<400> SEQUENCE: 13
ccatggtaag cgctattgtt ttatatgtgc ttttggcggc ggcggcgcat tctgcctttg      60
cggatacact gtgtattggc taccacgcca acaatagcac cgataccgtg atacagtgc     120 tggagaagaa tgtgaccgtg acccactctg tgaatctgct ggaggataag cacaatggca     180
agctgtgtaa gctgagagga gttgcccctc tgcacctggg caaatgtaat attgccggct     240
ggattctggg aaatcctgaa tgtgaaagcc tgtctacagc cagcagctgg tcttatatcg     300
tggaaacccc tagcagcgac aatggcacct gttaccctgg cgacttcatc gattacgagg     360
agctgagaga acagctgtct agcgtgtcca gcttcgagag attcgagatc ttccctaaga     420
caagcagctg gcctaatcac gattctaata agggagtgac agccgcctgt cctcatgccg     480
gagccaagtc cttttacaag aacctgatct ggctggtgaa gaagggcaac agctacccta     540
agctgtctaa gagctacatc aacgacaagg gcaaagaagt gctggtgctg tggggaatcc     600
accaccctag cacaagcgcc gatcagcaga gcctgtacca gaatgccgat gcctatgtgt     660
```

-continued

```
ttgtgggcag cagcagatac agcaaaaagt tcaagcctga aattgccatt agacccaaag    720
tgagagatca ggaaggcaga atgaattact actggaccct ggtggaacct ggcgataaga    780
tcacatttga ggccaccgga aatctggtgg tgcctagata tgcatttgct atggagagaa    840
atgctggctc tggcatcatt atctctgata cccctgtgca cgactgtaat accacctgtc    900
agacacctaa gggcgccatt aataccagcc tgcccttcca gaatattcac cctatcacca    960
tcggcaagtg tcctaagtat gtgaagagca ccaagctgag actggctacc ggtctgagaa   1020
atagccctca gagggagaga cgcaagaaga gaggcctgtt tggagccatc gccggcttta   1080
ttgagggagg atggaccgga atggtggatg gctggtacgg ctatcaccac cagaatgagc   1140
agggatccgg atatgccgcc gatctgaagt ctacacagaa cgccatcgac gagatcacaa   1200
acaaggtgaa cagcgtgatc gagaagatga cacccagtt tacagctgtg ggcaaggagt    1260
tcaaccacct ggagaagaga atcgagaacc tgaacaagaa agtggacgac ggcttcctgg   1320
atatttggac ctacaatgcc gagctgctcg tgctcctgga gaatgagaga accctggact   1380
accacgacag caatgtgaag aacctgtacg agaaggtgag aagccagctg aagaacaatg   1440
ccaaggagat cggcaacggc tgctttgagt tctaccacaa gtgtgacaac acctgtatgg   1500
agtctgtgaa gaacggcacc tacgactacc ctaagtatag cgaggaggcc aagctgaata   1560
gagaggagat cgacggcgtg aaactggaaa gcacaagaat ctatcagggc gctgaaaacc   1620
tgtatttca gggcggttct ggttacatcc cggaagctcc gcgtgacggt caggcttacg    1680
ttcgtaaaga cggtgaatgg gttctgctgt ctaccttcct gggtcaccat catcaccacc   1740
atcaccatca tcactgataa aagctt                                        1766
```

<210> SEQ ID NO 14
<211> LENGTH: 581
<212> TYPE: PRT
<213> ORGANISM: Artificial Sequence
<220> FEATURE:
<223> OTHER INFORMATION: Synthetic

<400> SEQUENCE: 14

```
Met Val Ser Ala Ile Val Leu Tyr Val Leu Leu Ala Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Lys Thr Ser Ser Trp Pro
    130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
```

```
            165                 170                 175
Ser Tyr Pro Lys Leu Ser Lys Ser Tyr Ile Asn Asp Lys Gly Lys Glu
            180                 185                 190

Val Leu Val Leu Trp Gly Ile His His Pro Ser Thr Ser Ala Asp Gln
            195                 200                 205

Gln Ser Leu Tyr Gln Asn Ala Asp Ala Tyr Val Phe Val Gly Ser Ser
    210                 215                 220

Arg Tyr Ser Lys Lys Phe Lys Pro Glu Ile Ala Ile Arg Pro Lys Val
225                 230                 235                 240

Arg Asp Gln Glu Gly Arg Met Asn Tyr Tyr Trp Thr Leu Val Glu Pro
                245                 250                 255

Gly Asp Lys Ile Thr Phe Glu Ala Thr Gly Asn Leu Val Val Pro Arg
            260                 265                 270

Tyr Ala Phe Ala Met Glu Arg Asn Ala Gly Ser Gly Ile Ile Ile Ser
            275                 280                 285

Asp Thr Pro Val His Asp Cys Asn Thr Cys Gln Thr Pro Lys Gly
            290                 295                 300

Ala Ile Asn Thr Ser Leu Pro Phe Gln Asn Ile His Pro Ile Thr Ile
305                 310                 315                 320

Gly Lys Cys Pro Lys Tyr Val Lys Ser Thr Lys Leu Arg Leu Ala Thr
                325                 330                 335

Gly Leu Arg Asn Ile Pro Arg Arg Arg Arg Gly Leu Phe Gly Ala
            340                 345                 350

Ile Ala Gly Phe Ile Glu Gly Gly Trp Thr Gly Met Val Asp Gly Trp
            355                 360                 365

Tyr Gly Tyr His His Gln Asn Glu Gln Gly Ser Gly Tyr Ala Ala Asp
    370                 375                 380

Leu Lys Ser Thr Gln Asn Ala Ile Asp Glu Ile Thr Asn Lys Val Asn
385                 390                 395                 400

Ser Val Ile Glu Lys Met Asn Thr Gln Phe Thr Ala Val Gly Lys Glu
                405                 410                 415

Phe Asn His Leu Glu Lys Arg Ile Glu Asn Leu Asn Lys Lys Val Asp
            420                 425                 430

Asp Gly Phe Leu Asp Ile Trp Thr Tyr Asn Ala Glu Leu Leu Val Leu
            435                 440                 445

Leu Glu Asn Glu Arg Thr Leu Asp Tyr His Asp Ser Asn Val Lys Asn
450                 455                 460

Leu Tyr Glu Lys Val Arg Ser Gln Leu Lys Asn Asn Ala Lys Glu Ile
465                 470                 475                 480

Gly Asn Gly Cys Phe Glu Phe Tyr His Lys Cys Asp Asn Thr Cys Met
                485                 490                 495

Glu Ser Val Lys Asn Gly Thr Tyr Asp Tyr Pro Lys Tyr Ser Glu Glu
            500                 505                 510

Ala Lys Leu Asn Arg Glu Glu Ile Asp Gly Val Lys Leu Glu Ser Thr
            515                 520                 525

Arg Ile Tyr Gln Gly Ala Glu Asn Leu Tyr Phe Gln Gly Gly Ser Gly
    530                 535                 540

Tyr Ile Pro Glu Ala Pro Arg Asp Gly Gln Ala Tyr Val Arg Lys Asp
545                 550                 555                 560

Gly Glu Trp Val Leu Leu Ser Thr Phe Leu Gly His His His His
                565                 570                 575

His His His His His
            580
```

<210> SEQ ID NO 15
<211> LENGTH: 1757
<212> TYPE: DNA
<213> ORGANISM: Artificial Sequence
<220> FEATURE:
<223> OTHER INFORMATION: Synthetic

<400> SEQUENCE: 15

| | |
|---|---|
| ccatggtaag cgctattgtt ttatatgtgc ttttggcggc ggcggcgcat tctgcctttg | 60 |
| cggatacact gtgtattggc taccacgcca acaatagcac cgataccgtg gatacagtgc | 120 |
| tggagaagaa tgtgaccgtg acccactctg tgaatctgct ggaggataag cacaatggca | 180 |
| agctgtgtaa gctgagagga gttgcccctc tgcacctggg caaatgtaat attgccggct | 240 |
| ggattctggg aaatcctgaa tgtgaaagcc tgtctacagc cagcagctgg tcttatatcg | 300 |
| tggaaacccc tagcagcgac aatggcacct gttaccctgg cgacttcatc gattacgagg | 360 |
| agctgagaga acagctgtct agcgtgtcca gcttcgagag attcgagatc ttccctaaga | 420 |
| caagcagctg gcctaatcac gattctaata agggagtgac agccgcctgt cctcatgccg | 480 |
| gagccaagtc cttttacaag aacctgatct ggctggtgaa gaagggcaac agctacccta | 540 |
| agctgtctaa gagctacatc aacgacaagg gcaaagaagt gctggtgctg tggggaatcc | 600 |
| accaccctag cacaagcgcc gatcagcaga gcctgtacca gaatgccgat gcctatgtgt | 660 |
| ttgtgggcag cagcagatac agcaaaaagt tcaagcctga aattgccatt agacccaaag | 720 |
| tgagagatca ggaaggcaga atgaattact actggaccct ggtggaacct ggcgataaga | 780 |
| tcacatttga ggccaccgga aatctggtgg tgcctagata tgcatttgct atggagagaa | 840 |
| atgctggctc tggcatcatt atctctgata cccctgtgca cgactgtaat accacctgtc | 900 |
| agacacctaa gggcgccatt aataccagcc tgcccttcca gaatattcac cctatcacca | 960 |
| tcggcaagtg tcctaagtat gtgaagagca ccaagctgag actggctacc ggtctgagaa | 1020 |
| atatccctag gagacgcaga agaggcctgt ttggagccat cgccggcttt attgagggag | 1080 |
| gatggaccgg aatggtggat ggctggtacg gctatcacca ccagaatgag cagggatccg | 1140 |
| gatatgccgc cgatctgaag tctacacaga acgccatcga cgagatcaca acaaggtga | 1200 |
| acagcgtgat cgagaagatg aacacccagt ttacagctgt gggcaaggag ttcaaccacc | 1260 |
| tggagaagag aatcgagaac ctgaacaaga agtggacga cggcttcctg gatatttgga | 1320 |
| cctacaatgc cgagctgctc gtgctcctgg agaatgagag aaccctggac taccacgaca | 1380 |
| gcaatgtgaa gaacctgtac gagaaggtga agagccagct gaagaacaat gccaaggaga | 1440 |
| tcggcaacgg ctgctttgag ttctaccaca gtgtgacaa cacctgtatg gagtctgtga | 1500 |
| agaacggcac ctacgactac cctaagtata gcgaggaggc caagctgaat agagaggaga | 1560 |
| tcgacggcgt gaaactggaa agcacaagaa tctatcaggg cgctgaaaac ctgtatttc | 1620 |
| agggcggttc tggttacatc ccggaagctc cgcgtgacgg tcaggcttac gttcgtaaag | 1680 |
| acggtgaatg ggttctgctg tctaccttcc tgggtcacca tcatcaccac catcaccatc | 1740 |
| atcactgata aaagctt | 1757 |

<210> SEQ ID NO 16
<211> LENGTH: 585
<212> TYPE: PRT
<213> ORGANISM: Artificial Sequence
<220> FEATURE:
<223> OTHER INFORMATION: Synthetic

<400> SEQUENCE: 16

```
Met Val Ser Ala Ile Val Leu Tyr Val Leu Leu Ala Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Lys Thr Ser Ser Trp Pro
    130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
                165                 170                 175

Ser Tyr Pro Lys Leu Ser Lys Ser Tyr Ile Asn Asp Lys Gly Lys Glu
            180                 185                 190

Val Leu Val Leu Trp Gly Ile His His Pro Ser Thr Ser Ala Asp Gln
        195                 200                 205

Gln Ser Leu Tyr Gln Asn Ala Asp Ala Tyr Val Phe Val Gly Ser Ser
    210                 215                 220

Arg Tyr Ser Lys Lys Phe Lys Pro Glu Ile Ala Ile Arg Pro Lys Val
225                 230                 235                 240

Arg Asp Gln Glu Gly Arg Met Asn Tyr Tyr Trp Thr Leu Val Glu Pro
                245                 250                 255

Gly Asp Lys Ile Thr Phe Glu Ala Thr Gly Asn Leu Val Val Pro Arg
            260                 265                 270

Tyr Ala Phe Ala Met Glu Arg Asn Ala Gly Ser Gly Ile Ile Ile Ser
        275                 280                 285

Asp Thr Pro Val His Asp Cys Asn Thr Thr Cys Gln Thr Pro Lys Gly
    290                 295                 300

Ala Ile Asn Thr Ser Leu Pro Phe Gln Asn Ile His Pro Ile Thr Ile
305                 310                 315                 320

Gly Lys Cys Pro Lys Tyr Val Lys Ser Thr Lys Leu Arg Leu Ala Thr
                325                 330                 335

Gly Leu Arg Asn Ile Pro Ser Ile Gln Ser Arg Arg Arg Arg Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
                405                 410                 415
```

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
    450                 455                 460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
            485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Glu Ile Asp Gly Val Lys
        515                 520                 525

Leu Glu Ser Thr Arg Ile Tyr Gln Gly Ala Glu Asn Leu Tyr Phe Gln
    530                 535                 540

Gly Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly His
            565                 570                 575

His His His His His His His His
            580                 585

<210> SEQ ID NO 17
<211> LENGTH: 1769
<212> TYPE: DNA
<213> ORGANISM: Artificial Sequence
<220> FEATURE:
<223> OTHER INFORMATION: Synthetic

<400> SEQUENCE: 17
ccatggtaag cgctattgtt ttatatgtgc ttttggcggc ggcggcgcat tctgcctttg      60
cggatacact gtgtattggc taccacgcca acaatagcac cgataccgtg atacagtgc     120 tggagaagaa tgtgaccgtg acccactctg tgaatctgct ggaggataag cacaatggca    180
agctgtgtaa gctgagagga gttgcccctc tgcacctggg caaatgtaat attgccggct    240
ggattctggg aaatcctgaa tgtgaaagcc tgtctacagc cagcagctgg tcttatatcg    300
tggaaacccc tagcagcgac aatggcacct gttaccctgg cgacttcatc gattacgagg    360
agctgagaga acagcctgtct agcgtgtcca gcttcgagag attcgagatc ttccctaaga    420
caagcagctg gcctaatcac gattctaata agggagtgac agccgcctgt cctcatgccg    480
gagccaagtc ctttttacaag aacctgatct ggctggtgaa gaagggcaac agctacccta    540
agctgtctaa gagctacatc aacgacaagg gcaaagaagt gctggtgctg tggggaatcc    600
accaccctag cacaagcgcc gatcagcaga cctgtaccag aatgccgat gcctatgtgt     660 tgtgggcag cagcagatac agcaaaaagt tcaagcctga aattgccatt agacccaaag     720
tgagagatca ggaaggcaga atgaattact actggaccct ggtggaacct ggcgataaga    780
tcacatttga ggccaccgga aatctggtgg tgcctagata tgcatttgct atggagagaa    840
atgctggctc tggcatcatt atctctgata cccctgtgca cgactgtaat accacctgtc    900
agacacctaa gggcgccatt aataccagcc tgcccttcca gaatattcac cctatcacca    960
tcggcaagtg tcctaagtat gtgaagagca ccaagctgag actggctacc ggtctgagaa   1020 atatcccta gcatccagag caggagacgca gaagaggcct gtttggagcc atcgccggct   1080

-continued

```
ttattgaggg aggatggacc ggaatggtgg atggctggta cggctatcac caccagaatg    1140
agcagggatc cggatatgcc gccgatctga agtctacaca gaacgccatc gacgagatca    1200
caaacaaggt gaacagcgtg atcgagaaga tgaacaccca gtttacagct gtgggcaagg    1260
agttcaacca cctggagaag agaatcgaga acctgaacaa gaaagtggac gacggcttcc    1320
tggatatttg gacctacaat gccgagctgc tcgtgctcct ggagaatgag agaaccctgg    1380
actaccacga cagcaatgtg aagaacctgt acgagaaggt gagaagccag ctgaagaaca    1440
atgccaagga gatcggcaac ggctgctttg agttctacca caagtgtgac aacacctgta    1500
tggagtctgt gaagaacggc accctacgact accctaagta tagcgaggag gccaagctga    1560
atagagagga gatcgacggc gtgaaactgg aaagcacaag aatctatcag ggcgctgaaa    1620
acctgtattt tcagggcggt tctggttaca tcccggaagc tccgcgtgac ggtcaggctt    1680
acgttcgtaa agacggtgaa tgggttctgc tgtctacctt cctgggtcac catcatcacc    1740
accatcacca tcatcactga taaaagctt                                      1769
```

<210> SEQ ID NO 18
<211> LENGTH: 581
<212> TYPE: PRT
<213> ORGANISM: Artificial Sequence
<220> FEATURE:
<223> OTHER INFORMATION: Synthetic

<400> SEQUENCE: 18

```
Met Val Ser Ala Ile Val Leu Tyr Val Leu Leu Ala Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Lys Thr Ser Ser Trp Pro
    130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
                165                 170                 175

Ser Tyr Pro Lys Leu Ser Lys Ser Tyr Ile Asn Asp Lys Gly Lys Glu
            180                 185                 190

Val Leu Val Leu Trp Gly Ile His His Pro Ser Thr Ser Ala Asp Gln
        195                 200                 205

Gln Ser Leu Tyr Gln Asn Ala Asp Ala Tyr Val Phe Val Gly Ser Ser
    210                 215                 220

Arg Tyr Ser Lys Lys Phe Lys Pro Glu Ile Ala Ile Arg Pro Lys Val
225                 230                 235                 240
```

Arg Asp Gln Glu Gly Arg Met Asn Tyr Tyr Trp Thr Leu Val Glu Pro
            245                 250                 255

Gly Asp Lys Ile Thr Phe Glu Ala Thr Gly Asn Leu Val Val Pro Arg
            260                 265                 270

Tyr Ala Phe Ala Met Glu Arg Asn Ala Gly Ser Gly Ile Ile Ile Ser
            275                 280                 285

Asp Thr Pro Val His Asp Cys Asn Thr Cys Gln Thr Pro Lys Gly
            290                 295                 300

Ala Ile Asn Thr Ser Leu Pro Phe Gln Asn Ile His Pro Ile Thr Ile
305                 310                 315                 320

Gly Lys Cys Pro Lys Tyr Val Lys Ser Thr Lys Leu Arg Leu Ala Thr
            325                 330                 335

Gly Leu Arg Asn Ile Glu Asn Leu Tyr Phe Gln Gly Leu Phe Gly Ala
            340                 345                 350

Ile Ala Gly Phe Ile Glu Gly Gly Trp Thr Gly Met Val Asp Gly Trp
            355                 360                 365

Tyr Gly Tyr His His Gln Asn Glu Gln Gly Ser Gly Tyr Ala Ala Asp
            370                 375                 380

Leu Lys Ser Thr Gln Asn Ala Ile Asp Glu Ile Thr Asn Lys Val Asn
385                 390                 395                 400

Ser Val Ile Glu Lys Met Asn Thr Gln Phe Thr Ala Val Gly Lys Glu
            405                 410                 415

Phe Asn His Leu Glu Lys Arg Ile Glu Asn Leu Asn Lys Lys Val Asp
            420                 425                 430

Asp Gly Phe Leu Asp Ile Trp Thr Tyr Asn Ala Glu Leu Leu Val Leu
            435                 440                 445

Leu Glu Asn Glu Arg Thr Leu Asp Tyr His Asp Ser Asn Val Lys Asn
            450                 455                 460

Leu Tyr Glu Lys Val Arg Ser Gln Leu Lys Asn Asn Ala Lys Glu Ile
465                 470                 475                 480

Gly Asn Gly Cys Phe Glu Phe Tyr His Lys Cys Asp Asn Thr Cys Met
            485                 490                 495

Glu Ser Val Lys Asn Gly Thr Tyr Asp Tyr Pro Lys Tyr Ser Glu Glu
            500                 505                 510

Ala Lys Leu Asn Arg Glu Glu Ile Asp Gly Val Lys Leu Glu Ser Thr
            515                 520                 525

Arg Ile Tyr Gln Gly Ala Glu Asn Leu Tyr Phe Gln Gly Gly Ser Gly
            530                 535                 540

Tyr Ile Pro Glu Ala Pro Arg Asp Gly Gln Ala Tyr Val Arg Lys Asp
545                 550                 555                 560

Gly Glu Trp Val Leu Leu Ser Thr Phe Leu Gly His His His His
            565                 570                 575

His His His His His
            580

<210> SEQ ID NO 19
<211> LENGTH: 1757
<212> TYPE: DNA
<213> ORGANISM: Artificial Sequence
<220> FEATURE:
<223> OTHER INFORMATION: Synthetic

<400> SEQUENCE: 19
ccatggtaag cgctattgtt ttatatgtgc ttttggcggc ggcggcgcat tctgcctttg    60

| | | |
|---|---|---|
| cggatacact gtgtattggc taccacgcca acaatagcac cgataccgtg gatacagtgc | 120 |
| tggagaagaa tgtgaccgtg acccactctg tgaatctgct ggaggataag cacaatggca | 180 |
| agctgtgtaa gctgagagga gttgcccctc tgcacctggg caaatgtaat attgccggct | 240 |
| ggattctggg aaatcctgaa tgtgaaagcc tgtctacagc cagcagctgg tcttatatcg | 300 |
| tggaaacccc tagcagcgac aatggcacct gttaccctgg cgacttcatc gattacgagg | 360 |
| agctgagaga acagctgtct agcgtgtcca gcttcgagag attcgagatc ttccctaaga | 420 |
| caagcagctg gcctaatcac gattctaata agggagtgac agccgcctgt cctcatgccg | 480 |
| gagccaagtc cttttacaag aacctgatct ggctggtgaa gaagggcaac agctacccta | 540 |
| agctgtctaa gagctacatc aacgacaagg gcaaagaagt gctggtgctg tggggaatcc | 600 |
| accaccctag cacaagcgcc gatcagcaga gcctgtacca gaatgccgat gcctatgtgt | 660 |
| tgtgggcag cagcagatac agcaaaaagt tcaagcctga aattgccatt agacccaaag | 720 |
| tgagagatca ggaaggcaga atgaattact actggaccct ggtggaacct ggcgataaga | 780 |
| tcacatttga ggccaccgga aatctggtgg tgcctagata tgcatttgct atggagagaa | 840 |
| atgctggctc tggcatcatt atctctgata cccctgtgca cgactgtaat accacctgtc | 900 |
| agacacctaa gggcgccatt aataccagcc tgcccttcca gaatattcac cctatcacca | 960 |
| tcggcaagtg tcctaagtat gtgaagagca ccaagctgag actggctacc ggtctgagaa | 1020 |
| atatcgaaaa cctgtatttt caaggcctgt ttggagccat cgccggcttt attgagggag | 1080 |
| gatggaccgg aatggtggat ggctggtacg gctatcacca ccagaatgag cagggatccg | 1140 |
| gatatgccgc cgatctgaag tctacacaga acgccatcga cgagatcaca aacaaggtga | 1200 |
| acagcgtgat cgagaagatg aacacccagt ttacagctgt gggcaaggag ttcaaccacc | 1260 |
| tggagaaag aatcgagaac ctgaacaaga agtggacga cggcttcctg gatatttgga | 1320 |
| cctacaatgc cgagctgctc gtgctcctgg agaatgagag aaccctggac taccacgaca | 1380 |
| gcaatgtgaa gaacctgtac gagaaggtga agccagct gaagaacaat gccaaggaga | 1440 |
| tcggcaacgg ctgctttgag ttctaccaca gtgtgacaa cacctgtatg gagtctgtga | 1500 |
| agaacggcac ctacgactac cctaagtata gcgaggaggc caagctgaat agagaggaga | 1560 |
| tcgacggcgt gaaactggaa agcacaagaa tctatcaggg cgctgaaaac ctgtattttc | 1620 |
| agggcggttc tggttacatc ccggaagctc cgcgtgacgg tcaggcttac gttcgtaaag | 1680 |
| acggtgaatg ggttctgctg tctaccttcc tgggtcacca tcatcaccac catcaccatc | 1740 |
| atcactgata aaagctt | 1757 |

<210> SEQ ID NO 20
<211> LENGTH: 582
<212> TYPE: PRT
<213> ORGANISM: Artificial Sequence
<220> FEATURE:
<223> OTHER INFORMATION: Synthetic

<400> SEQUENCE: 20

Met Val Ser Ala Ile Val Leu Tyr Val Leu Leu Ala Ala Ala Ala His
1               5                   10                  15

Ser Ala Phe Ala Asp Thr Leu Cys Ile Gly Tyr His Ala Asn Asn Ser
                20                  25                  30

Thr Asp Thr Val Asp Thr Val Leu Glu Lys Asn Val Thr Val Thr His
            35                  40                  45

Ser Val Asn Leu Leu Glu Asp Lys His Asn Gly Lys Leu Cys Lys Leu
        50                  55                  60

```
Arg Gly Val Ala Pro Leu His Leu Gly Lys Cys Asn Ile Ala Gly Trp
 65              70                  75                  80

Ile Leu Gly Asn Pro Glu Cys Glu Ser Leu Ser Thr Ala Ser Ser Trp
             85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
            115                 120                 125

Ser Ser Phe Glu Arg Phe Glu Ile Phe Pro Lys Thr Ser Ser Trp Pro
130             135                 140

Asn His Asp Ser Asn Lys Gly Val Thr Ala Ala Cys Pro His Ala Gly
145             150                 155                 160

Ala Lys Ser Phe Tyr Lys Asn Leu Ile Trp Leu Val Lys Lys Gly Asn
                165                 170                 175

Ser Tyr Pro Lys Leu Ser Lys Ser Tyr Ile Asn Asp Lys Gly Lys Glu
            180                 185                 190

Val Leu Val Leu Trp Gly Ile His His Pro Ser Thr Ser Ala Asp Gln
            195                 200                 205

Gln Ser Leu Tyr Gln Asn Ala Asp Ala Tyr Val Phe Val Gly Ser Ser
210             215                 220

Arg Tyr Ser Lys Lys Phe Lys Pro Glu Ile Ala Ile Arg Pro Lys Val
225             230                 235                 240

Arg Asp Gln Glu Gly Arg Met Asn Tyr Tyr Trp Thr Leu Val Glu Pro
                245                 250                 255

Gly Asp Lys Ile Thr Phe Glu Ala Thr Gly Asn Leu Val Val Pro Arg
            260                 265                 270

Tyr Ala Phe Ala Met Glu Arg Asn Ala Gly Ser Gly Ile Ile Ile Ser
            275                 280                 285

Asp Thr Pro Val His Asp Cys Asn Thr Thr Cys Gln Thr Pro Lys Gly
290             295                 300

Ala Ile Asn Thr Ser Leu Pro Phe Gln Asn Ile His Pro Ile Thr Ile
305             310                 315                 320

Gly Lys Cys Pro Lys Tyr Val Lys Ser Thr Lys Leu Arg Leu Ala Thr
            325                 330                 335

Gly Leu Arg Asn Ser Pro Glu Asn Leu Tyr Phe Gln Gly Leu Phe Gly
            340                 345                 350

Ala Ile Ala Gly Phe Ile Glu Gly Gly Trp Thr Gly Met Val Asp Gly
            355                 360                 365

Trp Tyr Gly Tyr His His Gln Asn Glu Gln Gly Ser Gly Tyr Ala Ala
            370                 375                 380

Asp Leu Lys Ser Thr Gln Asn Ala Ile Asp Glu Ile Thr Asn Lys Val
385             390                 395                 400

Asn Ser Val Ile Glu Lys Met Asn Thr Gln Phe Thr Ala Val Gly Lys
                405                 410                 415

Glu Phe Asn His Leu Glu Lys Arg Ile Glu Asn Leu Asn Lys Lys Val
            420                 425                 430

Asp Asp Gly Phe Leu Asp Ile Trp Thr Tyr Asn Ala Glu Leu Leu Val
            435                 440                 445

Leu Leu Glu Asn Glu Arg Thr Leu Asp Tyr His Asp Ser Asn Val Lys
450             455                 460

Asn Leu Tyr Glu Lys Val Arg Ser Gln Leu Lys Asn Asn Ala Lys Glu
465             470                 475                 480
```

```
Ile Gly Asn Gly Cys Phe Glu Phe Tyr His Lys Cys Asp Asn Thr Cys
                485                 490                 495

Met Glu Ser Val Lys Asn Gly Thr Tyr Asp Tyr Pro Lys Tyr Ser Glu
        500                 505                 510

Glu Ala Lys Leu Asn Arg Glu Glu Ile Asp Gly Val Lys Leu Glu Ser
            515                 520                 525

Thr Arg Ile Tyr Gln Gly Ala Glu Asn Leu Tyr Phe Gln Gly Gly Ser
        530                 535                 540

Gly Tyr Ile Pro Glu Ala Pro Arg Asp Gly Gln Ala Tyr Val Arg Lys
545                 550                 555                 560

Asp Gly Glu Trp Val Leu Leu Ser Thr Phe Leu Gly His His His
                565                 570                 575

His His His His His His
            580

<210> SEQ ID NO 21
<211> LENGTH: 1760
<212> TYPE: DNA
<213> ORGANISM: Artificial Sequence
<220> FEATURE:
<223> OTHER INFORMATION: Synthetic

<400> SEQUENCE: 21
ccatggtaag cgctattgtt ttatatgtgc ttttggcggc ggcggcgcat tctgcctttg      60
cggatacact gtgtattggc taccacgcca acaatagcac cgataccgtg gatacagtgc    120
tggagaagaa tgtgaccgtg acccactctg tgaatctgct ggaggataag cacaatggca    180
agctgtgtaa gctgagagga gttgcccctc tgcacctggg caaatgtaat attgccggct    240
ggattctggg aaatcctgaa tgtgaaagcc tgtctacagc cagcagctgg tcttatatcg    300
tggaaacccc tagcagcgac aatggcacct gttaccctgg cgacttcatc gattacgagg    360
agctgagaga acagctgtct agcgtgtcca gcttcgagag attcgagatc ttccctaaga    420
caagcagctg gcctaatcac gattctaata agggagtgac agccgcctgt cctcatgccg    480
gagccaagtc cttttacaag aacctgatct ggctggtgaa gaagggcaac agctacccta    540
agctgtctaa gagctacatc aacgacaagg gcaaagaagt gctggtgctg tggggaatcc    600
accaccctag cacaagcgcc gatcagcaga gcctgtacca gaatgccgat gcctatgtgt    660 tgtgggcag cagcagatac agcaaaaagt tcaagcctga aattgccatt agacccaaag    720
tgagagatca ggaaggcaga atgaattact actggaccct ggtggaacct ggcgataaga    780
tcacatttga ggccaccgga aatctggtgg tgcctagata tgcatttgct atggagagaa    840
atgctggctc tggcatcatt atctctgata ccctgtgca cgactgtaat accacctgtc    900
agacacctaa gggcgccatt aataccagcc tgcccttcca gaatattcac cctatcacca    960
tcggcaagtg tcctaagtat gtgaagagca ccaagctgag actggctacc ggtctgagaa    1020
atagccctga aaacctgtat tttcaaggcc tgtttggagc catcgccggc tttattgagg    1080
gaggatggac cggaatggtg gatggctggt acggctatca ccaccagaat gagcagggat    1140
ccggatatgc cgccgatctg aagtctacac agaacgccat cgacgagatc acaaacaagg    1200
tgaacagcgt gatcgagaag atgaacaccc agtttacagc tgtgggcaag gagttcaacc    1260
acctggagaa gagaatcgag aacctgaaca agaaagtgga cgacggcttc ctggatattt    1320
ggacctacaa tgccgagctg ctcgtgctcc tggagaatga gagaacccctg gactaccacg    1380 acagcaatgt gaagaacctg tacgagaagg tgagaagcca gctgaagaac aatgccaagg    1440
```

-continued

```
agatcggcaa cggctgcttt gagttctacc acaagtgtga caacacctgt atggagtctg    1500
tgaagaacgg cacctacgac taccctaagt atagcgagga ggccaagctg aatagagagg    1560
agatcgacgg cgtgaaactg gaaagcacaa gaatctatca gggcgctgaa aacctgtatt    1620
ttcagggcgg ttctggttac atcccggaag ctccgcgtga cggtcaggct tacgttcgta    1680
aagacggtga atgggttctg ctgtctacct tcctgggtca ccatcatcac caccatcacc    1740
atcatcactg ataaaagctt                                                1760
```

<210> SEQ ID NO 22
<211> LENGTH: 584
<212> TYPE: PRT
<213> ORGANISM: Artificial Sequence
<220> FEATURE:
<223> OTHER INFORMATION: Synthetic

<400> SEQUENCE: 22

```
Met Val Ser Ala Ile Val Leu Tyr Val Leu Leu Ala Ala Ala Ala His
1               5                  10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Lys Thr Ser Ser Trp Pro
    130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
                165                 170                 175

Ser Tyr Pro Lys Leu Ser Lys Ser Tyr Ile Asn Asp Lys Gly Lys Glu
            180                 185                 190

Val Leu Val Leu Trp Gly Ile His His Pro Ser Thr Ser Ala Asp Gln
        195                 200                 205

Gln Ser Leu Tyr Gln Asn Ala Asp Ala Tyr Val Phe Val Gly Ser Ser
    210                 215                 220

Arg Tyr Ser Lys Lys Phe Lys Pro Glu Ile Ala Ile Arg Pro Lys Val
225                 230                 235                 240

Arg Asp Gln Glu Gly Arg Met Asn Tyr Tyr Trp Thr Leu Val Glu Pro
                245                 250                 255

Gly Asp Lys Ile Thr Phe Glu Ala Thr Gly Asn Leu Val Val Pro Arg
            260                 265                 270

Tyr Ala Phe Ala Met Glu Arg Asn Ala Gly Ser Gly Ile Ile Ile Ser
        275                 280                 285

Asp Thr Pro Val His Asp Cys Asn Thr Thr Cys Gln Thr Pro Lys Gly
    290                 295                 300
```

```
Ala Ile Asn Thr Ser Leu Pro Phe Gln Asn Ile His Pro Ile Thr Ile
305                 310                 315                 320

Gly Lys Cys Pro Lys Tyr Val Lys Ser Thr Lys Leu Arg Leu Ala Thr
            325                 330                 335

Gly Leu Arg Asn Ile Pro Ser Ile Glu Asn Leu Tyr Phe Gln Gly Leu
        340                 345                 350

Phe Gly Ala Ile Ala Gly Phe Ile Glu Gly Gly Trp Thr Gly Met Val
    355                 360                 365

Asp Gly Trp Tyr Gly Tyr His His Gln Asn Glu Gln Gly Ser Gly Tyr
370                 375                 380

Ala Ala Asp Leu Lys Ser Thr Gln Asn Ala Ile Asp Glu Ile Thr Asn
385                 390                 395                 400

Lys Val Asn Ser Val Ile Glu Lys Met Asn Thr Gln Phe Thr Ala Val
                405                 410                 415

Gly Lys Glu Phe Asn His Leu Glu Lys Arg Ile Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Tyr His Asp Ser Asn
450                 455                 460

Val Lys Asn Leu Tyr Glu Lys Val Arg Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Thr Cys Met Glu Ser Val Lys Asn Gly Thr Tyr Asp Tyr Pro Lys Tyr
            500                 505                 510

Ser Glu Glu Ala Lys Leu Asn Arg Glu Ile Asp Gly Val Lys Leu
        515                 520                 525

Glu Ser Thr Arg Ile Tyr Gln Gly Ala Glu Asn Leu Tyr Phe Gln Gly
    530                 535                 540

Gly Ser Gly Tyr Ile Pro Glu Ala Pro Arg Asp Gly Gln Ala Tyr Val
545                 550                 555                 560

Arg Lys Asp Gly Glu Trp Val Leu Leu Ser Thr Phe Leu Gly His His
                565                 570                 575

His His His His His His
            580

<210> SEQ ID NO 23
<211> LENGTH: 1766
<212> TYPE: DNA
<213> ORGANISM: Artificial Sequence
<220> FEATURE:
<223> OTHER INFORMATION: Synthetic

<400> SEQUENCE: 23
ccatggtaag cgctattgtt ttatatgtgc ttttggcggc ggcggcgcat tctgcctttg      60
cggatacact gtgtattggc taccacgcca acaatagcac cgataccgtg gatacagtgc     120
tggagaagaa tgtgaccgtg acccactctg tgaatctgct ggaggataag cacaatggca     180
agctgtgtaa gctgagagga gttgcccctc tgcacctggg caatgtaat attgccggct     240 ggattctggg aaatcctgaa tgtgaaagcc tgtctacagc cagcagctgg tcttatatcg     300
tggaaacccc tagcagcgac aatggcacct gttaccctgg cgacttcatc gattacgagg     360
agctgagaga acagctgtct agcgtgtcca gcttcgagag attcgagatc ttccctaaga     420
caagcagctg gcctaatcac gattctaata agggagtgac agccgcctgt cctcatgccg     480
```

-continued

| | |
|---|---|
| gagccaagtc cttttacaag aacctgatct ggctggtgaa aagggcaac agctaccta | 540 |
| agctgtctaa gagctacatc aacgacaagg caaagaagt gctggtgctg tggggaatcc | 600 |
| accaccctag cacaagcgcc gatcagcaga gcctgtacca aatgccgat gcctatgtgt | 660 |
| ttgtgggcag cagcagatac agcaaaaagt tcaagcctga aattgccatt agacccaaag | 720 |
| tgagagatca ggaaggcaga atgaattact actggaccct ggtggaacct ggcgataaga | 780 |
| tcacatttga ggccaccgga aatctggtgg tgcctagata tgcatttgct atggagagaa | 840 |
| atgctggctc tggcatcatt atctctgata cccctgtgca cgactgtaat accacctgtc | 900 |
| agacacctaa gggcgccatt aataccagcc tgcccttcca gaatattcac cctatcacca | 960 |
| tcggcaagtg tcctaagtat gtgaagagca ccaagctgag actggctacc ggtctgagaa | 1020 |
| atatccctag catcgaaaac ctgtattttc aaggcctgtt tggagccatc gccggcttta | 1080 |
| ttgagggagg atggaccgga atggtggatg ctggtacgg ctatcaccac cagaatgagc | 1140 |
| agggatccgg atatgccgcc gatctgaagt ctacacagaa cgccatcgac gagatcacaa | 1200 |
| acaaggtgaa cagcgtgatc gagaagatga cacccagtt tacagctgtg gcaaggagt | 1260 |
| tcaaccacct ggagaagaga atcgagaacc tgaacaagaa agtggacgac ggcttcctgg | 1320 |
| atatttggac ctacaatgcc gagctgctcg tgctcctgga gaatgagaga ccctggact | 1380 |
| accacgacag caatgtgaag aacctgtacg agaaggtgag aagccagctg aagaacaatg | 1440 |
| ccaaggagat cggcaacggc tgctttgagt tctaccacaa gtgtgacaac acctgtatgg | 1500 |
| agtctgtgaa gaacggcacc tacgactacc taagtatag cgaggaggcc aagctgaata | 1560 |
| gagaggagat cgacggcgtg aaactggaaa gcacaagaat ctatcagggc gctgaaaacc | 1620 |
| tgtattttca gggcggttct ggttacatcc cggaagctcc gcgtgacggt caggcttacg | 1680 |
| ttcgtaaaga cggtgaatgg gttctgctgt ctaccttcct gggtcaccat catcaccacc | 1740 |
| atcaccatca tcactgataa aagctt | 1766 |

<210> SEQ ID NO 24
<211> LENGTH: 585
<212> TYPE: PRT
<213> ORGANISM: Artificial Sequence
<220> FEATURE:
<223> OTHER INFORMATION: Synthetic

<400> SEQUENCE: 24

Met Val Ser Ala Ile Val Leu Tyr Val Leu Ala Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

```
Ser Ser Phe Glu Arg Phe Glu Ile Phe Pro Lys Thr Ser Ser Trp Pro
    130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
                165                 170                 175

Ser Tyr Pro Lys Leu Ser Lys Ser Tyr Ile Asn Asp Lys Gly Lys Glu
            180                 185                 190

Val Leu Val Leu Trp Gly Ile His His Pro Ser Thr Ser Ala Asp Gln
        195                 200                 205

Gln Ser Leu Tyr Gln Asn Ala Asp Ala Tyr Val Phe Val Gly Ser Ser
    210                 215                 220

Arg Tyr Ser Lys Lys Phe Lys Pro Glu Gly Met Ile Asp Tyr Glu Gly
225                 230                 235                 240

Thr Gly Gln Ala Ala Gly Arg Met Asn Tyr Tyr Trp Thr Leu Val Glu
                245                 250                 255

Pro Gly Asp Lys Ile Thr Phe Glu Ala Thr Gly Asn Leu Val Val Pro
            260                 265                 270

Arg Tyr Ala Phe Ala Met Glu Arg Asn Ala Gly Ser Gly Ile Ile Ile
        275                 280                 285

Ser Asp Thr Pro Val His Asp Cys Asn Thr Thr Cys Gln Thr Pro Lys
    290                 295                 300

Gly Ala Ile Asn Thr Ser Leu Pro Phe Gln Asn Ile His Pro Ile Thr
305                 310                 315                 320

Ile Gly Lys Cys Pro Lys Tyr Val Lys Ser Thr Lys Leu Arg Leu Ala
                325                 330                 335

Thr Gly Leu Arg Asn Ser Pro Gln Arg Glu Arg Arg Lys Lys Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
    450                 455                 460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Glu Ile Asp Gly Val Lys
        515                 520                 525

Leu Glu Ser Thr Arg Ile Tyr Gln Gly Ala Glu Asn Leu Tyr Phe Gln
    530                 535                 540

Gly Gly Ser Gly Tyr Ile Pro Glu Ala Pro Arg Asp Gly Gln Ala Tyr
```

```
                545                 550                 555                 560
Val Arg Lys Asp Gly Glu Trp Val Leu Leu Ser Thr Phe Leu Gly His
                    565                 570                 575

His His His His His His His His
            580                 585

<210> SEQ ID NO 25
<211> LENGTH: 5
<212> TYPE: PRT
<213> ORGANISM: Artificial Sequence
<220> FEATURE:
<223> OTHER INFORMATION: Synthetic

<400> SEQUENCE: 25

Glu Gly Met Ile Asp
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic

<400> SEQUENCE: 26

Glu Gly Thr Gly Gln Ala Ala
1               5

<210> SEQ ID NO 27
<211> LENGTH: 13
<212> TYPE: PRT
<213> ORGANISM: Artificial Sequence
<220> FEATURE:
<223> OTHER INFORMATION: Synthetic

<400> SEQUENCE: 27

Glu Gly Met Ile Asp Tyr Glu Gly Thr Gly Gln Ala Ala
1               5                   10

<210> SEQ ID NO 28
<211> LENGTH: 1770
<212> TYPE: DNA
<213> ORGANISM: Artificial Sequence
<220> FEATURE:
<223> OTHER INFORMATION: Synthetic

<400> SEQUENCE: 28
ccatggtaag cgctattgtt ttatatgtgc ttttggcggc ggcggcgcat tctgcctttg      60
cggatacact gtgtattggc taccacgcca acaatagcac cgataccgtg gatacagtgc    120
tggagaagaa tgtgaccgtg acccactctg tgaatctgct ggaggataag cacaatggca    180
agctgtgtaa gctgagagga gttgcccctc tgcacctggg caaatgtaat attgccggct    240
ggattctggg aaatcctgaa tgtgaaagcc tgtctacagc cagcagctgg tcttatatcg    300
tggaaccccc tagcagcgac aatggcacct gttaccctgg cgacttcatc gattacgagg    360
agctgagaga acagctgtct agcgtgtcca gcttcgagag attcgagatc ttccctaaga    420
caagcagctg gcctaatcac gattctaata agggagtgac agccgcctgt cctcatgccg    480
gagccaagtc cttttacaag aacctgatct ggctggtgaa gaagggcaac agctaccta    540 agctgtctaa gagctacatc aacgacaagg caaagaagt gctggtgctg tggggaatcc    600
accaccctag cacaagcgcc gatcagcaga gcctgtacca gaatgccgat gcctatgtgt    660
```

-continued

```
ttgtgggcag cagcagatac agcaaaaagt tcaagcctga aggcatgatt gattacgaag    720
gcacaggcca ggcagccggc agaatgaatt actactggac cctggtggaa cctggcgata    780
agatcacatt tgaggccacc ggaaatctgg tggtgcctag atatgcattt gctatggaga    840
gaaatgctgg ctctggcatc attatctctg ataccctgt gcacgactgt aataccacct     900
gtcagacacc taagggcgcc attaatacca gcctgccctt ccagaatatt caccctatca    960
ccatcggcaa gtgtcctaag tatgtgaaga gcaccaagct gagactggct accggtctga   1020
gaaatagccc tcagagggag agacgcaaga agagaggcct gtttggagcc atcgccggct   1080
ttattgaggg aggatggacc ggaatggtgg atggctggta cggctatcac caccagaatg   1140
agcagggatc cggatatgcc gccgatctga agtctacaca gaacgccatc gacgagatca   1200
caaacaaggt gaacagcgtg atcgagaaga tgaacaccca gtttacagct gtgggcaagg   1260
agttcaacca cctggagaag agaatcgaga acctgaacaa gaaagtggac gacggcttcc   1320
tggatatttg gacctacaat gccgagctgc tcgtgctcct ggagaatgag agaaccctgg   1380
actaccacga cagcaatgtg aagaacctgt acgagaaggt gagaagccag ctgaagaaca   1440
atgccaagga gatcggcaac ggctgctttg agttctacca caagtgtgac aacacctgta   1500
tggagtctgt gaagaacggc acctacgact accctaagta tagcgaggag gccaagctga   1560
atagagagga gatcgacggc gtgaaactgg aaagcacaag aatctatcag ggcgctgaaa   1620
acctgtattt tcagggcggt tctggttaca tcccggaagc tccgcgtgac ggtcaggctt   1680
acgttcgtaa agacggtgaa tgggttctgc tgtctacctt cctgggtcac catcatcacc   1740
accatcacca tcatcactga taaaaagctt                                   1770
```

<210> SEQ ID NO 29
<211> LENGTH: 583
<212> TYPE: PRT
<213> ORGANISM: Artificial Sequence
<220> FEATURE:
<223> OTHER INFORMATION: Synthetic

<400> SEQUENCE: 29

```
Met Val Ser Ala Ile Val Leu Tyr Val Leu Leu Ala Ala Ala His
1               5                   10                  15

Ser Ala Phe Ala Asp Thr Leu Cys Ile Gly Tyr His Ala Asn Asn Ser
                20                  25                  30

Thr Asp Thr Val Asp Thr Val Leu Glu Lys Asn Val Thr Val Thr His
            35                  40                  45

Ser Val Asn Leu Leu Glu Asp Lys His Asn Gly Lys Leu Cys Lys Leu
        50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Lys Thr Ser Ser Trp Pro
    130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
```

```
                    165                 170                 175
Ser Tyr Pro Lys Leu Ser Lys Ser Tyr Ile Asn Asp Lys Gly Lys Glu
                180                 185                 190

Val Leu Val Leu Trp Gly Ile His His Pro Ser Thr Ser Ala Asp Gln
                195                 200                 205

Gln Ser Leu Tyr Gln Asn Ala Asp Ala Tyr Val Phe Val Gly Ser Ser
    210                 215                 220

Arg Tyr Ser Lys Lys Phe Lys Pro Glu Gly Met Ile Asp Tyr Glu Gly
225                 230                 235                 240

Thr Gly Gln Ala Ala Gly Arg Met Asn Tyr Tyr Trp Thr Leu Val Glu
                245                 250                 255

Pro Gly Asp Lys Ile Thr Phe Glu Ala Thr Gly Asn Leu Val Val Pro
                260                 265                 270

Arg Tyr Ala Phe Ala Met Glu Arg Asn Ala Gly Ser Gly Ile Ile Ile
                275                 280                 285

Ser Asp Thr Pro Val His Asp Cys Asn Thr Thr Cys Gln Thr Pro Lys
    290                 295                 300

Gly Ala Ile Asn Thr Ser Leu Pro Phe Gln Asn Ile His Pro Ile Thr
305                 310                 315                 320

Ile Gly Lys Cys Pro Lys Tyr Val Lys Ser Thr Lys Leu Arg Leu Ala
                325                 330                 335

Thr Gly Leu Arg Asn Ser Pro Glu Asn Leu Tyr Phe Gln Gly Leu Phe
                340                 345                 350

Gly Ala Ile Ala Gly Phe Ile Glu Gly Gly Trp Thr Gly Met Val Asp
                355                 360                 365

Gly Trp Tyr Gly Tyr His His Gln Asn Glu Gln Gly Ser Gly Tyr Ala
                370                 375                 380

Ala Asp Leu Lys Ser Thr Gln Asn Ala Ile Asp Glu Ile Thr Asn Lys
385                 390                 395                 400

Val Asn Ser Val Ile Glu Lys Met Asn Thr Gln Phe Thr Ala Val Gly
                405                 410                 415

Lys Glu Phe Asn His Leu Glu Lys Arg Ile Glu Asn Leu Asn Lys Lys
                420                 425                 430

Val Asp Asp Gly Phe Leu Asp Ile Trp Thr Tyr Asn Ala Glu Leu Leu
                435                 440                 445

Val Leu Leu Glu Asn Glu Arg Thr Leu Asp Tyr His Asp Ser Asn Val
    450                 455                 460

Lys Asn Leu Tyr Glu Lys Val Arg Ser Gln Leu Lys Asn Asn Ala Lys
465                 470                 475                 480

Glu Ile Gly Asn Gly Cys Phe Glu Phe Tyr His Lys Cys Asp Asn Thr
                485                 490                 495

Cys Met Glu Ser Val Lys Asn Gly Thr Tyr Asp Tyr Pro Lys Tyr Ser
                500                 505                 510

Glu Glu Ala Lys Leu Asn Arg Glu Glu Ile Asp Gly Val Lys Leu Glu
                515                 520                 525

Ser Thr Arg Ile Tyr Gln Gly Ala Glu Asn Leu Tyr Phe Gln Gly Gly
                530                 535                 540

Ser Gly Tyr Ile Pro Glu Ala Pro Arg Asp Gly Gln Ala Tyr Val Arg
545                 550                 555                 560

Lys Asp Gly Glu Trp Val Leu Leu Ser Thr Phe Leu Gly His His His
                565                 570                 575

His His His His His
                580
```

<210> SEQ ID NO 30
<211> LENGTH: 1763
<212> TYPE: DNA
<213> ORGANISM: Artificial Sequence
<220> FEATURE:
<223> OTHER INFORMATION: Synthetic

<400> SEQUENCE: 30

```
ccatggtaag cgctattgtt ttatatgtgc ttttggcggc ggcggcgcat tctgcctttg      60
cggatacact gtgtattggc taccacgcca acaatagcac cgataccgtg gatacagtgc     120
tggagaagaa tgtgaccgtg acccactctg tgaatctgct ggaggataag cacaatggca     180
agctgtgtaa gctgagagga gttgcccctc tgcacctggg caaatgtaat attgccggct     240
ggattctggg aaatcctgaa tgtgaaagcc tgtctacagc cagcagctgg tcttatatcg     300
tggaaacccc tagcagcgac aatggcacct gttaccctgg cgacttcatc gattacgagg     360
agctgagaga acagctgtct agcgtgtcca gcttcgagag attcgagatc ttccctaaga     420
caagcagctg gcctaatcac gattctaata agggagtgac agccgcctgt cctcatgccg     480
gagccaagtc cttttacaag aacctgatct ggctggtgaa gaagggcaac agctacccta     540
agctgtctaa gagctacatc aacgacaagg gcaaagaagt gctggtgctg tggggaatcc     600
accaccctag cacaagcgcc gatcagcaga gcctgtacca gaatgccgat gcctatgtgt     660
tgtgggcag cagcagatac agcaaaaagt tcaagcctga aggcatgatt gattacgaag     720
gcacaggcca ggcagccggc agaatgaatt actactggac cctggtggaa cctggcgata     780
agatcacatt tgaggccacc ggaaatctgg tggtgcctag atatgcattt gctatggaga     840
gaaatgctgg ctctggcatc attatctctg taccccctgt gcacgactgt aataccacct     900
gtcagacacc taagggcgcc attaatacca gcctgccctt ccagaatatt caccctatca     960
ccatcggcaa gtgtcctaag tatgtgaaga gcaccaagct gagactggct accggtctga    1020
gaaatagccc tgaaaacctg tatttcaag gcctgtttgg agccatcgcc ggctttattg    1080
agggaggatg gaccggaatg gtggatggct ggtacggcta tcaccaccag aatgagcagg    1140
gatccggata tgccgccgat ctgaagtcta cacagaacgc catcgacgag atcacaaaca    1200
aggtgaacag cgtgatcgag aagatgaaca cccagtttac agctgtgggc aaggagttca    1260
accacctgga aaagagaatc gagaacctga acaagaaagt ggacgacggc ttcctggata    1320
tttggaccta caatgccgag ctgctcgtgc tcctggagaa tgagagaacc ctggactacc    1380
acgacagcaa tgtgaagaac ctgtacgaga aggtgagaag ccagctgaag aacaatgcca    1440
aggagatcgg caacggctgc tttgagttct accacaagtg tgacaacacc tgtatggagt    1500
ctgtgaagaa cggcacctac gactacccta gtatagcga ggaggccaag ctgaatagag    1560
aggagatcga cggcgtgaaa ctggaaagca agaatctca tcagggcgct gaaaacctgt    1620
attttcaggg cggttctggt tacatcccgg aagctccgcg tgacggtcag gcttacgttc    1680
gtaaagacgg tgaatgggtt ctgctgtcta ccttcctggg tcaccatcat caccaccatc    1740
accatcatca ctgataaaag ctt                                            1763
```

<210> SEQ ID NO 31
<211> LENGTH: 590
<212> TYPE: PRT
<213> ORGANISM: Artificial Sequence
<220> FEATURE:
<223> OTHER INFORMATION: Synthetic

```
<400> SEQUENCE: 31

Met Val Ser Ala Ile Val Leu Tyr Val Leu Leu Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
            35                  40                  45

Ser Val Asn Leu Leu Glu Asp Lys His Asn Gly Lys Leu Cys Lys Leu
50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
                100                 105                 110

Gly Asp Phe Ile Asp Tyr Glu Glu Leu Arg Glu Gln Leu Ser Ser Val
            115                 120                 125

Ser Ser Phe Glu Arg Phe Glu Ile Phe Pro Lys Thr Ser Ser Trp Pro
130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Glu Gly Met Ile
                165                 170                 175

Asp Tyr Glu Gly Thr Gly Gln Ala Ala Tyr Pro Lys Leu Ser Lys Ser
            180                 185                 190

Tyr Ile Asn Asp Lys Gly Lys Glu Val Leu Val Leu Trp Gly Ile His
            195                 200                 205

His Pro Ser Thr Ser Ala Asp Gln Gln Ser Leu Tyr Gln Asn Ala Asp
210                 215                 220

Ala Tyr Val Phe Val Gly Ser Ser Arg Tyr Ser Lys Lys Phe Lys Pro
225                 230                 235                 240

Glu Ile Ala Ile Arg Pro Lys Val Arg Asp Gln Glu Gly Arg Met Asn
                245                 250                 255

Tyr Tyr Trp Thr Leu Val Glu Pro Gly Asp Lys Ile Thr Phe Glu Ala
            260                 265                 270

Thr Gly Asn Leu Val Val Pro Arg Tyr Ala Phe Ala Met Glu Arg Asn
            275                 280                 285

Ala Gly Ser Gly Ile Ile Ile Ser Asp Thr Pro Val His Asp Cys Asn
290                 295                 300

Thr Thr Cys Gln Thr Pro Lys Gly Ala Ile Asn Thr Ser Leu Pro Phe
305                 310                 315                 320

Gln Asn Ile His Pro Ile Thr Ile Gly Lys Cys Pro Lys Tyr Val Lys
                325                 330                 335

Ser Thr Lys Leu Arg Leu Ala Thr Gly Leu Arg Asn Ser Pro Glu Asn
            340                 345                 350

Leu Tyr Phe Gln Gly Leu Phe Gly Ala Ile Ala Gly Phe Ile Glu Gly
            355                 360                 365

Gly Trp Thr Gly Met Val Asp Gly Trp Tyr Gly Tyr His His Gln Asn
370                 375                 380

Glu Gln Gly Ser Gly Tyr Ala Ala Asp Leu Lys Ser Thr Gln Asn Ala
385                 390                 395                 400

Ile Asp Glu Ile Thr Asn Lys Val Asn Ser Val Ile Glu Lys Met Asn
                405                 410                 415
```

```
Thr Gln Phe Thr Ala Val Gly Lys Glu Phe Asn His Leu Glu Lys Arg
            420                 425                 430

Ile Glu Asn Leu Asn Lys Lys Val Asp Asp Gly Phe Leu Asp Ile Trp
        435                 440                 445

Thr Tyr Asn Ala Glu Leu Leu Val Leu Leu Glu Asn Glu Arg Thr Leu
    450                 455                 460

Asp Tyr His Asp Ser Asn Val Lys Asn Leu Tyr Glu Lys Val Arg Ser
465                 470                 475                 480

Gln Leu Lys Asn Asn Ala Lys Glu Ile Gly Asn Gly Cys Phe Glu Phe
                485                 490                 495

Tyr His Lys Cys Asp Asn Thr Cys Met Glu Ser Val Lys Asn Gly Thr
                500                 505                 510

Tyr Asp Tyr Pro Lys Tyr Ser Glu Glu Ala Lys Leu Asn Arg Glu Glu
            515                 520                 525

Ile Asp Gly Val Lys Leu Glu Ser Thr Arg Ile Tyr Gln Gly Ala Glu
        530                 535                 540

Asn Leu Tyr Phe Gln Gly Gly Ser Gly Tyr Ile Pro Glu Ala Pro Arg
545                 550                 555                 560

Asp Gly Gln Ala Tyr Val Arg Lys Asp Gly Glu Trp Val Leu Leu Ser
                565                 570                 575

Thr Phe Leu Gly His His His His His His His His
                580                 585                 590
```

```
<210> SEQ ID NO 32
<211> LENGTH: 1785
<212> TYPE: DNA
<213> ORGANISM: Artificial Sequence
<220> FEATURE:
<223> OTHER INFORMATION: Synthetic

<400> SEQUENCE: 32
ccatggtaag cgctattgtt ttatatgtgc ttttggcggc ggcggcgcat tctgcctttg      60
cggatacact gtgtattggc taccacgcca acaatagcac cgataccgtg gatacagtgc     120
tggagaagaa tgtgaccgtg acccactctg tgaatctgct ggaggataag cacaatggca     180
agctgtgtaa gctgagagga gttgcccctc tgcacctggg caaatgtaat attgccggct     240
ggattctggg aaatcctgaa tgtgaaagcc tgtctacagc cagcagctgg tcttatatcg     300
tggaaacccc tagcagcgac aatggcacct gttaccctgg cgacttcatc gattacgagg     360
agctgagaga acagctgtct agcgtgtcca gcttcgagag attcgagatc ttccctaaga     420
caagcagctg gcctaatcac gattctaata agggagtgac agccgcctgt cctcatgccg     480
gagccaagtc cttttacaag aacctgatct ggctggtgga aggcatgatt gattacgaag     540
gcacaggcca ggcagcctac cctaagctgt ctaagagcta catcaacgac aagggcaaag     600
aagtgctggt gctgtgggga atccaccacc ctagcacaag cgccgatcag cagagcctgt     660
accagaatgc cgatgcctat gtgtttgtgg gcagcagcag atacagcaaa aagttcaagc     720
ctgaaattgc cattagaccc aaagtgagag atcaggaagg cagaatgaat tactactgga     780
ccctggtgga acctggcgat aagatcacat ttgaggccac cggaaatctg gtggtgccta     840
gatatgcatt tgctatggag agaaatgctg gctctggcat cattatctct gatacccctg     900
tgcacgactg taataccacc tgtcagacac taagggcgc cattaatacc agcctgccct     960
tccagaatat tcaccctatc accatcggca agtgtcctaa gtatgtgaag agcaccaagc    1020
tgagactggc taccggtctg agaaatagcc ctgaaaacct gtattttcaa ggcctgtttg    1080
```

-continued

```
gagccatcgc cggctttatt gagggaggat ggaccggaat ggtggatggc tggtacggct   1140
atcaccacca gaatgagcag ggatccggat atgccgccga tctgaagtct acacagaacg   1200
ccatcgacga gatcacaaac aaggtgaaca gcgtgatcga gaagatgaac acccagttta   1260
cagctgtggg caaggagttc aaccacctgg agaagagaat cgagaacctg aacaagaaag   1320
tggacgacgg cttcctggat atttggacct acaatgccga gctgctcgtg ctcctggaga   1380
atgagagaac cctggactac cacgacagca atgtgaagaa cctgtacgag aaggtgagaa   1440
gccagctgaa gaacaatgcc aaggagatcg caacggctg ctttgagttc taccacaagt    1500
gtgacaaaca ctgtatggag tctgtgaaga acggcaccta cgactaccct aagtatagcg   1560
aggaggccaa gctgaataga gaggagatcg acggcgtgaa actggaaagc aagaatct    1620 atcagggcgc tgaaaacctg tatttcagg gcggttctgg ttacatcccg gaagctccgc   1680
gtgacggtca ggcttacgtt cgtaaagacg gtgaatgggt tctgctgtct accttcctgg   1740
gtcaccatca tcaccaccat caccatcatc actgataaaa agctt                   1785
```

<210> SEQ ID NO 33
<211> LENGTH: 591
<212> TYPE: PRT
<213> ORGANISM: Artificial Sequence
<220> FEATURE:
<223> OTHER INFORMATION: Synthetic

<400> SEQUENCE: 33

```
Met Val Ser Ala Ile Val Leu Tyr Val Leu Leu Ala Ala Ala Ala His
1               5                   10                  15

Ser Ala Phe Ala Asp Thr Leu Cys Ile Gly Tyr His Ala Asn Asn Ser
                20                  25                  30

Thr Asp Thr Val Asp Thr Val Leu Glu Lys Asn Val Thr Val Thr His
            35                  40                  45

Ser Val Asn Leu Leu Glu Asp Lys His Asn Gly Lys Leu Cys Lys Leu
        50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Glu Gly Met Ile Asp Tyr
    130                 135                 140

Glu Gly Thr Gly Gln Ala Ala Trp Pro Asn His Asp Ser Asn Lys Gly
145                 150                 155                 160

Val Thr Ala Ala Cys Pro His Ala Gly Ala Lys Ser Phe Tyr Lys Asn
                165                 170                 175

Leu Ile Trp Leu Val Lys Lys Gly Asn Ser Tyr Pro Lys Leu Ser Lys
            180                 185                 190

Ser Tyr Ile Asn Asp Lys Gly Lys Glu Val Leu Val Leu Trp Gly Ile
        195                 200                 205

His His Pro Ser Thr Ser Ala Asp Gln Gln Ser Leu Tyr Gln Asn Ala
    210                 215                 220

Asp Ala Tyr Val Phe Val Gly Ser Ser Arg Tyr Ser Lys Lys Phe Lys
225                 230                 235                 240
```

Pro Glu Ile Ala Ile Arg Pro Lys Val Arg Asp Gln Glu Gly Arg Met
             245                 250                 255

Asn Tyr Tyr Trp Thr Leu Val Glu Pro Gly Asp Lys Ile Thr Phe Glu
            260                 265                 270

Ala Thr Gly Asn Leu Val Val Pro Arg Tyr Ala Phe Ala Met Glu Arg
            275                 280                 285

Asn Ala Gly Ser Gly Ile Ile Ile Ser Asp Thr Pro Val His Asp Cys
        290                 295                 300

Asn Thr Thr Cys Gln Thr Pro Lys Gly Ala Ile Asn Thr Ser Leu Pro
305                 310                 315                 320

Phe Gln Asn Ile His Pro Ile Thr Ile Gly Lys Cys Pro Lys Tyr Val
                325                 330                 335

Lys Ser Thr Lys Leu Arg Leu Ala Thr Gly Leu Arg Asn Ser Pro Glu
            340                 345                 350

Asn Leu Tyr Phe Gln Gly Leu Phe Gly Ala Ile Ala Gly Phe Ile Glu
        355                 360                 365

Gly Gly Trp Thr Gly Met Val Asp Gly Trp Tyr Gly Tyr His His Gln
    370                 375                 380

Asn Glu Gln Gly Ser Gly Tyr Ala Ala Asp Leu Lys Ser Thr Gln Asn
385                 390                 395                 400

Ala Ile Asp Glu Ile Thr Asn Lys Val Asn Ser Val Ile Glu Lys Met
                405                 410                 415

Asn Thr Gln Phe Thr Ala Val Gly Lys Glu Phe Asn His Leu Glu Lys
            420                 425                 430

Arg Ile Glu Asn Leu Asn Lys Lys Val Asp Asp Gly Phe Leu Asp Ile
        435                 440                 445

Trp Thr Tyr Asn Ala Glu Leu Leu Val Leu Leu Glu Asn Glu Arg Thr
    450                 455                 460

Leu Asp Tyr His Asp Ser Asn Val Lys Asn Leu Tyr Glu Lys Val Arg
465                 470                 475                 480

Ser Gln Leu Lys Asn Asn Ala Lys Glu Ile Gly Asn Gly Cys Phe Glu
                485                 490                 495

Phe Tyr His Lys Cys Asp Asn Thr Cys Met Glu Ser Val Lys Asn Gly
            500                 505                 510

Thr Tyr Asp Tyr Pro Lys Tyr Ser Glu Glu Ala Lys Leu Asn Arg Glu
        515                 520                 525

Glu Ile Asp Gly Val Lys Leu Glu Ser Thr Arg Ile Tyr Gln Gly Ala
    530                 535                 540

Glu Asn Leu Tyr Phe Gln Gly Gly Ser Gly Tyr Ile Pro Glu Ala Pro
545                 550                 555                 560

Arg Asp Gly Gln Ala Tyr Val Arg Lys Asp Gly Glu Trp Val Leu Leu
                565                 570                 575

Ser Thr Phe Leu Gly His His His His His His His His
            580                 585                 590

<210> SEQ ID NO 34
<211> LENGTH: 1787
<212> TYPE: DNA
<213> ORGANISM: Artificial Sequence
<220> FEATURE:
<223> OTHER INFORMATION: Synthetic

<400> SEQUENCE: 34
ccatggtaag cgctattgtt ttatatgtgc ttttggcggc ggcggcgcat tctgcctttg      60

| | | | |
|---|---|---|---|
| cggatacact | gtgtattggc | taccacgcca | acaatagcac cgataccgtg gatacagtgc | 120 |
| tggagaagaa | tgtgaccgtg | acccactctg | tgaatctgct ggaggataag cacaatggca | 180 |
| agctgtgtaa | gctgagagga | gttgcccctc | tgcacctggg caaatgtaat attgccggct | 240 |
| ggattctggg | aaatcctgaa | tgtgaaagcc | tgtctacagc cagcagctgg tcttatatcg | 300 |
| tggaaacccc | tagcagcgac | aatggcacct | gttaccctgg cgacttcatc gattacgagg | 360 |
| agctgagaga | acagctgtct | agcgtgtcca | gcttcgagag attcgagatc ttccctgaag | 420 |
| gcatgattga | ttacgaaggc | acaggccagg | cagcctggcc taatcacgat tctaataagg | 480 |
| gagtgacagc | cgcctgtcct | catgccggag | ccaagtcctt ttacaagaac ctgatctggc | 540 |
| tggtgaagaa | gggcaacagc | taccctaagc | tgtctaagag ctacatcaac gacaagggca | 600 |
| aagaagtgct | ggtgctgtgg | ggaatccacc | accctagcac aagcgccgat cagcagagcc | 660 |
| tgtaccagaa | tgccgatgcc | tatgtgtttg | tgggcagcag cagatacagc aaaaagttca | 720 |
| agcctgaaat | tgccattaga | cccaaagtga | gagatcagga aggcagaatg aattactact | 780 |
| ggaccctggt | ggaacctggc | gataagatca | catttgaggc caccggaaat ctggtggtgc | 840 |
| ctagatatgc | atttgctatg | gagagaaatg | ctggctctgg catcattatc tctgataccc | 900 |
| ctgtgcacga | ctgtaatacc | acctgtcaga | cacctaaggg cgccattaat accagcctgc | 960 |
| ccttccagaa | tattcaccct | atcaccatcg | gcaagtgtcc taagtatgtg aagagcacca | 1020 |
| agctgagact | ggctaccggt | ctgagaaata | gccctgaaaa cctgtatttt caaggcctgt | 1080 |
| ttggagccat | cgccggcttt | attgagggag | gatggaccgg aatggtggat ggctggtacg | 1140 |
| gctatcacca | ccagaatgag | cagggatccg | gatatgccgc cgatctgaag tctacacaga | 1200 |
| acgccatcga | cgagatcaca | aacaaggtga | acagcgtgat cgagaagatg aacacccagt | 1260 |
| ttacagctgt | gggcaaggag | ttcaaccacc | tggagaagag aatcgagaac ctgaacaaga | 1320 |
| aagtggacga | cggcttcctg | gatatttgga | cctacaatgc cgagctgctc gtgctcctgg | 1380 |
| agaatgagag | aaccctggac | taccacgaca | gcaatgtgaa gaacctgtac gagaaggtga | 1440 |
| gaagccagct | gaagaacaat | gccaaggaga | tcggcaacgg ctgctttgag ttctaccaca | 1500 |
| agtgtgacaa | cacctgtatg | gagtctgtga | agaacggcac ctacgactac cctaagtata | 1560 |
| gcgaggaggc | caagctgaat | agagaggaga | tcgacggcgt gaaactggaa agcacaagaa | 1620 |
| tctatcaggg | cgctgaaaac | ctgtattttc | agggcggttc tggttacatc ccggaagctc | 1680 |
| cgcgtgacgg | tcaggcttac | gttcgtaaag | acggtgaatg ggttctgctg tctaccttcc | 1740 |
| tgggtcacca | tcatcaccac | catcaccatc | atcactgata aaagctt | 1787 |

<210> SEQ ID NO 35
<211> LENGTH: 586
<212> TYPE: PRT
<213> ORGANISM: Artificial Sequence
<220> FEATURE:
<223> OTHER INFORMATION: Synthetic

<400> SEQUENCE: 35

```
Met Val Ser Ala Ile Val Leu Tyr Val Leu Leu Ala Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60
```

```
Arg Gly Val Ala Pro Leu His Leu Gly Lys Cys Asn Ile Ala Gly Trp
 65                  70                  75                  80

Ile Leu Gly Asn Pro Glu Cys Glu Ser Leu Ser Thr Ala Ser Ser Trp
                 85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Lys Thr Ser Ser Trp Pro
130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
                165                 170                 175

Ser Tyr Pro Lys Leu Ser Lys Ser Tyr Ile Asn Asp Lys Gly Lys Glu
            180                 185                 190

Val Leu Val Leu Trp Gly Ile His His Pro Ser Thr Ser Ala Asp Gln
        195                 200                 205

Gln Ser Leu Tyr Gln Asn Ala Asp Ala Tyr Val Phe Val Gly Ser Ser
210                 215                 220

Arg Tyr Ser Lys Lys Phe Lys Pro Glu Ile Ala Ile Gly Ile Phe Gly
225                 230                 235                 240

Ala Ile Ala Gly Phe Ile Glu Gly Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Ala Met Glu Arg Asn Ala Gly Ser Gly
        275                 280                 285

Ile Ile Ile Ser Asp Thr Pro Val His Asp Cys Asn Thr Thr Cys Gln
290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ser Pro Glu Asn Leu Tyr Phe Gln
            340                 345                 350

Gly Leu Phe Gly Ala Ile Ala Gly Phe Ile Glu Gly Gly Trp Thr Gly
        355                 360                 365

Met Val Asp Gly Trp Tyr Gly Tyr His His Gln Asn Glu Gln Gly Ser
        370                 375                 380

Gly Tyr Ala Ala Asp Leu Lys Ser Thr Gln Asn Ala Ile Asp Glu Ile
385                 390                 395                 400

Thr Asn Lys Val Asn Ser Val Ile Glu Lys Met Asn Thr Gln Phe Thr
                405                 410                 415

Ala Val Gly Lys Glu Phe Asn His Leu Glu Lys Arg Ile Glu Asn Leu
            420                 425                 430

Asn Lys Lys Val Asp Asp Gly Phe Leu Asp Ile Trp Thr Tyr Asn Ala
        435                 440                 445

Glu Leu Leu Val Leu Leu Glu Asn Glu Arg Thr Leu Asp Tyr His Asp
450                 455                 460

Ser Asn Val Lys Asn Leu Tyr Glu Lys Val Arg Ser Gln Leu Lys Asn
465                 470                 475                 480
```

```
Asn Ala Lys Glu Ile Gly Asn Gly Cys Phe Glu Tyr His Lys Cys
                485                 490                 495

Asp Asn Thr Cys Met Glu Ser Val Lys Asn Gly Thr Tyr Asp Tyr Pro
            500                 505                 510

Lys Tyr Ser Glu Glu Ala Lys Leu Asn Arg Glu Glu Ile Asp Gly Val
        515                 520                 525

Lys Leu Glu Ser Thr Arg Ile Tyr Gln Gly Ala Glu Asn Leu Tyr Phe
    530                 535                 540

Gln Gly Gly Ser Gly Tyr Ile Pro Glu Ala Pro Arg Asp Gly Gln Ala
545                 550                 555                 560

Tyr Val Arg Lys Asp Gly Glu Trp Val Leu Leu Ser Thr Phe Leu Gly
                565                 570                 575

His His His His His His His His His
            580                 585

<210> SEQ ID NO 36
<211> LENGTH: 12
<212> TYPE: PRT
<213> ORGANISM: Artificial Sequence
<220> FEATURE:
<223> OTHER INFORMATION: Synthetic

<400> SEQUENCE: 36

Gly Ile Phe Gly Ala Ile Ala Gly Phe Ile Glu Gly
1               5                   10

<210> SEQ ID NO 37
<211> LENGTH: 1772
<212> TYPE: DNA
<213> ORGANISM: Artificial Sequence
<220> FEATURE:
<223> OTHER INFORMATION: Synthetic

<400> SEQUENCE: 37
ccatggtaag cgctattgtt ttatatgtgc ttttggcggc ggcggcgcat tctgcctttg      60
cggatacact gtgtattggc taccacgcca acaatagcac cgataccgtg atacagtgc     120
tggagaagaa tgtgaccgtg acccactctg tgaatctgct ggaggataag cacaatggca    180
agctgtgtaa gctgagagga gttgcccctc tgcacctggg caaatgtaat attgccggct    240
ggattctggg aaatcctgaa tgtgaaagcc tgtctacagc cagcagctgg tcttatatcg    300
tggaaacccc tagcagcgac aatggcacct gttaccctgg cgacttcatc gattacgagg    360
agctgagaga cagctgtctc agcgtgtcca gcttcgagag attcgagatc ttccctaaga    420
caagcagctg gcctaatcac gattctaata agggagtgac agccgcctgt cctcatgccg    480
gagccaagtc ctttttacaag aacctgatct ggctggtgaa gaagggcaac agctacccta    540
agctgtctaa gagctacatc aacgacaagg gcaaagaagt gctggtgctg tggggaatcc    600
accaccctag cacaagcgcc gatcagcaga gcctgtacca gaatgccgat gcctatgtgt    660
tgtgggcag cagcagatac agcaaaaagt tcaagcctga aattgccatt ggcattttcg    720
gcgctatcgc cggcttcatt gagggaggca gaatgaatta ctactggacc ctggtggaac    780
ctggcgataa gatcacattt gaggccaccg gaaatctggt ggtgcctaga tatgcatttg    840
ctatggagag aaatgctggc tctggcatca ttatctctga taccctgtg cacgactgta    900
ataccacctg tcagacacct aagggcgcca ttaataccag cctgccctte cagaatattc    960
acccatcac catcggcaag tgtcctaagt atgtgaagag caccaagctg agactggcta   1020
ccggtctgag aaatagccct gaaaacctgt attttcaagg cctgtttgga gccatcgccg   1080
```

-continued

```
gctttattga gggaggatgg accggaatgg tggatggctg gtacggctat caccaccaga      1140
atgagcaggg atccggatat gccgccgatc tgaagtctac acagaacgcc atcgacgaga      1200
tcacaaacaa ggtgaacagc gtgatcgaga agatgaacac ccagtttaca gctgtgggca      1260
aggagttcaa ccacctggag aagagaatcg agaacctgaa caagaaagtg acgacggct       1320 tcctggatat ttggacctac aatgccgagc tgctcgtgct cctggagaat gagagaaccc      1380
tggactacca cgacagcaat gtgaagaacc tgtacgagaa ggtgagaagc cagctgaaga      1440
acaatgccaa ggagatcggc aacggctgct ttgagttcta ccacaagtgt gacaacacct      1500
gtatggagtc tgtgaagaac ggcacctacg actaccctaa gtatagcgag gaggccaagc      1560
tgaatagaga ggagatcgac ggcgtgaaac tggaaagcac aagaatctat cagggcgctg      1620
aaaacctgta ttttcagggc ggttctggtt acatcccgga agctccgcgt gacggtcagg      1680
cttacgttcg taaagacggt gaatgggttc tgctgtctac cttcctgggt caccatcatc      1740
accaccatca ccatcatcac tgataaaagc tt                                    1772
```

<210> SEQ ID NO 38
<211> LENGTH: 588
<212> TYPE: PRT
<213> ORGANISM: Artificial Sequence
<220> FEATURE:
<223> OTHER INFORMATION: Synthetic

<400> SEQUENCE: 38

```
Met Val Ser Ala Ile Val Leu Tyr Val Leu Ala Ala Ala Ala His
1               5                   10                  15

Ser Ala Phe Ala Asp Thr Leu Cys Ile Gly Tyr His Ala Asn Asn Ser
                20                  25                  30

Thr Asp Thr Val Asp Thr Val Leu Glu Lys Asn Val Thr Val Thr His
            35                  40                  45

Ser Val Asn Leu Leu Glu Asp Lys His Asn Gly Lys Leu Cys Lys Leu
        50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Lys Thr Ser Ser Trp Pro
    130                 135                 140

Asn His Asp Ser Asn Lys Gly Val Thr Ala Ala Cys Pro Gly Ile Phe
145                 150                 155                 160

Gly Ala Ile Ala Gly Phe Ile Glu Gly Phe Tyr Lys Asn Leu Ile Trp
                165                 170                 175

Leu Val Lys Lys Gly Asn Ser Tyr Pro Lys Leu Ser Lys Ser Tyr Ile
            180                 185                 190

Asn Asp Lys Gly Lys Glu Val Leu Val Leu Trp Gly Ile His His Pro
        195                 200                 205

Ser Thr Ser Ala Asp Gln Gln Ser Leu Tyr Gln Asn Ala Asp Ala Tyr
    210                 215                 220

Val Phe Val Gly Ser Ser Arg Tyr Ser Lys Lys Phe Lys Pro Glu Ile
225                 230                 235                 240
```

Ala Ile Arg Pro Lys Val Arg Asp Gln Glu Gly Arg Met Asn Tyr Tyr
            245                 250                 255

Trp Thr Leu Val Glu Pro Gly Asp Lys Ile Thr Phe Glu Ala Thr Gly
        260                 265                 270

Asn Leu Val Val Pro Arg Tyr Ala Phe Ala Met Glu Arg Asn Ala Gly
    275                 280                 285

Ser Gly Ile Ile Ile Ser Asp Thr Pro Val His Asp Cys Asn Thr Thr
290                 295                 300

Cys Gln Thr Pro Lys Gly Ala Ile Asn Thr Ser Leu Pro Phe Gln Asn
305                 310                 315                 320

Ile His Pro Ile Thr Ile Gly Lys Cys Pro Lys Tyr Val Lys Ser Thr
                325                 330                 335

Lys Leu Arg Leu Ala Thr Gly Leu Arg Asn Ser Pro Glu Asn Leu Tyr
            340                 345                 350

Phe Gln Gly Leu Phe Gly Ala Ile Ala Gly Phe Ile Glu Gly Gly Trp
        355                 360                 365

Thr Gly Met Val Asp Gly Trp Tyr Gly Tyr His His Gln Asn Glu Gln
    370                 375                 380

Gly Ser Gly Tyr Ala Ala Asp Leu Lys Ser Thr Gln Asn Ala Ile Asp
385                 390                 395                 400

Glu Ile Thr Asn Lys Val Asn Ser Val Ile Glu Lys Met Asn Thr Gln
                405                 410                 415

Phe Thr Ala Val Gly Lys Glu Phe Asn His Leu Glu Lys Arg Ile Glu
            420                 425                 430

Asn Leu Asn Lys Lys Val Asp Asp Gly Phe Leu Asp Ile Trp Thr Tyr
        435                 440                 445

Asn Ala Glu Leu Leu Val Leu Leu Glu Asn Glu Arg Thr Leu Asp Tyr
    450                 455                 460

His Asp Ser Asn Val Lys Asn Leu Tyr Glu Lys Val Arg Ser Gln Leu
465                 470                 475                 480

Lys Asn Asn Ala Lys Glu Ile Gly Asn Gly Cys Phe Glu Phe Tyr His
                485                 490                 495

Lys Cys Asp Asn Thr Cys Met Glu Ser Val Lys Asn Gly Thr Tyr Asp
            500                 505                 510

Tyr Pro Lys Tyr Ser Glu Glu Ala Lys Leu Asn Arg Glu Glu Ile Asp
        515                 520                 525

Gly Val Lys Leu Glu Ser Thr Arg Ile Tyr Gln Gly Ala Glu Asn Leu
    530                 535                 540

Tyr Phe Gln Gly Gly Ser Gly Tyr Ile Pro Glu Ala Pro Arg Asp Gly
545                 550                 555                 560

Gln Ala Tyr Val Arg Lys Asp Gly Glu Trp Val Leu Leu Ser Thr Phe
                565                 570                 575

Leu Gly His His His His His His His His
            580                 585

<210> SEQ ID NO 39
<211> LENGTH: 1778
<212> TYPE: DNA
<213> ORGANISM: Artificial Sequence
<220> FEATURE:
<223> OTHER INFORMATION: Synthetic

<400> SEQUENCE: 39
ccatggtaag cgctattgtt ttatatgtgc ttttggcggc ggcggcgcat tctgcctttg      60

| | | |
|---|---|---|
| cggatacact gtgtattggc taccacgcca acaatagcac cgataccgtg gatacagtgc | 120 |
| tggagaagaa tgtgaccgtg acccactctg tgaatctgct ggaggataag cacaatggca | 180 |
| agctgtgtaa gctgagagga gttgcccctc tgcacctggg caaatgtaat attgccggct | 240 |
| ggattctggg aaatcctgaa tgtgaaagcc tgtctacagc cagcagctgg tcttatatcg | 300 |
| tggaaacccc tagcagcgac aatggcacct gttaccctgg cgacttcatc gattacgagg | 360 |
| agctgagaga acagctgtct agcgtgtcca gcttcgagag attcgagatc ttccctaaga | 420 |
| caagcagctg gcctaatcac gattctaata agggagtgac agccgcctgt cctggcattt | 480 |
| tcggcgctat cgccggcttc attgagggat tttacaagaa cctgatctgg ctggtgaaga | 540 |
| agggcaacag ctaccctaag ctgtctaaga gctacatcaa cgacaagggc aaagaagtgc | 600 |
| tggtgctgtg gggaatccac caccctagca agcgccga tcagcagagc ctgtaccaga | 660 |
| atgccgatgc ctatgtgttt gtgggcagca gcagatacag caaaaagttc aagcctgaaa | 720 |
| ttgccattag acccaaagtg agagatcagg aaggcagaat gaattactac tggaccctgg | 780 |
| tggaacctgg cgataagatc acatttgagg ccaccggaaa tctggtggtg cctagatatg | 840 |
| catttgctat ggagagaaat gctggctctg gcatcattat ctctgatacc cctgtgcacg | 900 |
| actgtaatac cacctgtcag acacctaagg gcgccattaa taccagcctg cccttccaga | 960 |
| atattcaccc tatccaccat cggcaagtgtc ctaagtatgt gaagagcacc aagctgagac | 1020 |
| tggctaccgg tctgagaaat agccctgaaa acctgtattt tcaaggcctg tttggagcca | 1080 |
| tcgccggctt tattgaggga ggatggaccg gaatggtgga tggctggtac ggctatcacc | 1140 |
| accagaatga gcagggatcc ggatatgccg ccgatctgaa gtctacacag aacgccatcg | 1200 |
| acgagatcac aaacaaggtg aacagcgtga tcgagaagat gaacacccag tttacagctg | 1260 |
| tgggcaagga gttcaaccac ctggagaaga aatcgagaa cctgaacaag aaagtggacg | 1320 |
| acggcttcct ggatatttgg acctacaatg ccgagctgct cgtgctcctg gagaatgaga | 1380 |
| gaaccctgga ctaccacgac agcaatgtga agaacctgta cgagaaggtg agaagccagc | 1440 |
| tgaagaacaa tgccaaggag atcggcaacg gctgctttga gttctaccac aagtgtgaca | 1500 |
| acacctgtat ggagtctgtg aagaacggca cctacgacta ccctaagtat agcgaggagg | 1560 |
| ccaagctgaa tagagaggag atcgacggcg tgaaactgga aagcacaaga atctatcagg | 1620 |
| gcgctgaaaa cctgtatttt cagggcggtt ctggttacat cccggaagct ccgcgtgacg | 1680 |
| gtcaggctta cgttcgtaaa gacggtgaat gggttctgct gtctaccttc ctgggtcacc | 1740 |
| atcatcacca ccatcaccat catcactgat aaaagctt | 1778 |

<210> SEQ ID NO 40
<211> LENGTH: 589
<212> TYPE: PRT
<213> ORGANISM: Artificial Sequence
<220> FEATURE:
<223> OTHER INFORMATION: Synthetic

<400> SEQUENCE: 40

Met Val Ser Ala Ile Val Leu Tyr Val Leu Leu Ala Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

```
Arg Gly Val Ala Pro Leu His Leu Gly Lys Cys Asn Ile Ala Gly Trp
 65                  70                  75                  80

Ile Leu Gly Asn Pro Glu Cys Glu Ser Leu Ser Thr Ala Ser Ser Trp
                 85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
            115                 120                 125

Ser Ser Phe Glu Arg Phe Glu Ile Phe Pro Lys Thr Ser Ser Trp Pro
        130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Gly Ile Phe Gly
                165                 170                 175

Ala Ile Ala Gly Phe Ile Glu Gly Tyr Pro Lys Leu Ser Lys Ser Tyr
            180                 185                 190

Ile Asn Asp Lys Gly Lys Glu Val Leu Val Leu Trp Gly Ile His His
            195                 200                 205

Pro Ser Thr Ser Ala Asp Gln Gln Ser Leu Tyr Gln Asn Ala Asp Ala
        210                 215                 220

Tyr Val Phe Val Gly Ser Ser Arg Tyr Ser Lys Lys Phe Lys Pro Glu
225                 230                 235                 240

Ile Ala Ile Arg Pro Lys Val Arg Asp Gln Glu Gly Arg Met Asn Tyr
                245                 250                 255

Tyr Trp Thr Leu Val Glu Pro Gly Asp Lys Ile Thr Phe Glu Ala Thr
            260                 265                 270

Gly Asn Leu Val Val Pro Arg Tyr Ala Phe Ala Met Glu Arg Asn Ala
            275                 280                 285

Gly Ser Gly Ile Ile Ile Ser Asp Thr Pro Val His Asp Cys Asn Thr
        290                 295                 300

Thr Cys Gln Thr Pro Lys Gly Ala Ile Asn Thr Ser Leu Pro Phe Gln
305                 310                 315                 320

Asn Ile His Pro Ile Thr Ile Gly Lys Cys Pro Lys Tyr Val Lys Ser
                325                 330                 335

Thr Lys Leu Arg Leu Ala Thr Gly Leu Arg Asn Ser Pro Glu Asn Leu
            340                 345                 350

Tyr Phe Gln Gly Leu Phe Gly Ala Ile Ala Gly Phe Ile Glu Gly Gly
        355                 360                 365

Trp Thr Gly Met Val Asp Gly Trp Tyr Gly Tyr His His Gln Asn Glu
        370                 375                 380

Gln Gly Ser Gly Tyr Ala Ala Asp Leu Lys Ser Thr Gln Asn Ala Ile
385                 390                 395                 400

Asp Glu Ile Thr Asn Lys Val Asn Ser Val Ile Glu Lys Met Asn Thr
                405                 410                 415

Gln Phe Thr Ala Val Gly Lys Glu Phe Asn His Leu Glu Lys Arg Ile
            420                 425                 430

Glu Asn Leu Asn Lys Lys Val Asp Asp Gly Phe Leu Asp Ile Trp Thr
        435                 440                 445

Tyr Asn Ala Glu Leu Leu Val Leu Leu Glu Asn Glu Arg Thr Leu Asp
        450                 455                 460

Tyr His Asp Ser Asn Val Lys Asn Leu Tyr Glu Lys Val Arg Ser Gln
465                 470                 475                 480
```

```
Leu Lys Asn Asn Ala Lys Glu Ile Gly Asn Gly Cys Phe Glu Phe Tyr
                485                 490                 495
His Lys Cys Asp Asn Thr Cys Met Glu Ser Val Lys Asn Gly Thr Tyr
            500                 505                 510
Asp Tyr Pro Lys Tyr Ser Glu Glu Ala Lys Leu Asn Arg Glu Glu Ile
            515                 520                 525
Asp Gly Val Lys Leu Glu Ser Thr Arg Ile Tyr Gln Gly Ala Glu Asn
        530                 535                 540
Leu Tyr Phe Gln Gly Gly Ser Gly Tyr Ile Pro Glu Ala Pro Arg Asp
545                 550                 555                 560
Gly Gln Ala Tyr Val Arg Lys Asp Gly Glu Trp Val Leu Leu Ser Thr
                565                 570                 575
Phe Leu Gly His His His His His His His His
            580                 585
```

<210> SEQ ID NO 41
<211> LENGTH: 1781
<212> TYPE: DNA
<213> ORGANISM: Artificial Sequence
<220> FEATURE:
<223> OTHER INFORMATION: Synthetic

<400> SEQUENCE: 41

```
ccatggtaag cgctattgtt ttatatgtgc ttttggcggc ggcggcgcat tctgcctttg    60
cggatacact gtgtattggc taccacgcca acaatagcac cgataccgtg atacagtgc   120
tggagaagaa tgtgaccgtg acccactctg tgaatctgct ggaggataag cacaatggca   180
agctgtgtaa gctgagagga gttgcccctc tgcacctggg caaatgtaat attgccggct   240
ggattctggg aaatcctgaa tgtgaaagcc tgtctacagc cagcagctgg tcttatatcg   300
tggaaacccc tagcagcgac aatggcacct gttaccctgg cgacttcatc gattacgagg   360
agctgagaga cagctgtctg cgcgtgtcca gcttcgagag attcgagatc ttccctaaga   420
caagcagctg gcctaatcac gattctaata agggagtgac agccgcctgt cctcatgccg   480
gagccaagtc cttttacaag aacctgatct ggctggtggg cattttcggc gctatcgccg   540
gcttcattga gggataccct aagctgtcta agagctacaa caacgacaag ggcaagaag   600
tgctggtgct gtggggaatc caccacccta gcacaagcgc cgatcagcag agcctgtacc   660
agaatgccga tgcctatgtg tttgtgggca gcagcagata cagcaaaaag ttcaagcctg   720
aaattgccat tagacccaaa gtgagagatc aggaaggcag aatgaattac tactggaccc   780
tggtggaacc tggcgataag atcacatttg aggccaccgg aaatctggtg gtgcctagat   840
atgcatttgc tatggagaga aatgctggct ctggcatcat tatctctgat accctgtgc   900
acgactgtaa taccacctgt cagacaccta agggcgccta ataccagc tgcccttcc    960
agaatattca ccctatcacc atcggcaagt gtcctaagta tgtgaagagc accaagctga  1020
gactggctac cggtctgaga aatagccctg aaaacctgta ttttcaaggc tgtttggag  1080
ccatcgccgg ctttattgag ggaggatgga ccggaatggt ggatggctgg tacggctatc  1140
accaccagaa tgagcaggga tccggatatg ccgccgatct gaagtctaca cagaacgcca  1200
tcgacgagat cacaaacaag gtgaacgcg tgatcgagaa gatgaacacc cagtttacag  1260
ctgtgggcaa ggagttcaac cacctggaga gagaatcga gaacctgaac aagaaagtgg  1320
acgacggctt cctggatatt tggacctaca atgccgagct gctcgtgctc ctggagaatg  1380
agagaaccct ggactaccac gacagcaatg tgaagaacct gtacgagaag gtgagaagcc  1440
```

-continued

```
agctgaagaa caatgccaag gagatcggca acggctgctt tgagttctac cacaagtgtg    1500
acaacacctg tatggagtct gtgaagaacg gcacctacga ctaccctaag tatagcgagg    1560
aggccaagct gaatagagag gagatcgacg gcgtgaaact ggaaagcaca agaatctatc    1620
agggcgctga aaacctgtat tttcagggcg gttctggtta catcccggaa gctccgcgtg    1680
acggtcaggc ttacgttcgt aaagacggtg aatgggttct gctgtctacc ttcctgggtc    1740
accatcatca ccaccatcac catcatcact gataaaagct t                        1781
```

<210> SEQ ID NO 42
<211> LENGTH: 590
<212> TYPE: PRT
<213> ORGANISM: Artificial Sequence
<220> FEATURE:
<223> OTHER INFORMATION: Synthetic

<400> SEQUENCE: 42

```
Met Val Ser Ala Ile Val Leu Tyr Val Leu Leu Ala Ala Ala Ala His
 1               5                  10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
           100                 105                 110

Gly Asp Phe Ile Asp Tyr Glu Glu Leu Arg Glu Gln Leu Ser Ser Val
       115                 120                 125

Ser Ser Phe Glu Arg Phe Glu Ile Phe Pro Gly Ile Phe Gly Ala Ile
   130                 135                 140

Ala Gly Phe Ile Glu Gly Trp Pro Asn His Asp Ser Asn Lys Gly Val
145                 150                 155                 160

Thr Ala Ala Cys Pro His Ala Gly Ala Lys Ser Phe Tyr Lys Asn Leu
                165                 170                 175

Ile Trp Leu Val Lys Lys Gly Asn Ser Tyr Pro Lys Leu Ser Lys Ser
            180                 185                 190

Tyr Ile Asn Asp Lys Gly Lys Glu Val Leu Val Leu Trp Gly Ile His
        195                 200                 205

His Pro Ser Thr Ser Ala Asp Gln Gln Ser Leu Tyr Gln Asn Ala Asp
    210                 215                 220

Ala Tyr Val Phe Val Gly Ser Ser Arg Tyr Ser Lys Lys Phe Lys Pro
225                 230                 235                 240

Glu Ile Ala Ile Arg Pro Lys Val Arg Asp Gln Glu Gly Arg Met Asn
                245                 250                 255

Tyr Tyr Trp Thr Leu Val Glu Pro Gly Asp Lys Ile Thr Phe Glu Ala
            260                 265                 270

Thr Gly Asn Leu Val Val Pro Arg Tyr Ala Phe Ala Met Glu Arg Asn
        275                 280                 285

Ala Gly Ser Gly Ile Ile Ile Ser Asp Thr Pro Val His Asp Cys Asn
    290                 295                 300
```

Thr Thr Cys Gln Thr Pro Lys Gly Ala Ile Thr Ser Leu Pro Phe
305                 310                 315                 320

Gln Asn Ile His Pro Ile Thr Ile Gly Lys Cys Pro Tyr Val Lys
                325                 330                 335

Ser Thr Lys Leu Arg Leu Ala Thr Gly Leu Arg Asn Ser Pro Glu Asn
            340                 345                 350

Leu Tyr Phe Gln Gly Leu Phe Gly Ala Ile Ala Gly Phe Ile Glu Gly
        355                 360                 365

Gly Trp Thr Gly Met Val Asp Gly Trp Tyr Gly Tyr His His Gln Asn
370                 375                 380

Glu Gln Gly Ser Gly Tyr Ala Ala Asp Leu Lys Ser Thr Gln Asn Ala
385                 390                 395                 400

Ile Asp Glu Ile Thr Asn Lys Val Asn Ser Val Ile Glu Lys Met Asn
                405                 410                 415

Thr Gln Phe Thr Ala Val Gly Lys Glu Phe Asn His Leu Glu Lys Arg
            420                 425                 430

Ile Glu Asn Leu Asn Lys Lys Val Asp Asp Gly Phe Leu Asp Ile Trp
        435                 440                 445

Thr Tyr Asn Ala Glu Leu Leu Val Leu Leu Glu Asn Glu Arg Thr Leu
450                 455                 460

Asp Tyr His Asp Ser Asn Val Lys Asn Leu Tyr Glu Lys Val Arg Ser
465                 470                 475                 480

Gln Leu Lys Asn Asn Ala Lys Glu Ile Gly Asn Gly Cys Phe Glu Phe
                485                 490                 495

Tyr His Lys Cys Asp Asn Thr Cys Met Glu Ser Val Lys Asn Gly Thr
            500                 505                 510

Tyr Asp Tyr Pro Lys Tyr Ser Glu Glu Ala Lys Leu Asn Arg Glu Glu
        515                 520                 525

Ile Asp Gly Val Lys Leu Glu Ser Thr Arg Ile Tyr Gln Gly Ala Glu
530                 535                 540

Asn Leu Tyr Phe Gln Gly Gly Ser Gly Tyr Ile Pro Glu Ala Pro Arg
545                 550                 555                 560

Asp Gly Gln Ala Tyr Val Arg Lys Asp Gly Glu Trp Val Leu Leu Ser
                565                 570                 575

Thr Phe Leu Gly His His His His His His His His
            580                 585                 590

<210> SEQ ID NO 43
<211> LENGTH: 1784
<212> TYPE: DNA
<213> ORGANISM: Artificial Sequence
<220> FEATURE:
<223> OTHER INFORMATION: Synthetic

<400> SEQUENCE: 43
ccatggtaag cgctattgtt ttatatgtgc ttttggcggc ggcggcgcat tctgcctttg     60
cggatacact gtgtattggc taccacgcca acaatagcac cgataccgtg gatacagtgc    120
tggagaagaa tgtgaccgtg acccactctg tgaatctgct ggaggataag cacaatggca    180
agctgtgtaa gctgagagga gttgcccctc tgcacctggg caatgtaat attgccggct    240 ggattctggg aaatcctgaa tgtgaaagcc tgtctacagc cagcagctgg tcttatatcg    300
tggaaacccc tagcagcgac aatggcacct gttaccctgg cgacttcatc gattacgagg    360
agctgagaga acagctgtct agcgtgtcca gcttcgagag attcgagatc ttccctggca    420
ttttcggcgc tatcgccggc ttcattgagg atggcctaa tcacgattct aataagggag    480

```
tgacagccgc ctgtcctcat gccggagcca agtccttta caagaacctg atctggctgg        540
tgaagaaggg caacagctac cctaagctgt ctaagagcta catcaacgac aagggcaaag        600
aagtgctggt gctgtgggga atccaccacc ctagcacaag cgccgatcag cagagcctgt        660
accagaatgc cgatgcctat gtgtttgtgg cagcagcag atacagcaaa aagttcaagc         720
ctgaaattgc cattagaccc aaagtgagag atcaggaagg cagaatgaat tactactgga        780
ccctggtgga acctggcgat aagatcacat ttgaggccac cggaaatctg gtggtgccta        840
gatatgcatt tgctatggag agaaatgctg gctctggcat cattatctct gataccctg         900 tgcacgactg taataccacc tgtcagacac taagggcgc cattaatacc agcctgccct         960
tccagaatat tcaccctatc accatcggca agtgtcctaa gtatgtgaag agcaccaagc       1020
tgagactggc taccggtctg agaaatagcc tgaaaacct gtattttcaa ggcctgtttg        1080
gagccatcgc cggctttatt gagggaggat ggaccggaat ggtggatggc tggtacggct       1140
atcaccacca gaatgagcag ggatccggat atgccgccga tctgaagtct acacagaacg       1200
ccatcgacga gatcacaaac aaggtgaaca gcgtgatcga gaagatgaac acccagttta      1260
cagctgtggg caaggagttc aaccacctgg agaagagaat cgagaacctg aacaagaaag      1320
tggacgacgg cttcctggat atttggacct acaatgccga gctgctcgtg ctcctggaga      1380
atgagagaac cctggactac cacgacagca atgtgaagaa cctgtacgag aaggtgagaa      1440
gccagctgaa gaacaatgcc aaggagatcg gcaacggctg ctttgagttc taccacaagt      1500
gtgacaacac ctgtatggag tctgtgaaga acggcaccta cgactaccct aagtatagcg      1560
aggaggccaa gctgaataga gaggagatcg acggcgtgaa actggaaagc acaagaatct      1620
atcagggcgc tgaaaacctg tattttcagg gcggttctgg ttacatcccg gaagctccgc      1680
gtgacggtca ggcttacgtt cgtaaagacg gtgaatgggt tctgctgtct accttcctgg      1740
gtcaccatca tcaccaccat caccatcatc actgataaaa gctt                        1784
```

<210> SEQ ID NO 44
<211> LENGTH: 584
<212> TYPE: PRT
<213> ORGANISM: Artificial Sequence
<220> FEATURE:
<223> OTHER INFORMATION: Synthetic

<400> SEQUENCE: 44

```
Met Val Ser Ala Ile Val Leu Tyr Val Leu Leu Ala Ala Ala Ala His
1               5                   10                  15

Ser Ala Phe Ala Asp Thr Leu Cys Ile Gly Tyr His Ala Asn Asn Ser
                20                  25                  30

Thr Asp Thr Val Asp Thr Val Leu Glu Lys Asn Val Thr Val Thr His
            35                  40                  45

Ser Val Asn Leu Leu Glu Asp Lys His Asn Gly Lys Leu Cys Lys Leu
        50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
                100                 105                 110

Gly Asp Phe Ile Asp Tyr Glu Glu Leu Arg Glu Gln Leu Ser Ser Val
            115                 120                 125
```

-continued

```
Ser Ser Phe Glu Arg Phe Glu Ile Phe Pro Lys Thr Ser Ser Trp Pro
130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
                165                 170                 175

Ser Tyr Pro Lys Leu Ser Lys Ser Tyr Ile Asn Asp Lys Gly Lys Glu
                180                 185                 190

Val Leu Val Leu Trp Gly Ile His His Pro Ser Gly Ile Phe Gly Ala
            195                 200                 205

Ile Ala Gly Phe Ile Glu Gly Asp Ala Tyr Val Phe Val Gly Ser Ser
210                 215                 220

Arg Tyr Ser Lys Lys Phe Lys Pro Glu Ile Ala Ile Arg Pro Lys Val
225                 230                 235                 240

Arg Asp Gln Glu Gly Arg Met Asn Tyr Tyr Trp Thr Leu Val Glu Pro
                245                 250                 255

Gly Asp Lys Ile Thr Phe Glu Ala Thr Gly Asn Leu Val Val Pro Arg
                260                 265                 270

Tyr Ala Phe Ala Met Glu Arg Asn Ala Gly Ser Gly Ile Ile Ile Ser
            275                 280                 285

Asp Thr Pro Val His Asp Cys Asn Thr Thr Cys Gln Thr Pro Lys Gly
290                 295                 300

Ala Ile Asn Thr Ser Leu Pro Phe Gln Asn Ile His Pro Ile Thr Ile
305                 310                 315                 320

Gly Lys Cys Pro Lys Tyr Val Lys Ser Thr Lys Leu Arg Leu Ala Thr
                325                 330                 335

Gly Leu Arg Asn Ser Pro Gln Arg Glu Arg Arg Lys Lys Arg Gly Leu
                340                 345                 350

Phe Gly Ala Ile Ala Gly Phe Ile Glu Gly Gly Trp Thr Gly Met Val
            355                 360                 365

Asp Gly Trp Tyr Gly Tyr His His Gln Asn Glu Gln Gly Ser Gly Tyr
370                 375                 380

Ala Ala Asp Leu Lys Ser Thr Gln Asn Ala Ile Asp Glu Ile Thr Asn
385                 390                 395                 400

Lys Val Asn Ser Val Ile Glu Lys Met Asn Thr Gln Phe Thr Ala Val
                405                 410                 415

Gly Lys Glu Phe Asn His Leu Glu Lys Arg Ile Glu Asn Leu Asn Lys
                420                 425                 430

Lys Val Asp Asp Gly Phe Leu Asp Ile Trp Thr Tyr Asn Ala Glu Leu
            435                 440                 445

Leu Val Leu Leu Glu Asn Glu Arg Thr Leu Asp Tyr His Asp Ser Asn
450                 455                 460

Val Lys Asn Leu Tyr Glu Lys Val Arg Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Thr Cys Met Glu Ser Val Lys Asn Gly Thr Tyr Asp Tyr Pro Lys Tyr
                500                 505                 510

Ser Glu Glu Ala Lys Leu Asn Arg Glu Glu Ile Asp Gly Val Lys Leu
            515                 520                 525

Glu Ser Thr Arg Ile Tyr Gln Gly Ala Glu Asn Leu Tyr Phe Gln Gly
530                 535                 540

Gly Ser Gly Tyr Ile Pro Glu Ala Pro Arg Asp Gly Gln Ala Tyr Val
```

545                 550                 555                 560
Arg Lys Asp Gly Glu Trp Val Leu Leu Ser Thr Phe Leu Gly His His
                    565                 570                 575
His His His His His His His
            580

<210> SEQ ID NO 45
<211> LENGTH: 1766
<212> TYPE: DNA
<213> ORGANISM: Artificial Sequence
<220> FEATURE:
<223> OTHER INFORMATION: Synthetic

<400> SEQUENCE: 45

| | | |
|---|---|---|
| ccatggtaag cgctattgtt ttatatgtgc ttttggcggc ggcggcgcat tctgcctttg | 60 |
| cggatacact gtgtattggc taccacgcca acaatagcac cgataccgtg gatacagtgc | 120 |
| tggagaagaa tgtgaccgtg acccactctg tgaatctgct ggaggataag cacaatggca | 180 |
| agctgtgtaa gctgagagga gttgcccctc tgcacctggg caaatgtaat attgccggct | 240 |
| ggattctggg aaatcctgaa tgtgaaagcc tgtctacagc cagcagctgg tcttatatcg | 300 |
| tggaaacccc tagcagcgac aatggcacct gttaccctgg cgacttcatc gattacgagg | 360 |
| agctgagaga acagctgtct agcgtgtcca gcttcgagag attcgagatc ttccctaaga | 420 |
| caagcagctg gcctaatcac gattctaata agggagtgac agccgcctgt cctcatgccg | 480 |
| gagccaagtc cttttacaag aacctgatct ggctggtgaa gaagggcaac agctacccta | 540 |
| agctgtctaa gagctacatc aacgacaagg gcaaagaagt gctggtgctg tggggaatcc | 600 |
| accacccta_ cggcattttc ggcgctatcg ccggcttcat tgagggagat gcctatgtgt | 660 |
| tgtgggcag cagcagatac agcaaaaagt tcaagcctga aattgccatt agacccaaag | 720 |
| tgagagatca ggaaggcaga atgaattact actggaccct ggtggaacct ggcgataaga | 780 |
| tcacatttga ggccaccgga aatctggtgg tgcctagata tgcatttgct atggagagaa | 840 |
| atgctggctc tggcatcatt atctctgata cccctgtgca cgactgtaat accacctgtc | 900 |
| agacacctaa gggcgccatt aataccagcc tgcccttcca gaatattcac cctatcacca | 960 |
| tcggcaagtg tcctaagtat gtgaagagca ccaagctgag actggctacc ggtctgagaa | 1020 |
| atagccctca gagggagaga cgcaagaaga gaggcctgtt tggagccatc gccggcttta | 1080 |
| ttgagggagg atggaccgga atggtggatg gctggtacgg ctatcaccac cagaatgagc | 1140 |
| agggatccgg atatgccgcc gatctgaagt ctacacagaa cgccatcgac gagatcacaa | 1200 |
| acaaggtgaa cagcgtgatc gagaagatga acacccagtt tacagctgtg ggcaaggagt | 1260 |
| tcaaccacct ggagaagaga atcgagaacc tgaacaagaa agtggacgac ggcttcctgg | 1320 |
| atatttggac ctacaatgcc gagctgctcg tgctcctgga gaatgagaga accctggact | 1380 |
| accacgacag caatgtgaag aacctgtacg agaaggtgag aagccagctg aagaacaatg | 1440 |
| ccaaggagat cggcaacggc tgctttgagt tctaccacaa gtgtgacaac acctgtatgg | 1500 |
| agtctgtgaa gaacggcacc tacgactacc ctaagtatag cgaggaggcc aagctgaata | 1560 |
| gagaggagat cgacggcgtg aaactggaaa gcacaagaat ctatcagggc gctgaaaacc | 1620 |
| tgtattttca gggcggttct ggttacatcc cggaagctcc gcgtgacggt caggcttacg | 1680 |
| ttcgtaaaga cggtgaatgg gttctgctgt ctaccttcct gggtcaccat catcaccacc | 1740 |
| atcaccatca tcactgataa aagctt | 1766 |

<210> SEQ ID NO 46
<211> LENGTH: 584
<212> TYPE: PRT
<213> ORGANISM: Artificial Sequence
<220> FEATURE:
<223> OTHER INFORMATION: Synthetic

<400> SEQUENCE: 46

```
Met Val Ser Ala Ile Val Leu Tyr Val Leu Ala Ala Ala Ala His
1               5                   10                  15

Ser Ala Phe Ala Asp Thr Leu Cys Ile Gly Tyr His Ala Asn Asn
            20                  25                  30

Thr Asp Thr Val Asp Thr Val Leu Glu Lys Asn Val Thr Val Thr His
                35                  40                  45

Ser Val Asn Leu Leu Glu Asp Lys His Asn Gly Lys Leu Cys Lys Leu
50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Lys Thr Ser Ser Trp Pro
130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
                165                 170                 175

Ser Tyr Pro Lys Leu Ser Lys Ser Tyr Ile Asn Asp Lys Gly Lys Glu
            180                 185                 190

Val Leu Val Leu Trp Gly Ile His His Pro Ser Thr Ser Ala Asp Gln
        195                 200                 205

Gln Ser Leu Tyr Gln Asn Ala Asp Ala Tyr Val Phe Val Gly Ser Ser
210                 215                 220

Arg Tyr Ser Lys Lys Phe Lys Pro Gly Ile Phe Gly Ala Ile Ala Gly
225                 230                 235                 240

Phe Ile Glu Gly Gly Arg Met Asn Tyr Tyr Trp Thr Leu Val Glu Pro
                245                 250                 255

Gly Asp Lys Ile Thr Phe Glu Ala Thr Gly Asn Leu Val Val Pro Arg
            260                 265                 270

Tyr Ala Phe Ala Met Glu Arg Asn Ala Gly Ser Gly Ile Ile Ile Ser
        275                 280                 285

Asp Thr Pro Val His Asp Cys Asn Thr Thr Cys Gln Thr Pro Lys Gly
290                 295                 300

Ala Ile Asn Thr Ser Leu Pro Phe Gln Asn Ile His Pro Ile Thr Ile
305                 310                 315                 320

Gly Lys Cys Pro Lys Tyr Val Lys Ser Thr Lys Leu Arg Leu Ala Thr
                325                 330                 335

Gly Leu Arg Asn Ser Pro Gln Arg Glu Arg Arg Lys Lys Arg Gly Leu
            340                 345                 350

Phe Gly Ala Ile Ala Gly Phe Ile Glu Gly Gly Trp Thr Gly Met Val
        355                 360                 365

Asp Gly Trp Tyr Gly Tyr His His Gln Asn Glu Gln Gly Ser Gly Tyr
```

```
                370                 375                 380
Ala Ala Asp Leu Lys Ser Thr Gln Asn Ala Ile Asp Glu Ile Thr Asn
385                 390                 395                 400

Lys Val Asn Ser Val Ile Glu Lys Met Asn Thr Gln Phe Thr Ala Val
                405                 410                 415

Gly Lys Glu Phe Asn His Leu Glu Lys Arg Ile Glu Asn Leu Asn Lys
            420                 425                 430

Lys Val Asp Asp Gly Phe Leu Asp Ile Trp Thr Tyr Asn Ala Glu Leu
            435                 440                 445

Leu Val Leu Leu Glu Asn Glu Arg Thr Leu Asp Tyr His Asp Ser Asn
        450                 455                 460

Val Lys Asn Leu Tyr Glu Lys Val Arg Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Thr Cys Met Glu Ser Val Lys Asn Gly Thr Tyr Asp Tyr Pro Lys Tyr
            500                 505                 510

Ser Glu Glu Ala Lys Leu Asn Arg Glu Glu Ile Asp Gly Val Lys Leu
            515                 520                 525

Glu Ser Thr Arg Ile Tyr Gln Gly Ala Glu Asn Leu Tyr Phe Gln Gly
        530                 535                 540

Gly Ser Gly Tyr Ile Pro Glu Ala Pro Arg Asp Gly Gln Ala Tyr Val
545                 550                 555                 560

Arg Lys Asp Gly Glu Trp Val Leu Leu Ser Thr Phe Leu Gly His His
                565                 570                 575

His His His His His His
            580
```

<210> SEQ ID NO 47
<211> LENGTH: 1766
<212> TYPE: DNA
<213> ORGANISM: Artificial Sequence
<220> FEATURE:
<223> OTHER INFORMATION: Synthetic

<400> SEQUENCE: 47

```
ccatggtaag cgctattgtt ttatatgtgc ttttggcggc ggcggcgcat tctgcctttg      60
cggatacact gtgtattggc taccacgcca acaatagcac cgataccgtg gatacagtgc    120
tggagaagaa tgtgaccgtg acccactctg tgaatctgct ggaggataag cacaatggca    180
agctgtgtaa gctgagagga gttgcccctc tgcacctggg caaatgtaat attgccggct    240
ggattctggg aaatcctgaa tgtgaaagcc tgtctacagc cagcagctgg tcttatatcg    300
tggaaacccc tagcagcgac aatggcacct gttaccctgg cgacttcatc gattacgagg    360
agctgagaga acagctgtct agcgtgtcca gcttcgagag attcgagatc ttccctaaga    420
caagcagctg gcctaatcac gattctaata gggagtgac agccgcctgt cctcatgccg    480
gagccaagtc cttttacaag aacctgatct ggctggtgaa aagggcaac agctacccta    540
agctgtctaa gagctacatc aacgacaagg gcaaagaagt gctggtgctg tggggaatcc    600
accaccctag cacaagcgcc gatcagcaga gcctgtacca gaatgccgat gcctatgtgt    660
tgtgggcag cagcagatac agcaaaaagt tcaagcctgg catttcggc gctatcgccg    720
gcttcattga gggaggcaga atgaattact actggaccct ggtggaacct ggcgataaga    780
tcacatttga ggccaccgga aatctggtgg tgcctagata tgcatttgct atggagagaa    840
```

```
atgctggctc tggcatcatt atctctgata cccctgtgca cgactgtaat accacctgtc    900
agacacctaa gggcgccatt aataccagcc tgcccttcca gaatattcac cctatcacca    960
tcggcaagtg tcctaagtat gtgaagagca ccaagctgag actggctacc ggtctgagaa   1020
atagccctca gagggagaga cgcaagaaga gaggcctgtt tggagccatc gccggcttta   1080
ttgagggagg atggaccgga atggtggatg gctggtacgg ctatcaccac cagaatgagc   1140
agggatccgg atatgccgcc gatctgaagt ctacacagaa cgccatcgac gagatcacaa   1200
acaaggtgaa cagcgtgatc gagaagatga acacccagtt tacagctgtg ggcaaggagt   1260
tcaaccacct ggagaagaga atcgagaacc tgaacaagaa agtggacgac ggcttcctgg   1320
atatttggac ctacaatgcc gagctgctcg tgctcctgga gaatgagaga ccctggact    1380 accacgacag caatgtgaag aacctgtacg agaaggtgag aagccagctg aagaacaatg   1440
ccaaggagat cggcaacggc tgctttgagt tctaccacaa gtgtgacaac acctgtatgg   1500
agtctgtgaa gaacggcacc tacgactacc taagtatag cgaggaggcc aagctgaata   1560
gagaggagat cgacggcgtg aaactggaaa gcacaagaat ctatcagggc gctgaaaacc   1620
tgtattttca gggcggttct ggttacatcc cggaagctcc gcgtgacggt caggcttacg   1680
ttcgtaaaga cggtgaatgg gttctgctgt taccttcct gggtcaccat catcaccacc   1740
atcaccatca tcactgataa aagctt                                        1766
```

<210> SEQ ID NO 48
<211> LENGTH: 592
<212> TYPE: PRT
<213> ORGANISM: Artificial Sequence
<220> FEATURE:
<223> OTHER INFORMATION: Synthetic

<400> SEQUENCE: 48

```
Met Val Ser Ala Ile Val Leu Tyr Val Leu Leu Ala Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Lys Thr Ser Ser Trp Pro
    130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Arg Lys Lys Arg
                165                 170                 175

Gly Leu Phe Gly Ala Ile Ala Gly Phe Ile Glu Tyr Ile Asn Asp Lys
            180                 185                 190

Gly Lys Glu Val Leu Val Leu Trp Gly Ile His His Pro Ser Lys Glu
```

```
            195                 200                 205
Ser Thr Gln Lys Ala Ile Asp Gly Val Thr Asn Lys Val Asn Ser Asp
210                 215                 220

Ala Tyr Val Phe Val Gly Ser Ser Arg Tyr Ser Lys Lys Phe Lys Pro
225                 230                 235                 240

Glu Ile Ala Ile Arg Pro Lys Val Arg Asp Gln Glu Gly Arg Met Asn
                245                 250                 255

Tyr Tyr Trp Thr Leu Val Glu Pro Gly Asp Lys Ile Thr Phe Glu Ala
                260                 265                 270

Thr Gly Asn Leu Val Val Pro Arg Tyr Ala Phe Ala Met Glu Arg Asn
                275                 280                 285

Ala Gly Ser Gly Ile Ile Ile Ser Asp Thr Pro Val His Asp Cys Asn
290                 295                 300

Thr Thr Cys Gln Thr Pro Lys Gly Ala Ile Asn Thr Ser Leu Pro Phe
305                 310                 315                 320

Gln Asn Ile His Pro Ile Thr Ile Gly Lys Cys Pro Lys Tyr Val Lys
                325                 330                 335

Ser Thr Lys Leu Arg Leu Ala Thr Gly Leu Arg Asn Ser Pro Gln Arg
                340                 345                 350

Glu Arg Arg Lys Lys Arg Gly Leu Phe Gly Ala Ile Ala Gly Phe Ile
                355                 360                 365

Glu Gly Gly Trp Thr Gly Met Val Asp Gly Trp Tyr Gly Tyr His His
370                 375                 380

Gln Asn Glu Gln Gly Ser Gly Tyr Ala Ala Asp Leu Lys Ser Thr Gln
385                 390                 395                 400

Asn Ala Ile Asp Glu Ile Thr Asn Lys Val Asn Ser Val Ile Glu Lys
                405                 410                 415

Met Asn Thr Gln Phe Thr Ala Val Gly Lys Glu Phe Asn His Leu Glu
                420                 425                 430

Lys Arg Ile Glu Asn Leu Asn Lys Lys Val Asp Asp Gly Phe Leu Asp
                435                 440                 445

Ile Trp Thr Tyr Asn Ala Glu Leu Leu Val Leu Leu Glu Asn Glu Arg
450                 455                 460

Thr Leu Asp Tyr His Asp Ser Asn Val Lys Asn Leu Tyr Glu Lys Val
465                 470                 475                 480

Arg Ser Gln Leu Lys Asn Asn Ala Lys Glu Ile Gly Asn Gly Cys Phe
                485                 490                 495

Glu Phe Tyr His Lys Cys Asp Asn Thr Cys Met Glu Ser Val Lys Asn
                500                 505                 510

Gly Thr Tyr Asp Tyr Pro Lys Tyr Ser Glu Glu Ala Lys Leu Asn Arg
                515                 520                 525

Glu Glu Ile Asp Gly Val Lys Leu Glu Ser Thr Arg Ile Tyr Gln Gly
530                 535                 540

Ala Glu Asn Leu Tyr Phe Gln Gly Gly Ser Gly Tyr Ile Pro Glu Ala
545                 550                 555                 560

Pro Arg Asp Gly Gln Ala Tyr Val Arg Lys Asp Gly Glu Trp Val Leu
                565                 570                 575

Leu Ser Thr Phe Leu Gly His His His His His His His His
                580                 585                 590

<210> SEQ ID NO 49
<211> LENGTH: 15
<212> TYPE: PRT
<213> ORGANISM: Artificial Sequence
```

```
<220> FEATURE:
<223> OTHER INFORMATION: Synthetic

<400> SEQUENCE: 49

Arg Lys Lys Arg Gly Leu Phe Gly Ala Ile Ala Gly Phe Ile Glu
1               5                   10                  15

<210> SEQ ID NO 50
<211> LENGTH: 17
<212> TYPE: PRT
<213> ORGANISM: Artificial Sequence
<220> FEATURE:
<223> OTHER INFORMATION: Synthetic

<400> SEQUENCE: 50

Lys Glu Ser Thr Gln Lys Ala Ile Asp Gly Val Thr Asn Lys Val Asn
1               5                   10                  15

Ser

<210> SEQ ID NO 51
<211> LENGTH: 1790
<212> TYPE: DNA
<213> ORGANISM: Artificial Sequence
<220> FEATURE:
<223> OTHER INFORMATION: Synthetic

<400> SEQUENCE: 51
```

| | | |
|---|---|---|
| ccatggtaag cgctattgtt ttatatgtgc ttttggcggc ggcggcgcat tctgcctttg | 60 |
| cggatacact gtgtattggc taccacgcca acaatagcac cgataccgtg gatacagtgc | 120 |
| tggagaagaa tgtgaccgtg acccactctg tgaatctgct ggaggataag cacaatggca | 180 |
| agctgtgtaa gctgagagga gttgcccctc tgcacctggg caaatgtaat attgccggct | 240 |
| ggattctggg aaatcctgaa tgtgaaagcc tgtctacagc cagcagctgg tcttatatcg | 300 |
| tggaaacccc tagcagcgac aatggcacct gttaccctgg cgacttcatc gattacgagg | 360 |
| agctgagaga acagctgtct agcgtgtcca gcttcgagag attcgagatc ttccctaaga | 420 |
| caagcagctg gcctaatcac gattctaata agggagtgac agccgcctgt cctcatgccg | 480 |
| gagccaagtc cttttacaag aacctgatct ggctggtgag aaagaagaga ggcctgtttg | 540 |
| gagccatcgc cggctttatt gagtacatca cgacaagggg caaagaagtg ctggtgctgt | 600 |
| ggggaatcca ccaccctagc aaggagtcta cacagaaggc cattgatggc gttacaaata | 660 |
| aggtcaattc tgatgcctat gtgtttgtgg gcagcagcag atacagcaaa agttcaagc | 720 |
| ctgaaattgc cattagaccc aaagtgagag atcaggaagg cagaatgaat tactactgga | 780 |
| ccctggtgga acctggcgat aagatcacat ttgaggccac cggaaatctg gtggtgccta | 840 |
| gatatgcatt tgcctatgga gagaaatgct gctctggcat cattatctct gatacccctg | 900 |
| tgcacgactg taataccacc tgtcagacac taagggcgc cattaatacc agcctgccct | 960 |
| tccagaatat tcaccctatc accatcggca agtgtcctaa gtatgtgaag agcaccaagc | 1020 |
| tgagactggc taccggtctg agaaatagcc ctcagaggga gagacgcaag aagagaggcc | 1080 |
| tgtttggagc catcgccggc tttattgagg aggatggac cggaatggtg gatggctggt | 1140 |
| acggctatca ccaccagaat gagcagggat ccggatatgc cgccgatctg aagtctacac | 1200 |
| agaacgccat cgacgagatc acaaacaagg tgaacagcgt gatcgagaag atgaacaccc | 1260 |
| agttcacagc tgtgggcaag gagttcaacc acctggagaa gagaatcgag aacctgaaca | 1320 |
| agaaagtgga cgacggcttc ctggatattt ggacctacaa tgccgagctg ctcgtgctcc | 1380 |

```
tggagaatga gagaaccctg gactaccacg acagcaatgt gaagaacctg tacgagaagg    1440
tgagaagcca gctgaagaac aatgccaagg agatcggcaa cggctgcttt gagttctacc    1500
acaagtgtga caacacctgt atggagtctg tgaagaacgg cacctacgac taccctaagt    1560
atagcgagga ggccaagctg aatagagagg agatcgacgg cgtgaaactg gaaagcacaa    1620
gaatctatca gggcgctgaa aacctgtatt ttcagggcgg ttctggttac atcccggaag    1680
ctccgcgtga cggtcaggct tacgttcgta agacggtga atgggttctg ctgtctacct    1740
tcctgggtca ccatcatcac caccatcacc atcatcactg ataaaagctt                1790
```

<210> SEQ ID NO 52
<211> LENGTH: 589
<212> TYPE: PRT
<213> ORGANISM: Artificial Sequence
<220> FEATURE:
<223> OTHER INFORMATION: Synthetic

<400> SEQUENCE: 52

```
Met Val Ser Ala Ile Val Leu Tyr Val Leu Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Lys Thr Ser Ser Trp Pro
    130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Arg Lys Lys Arg
                165                 170                 175

Gly Leu Phe Gly Ala Ile Ala Gly Phe Ile Glu Tyr Ile Asn Asp Lys
            180                 185                 190

Gly Lys Glu Val Leu Val Leu Trp Gly Ile His His Pro Ser Lys Glu
        195                 200                 205

Ser Thr Gln Lys Ala Ile Asp Gly Val Thr Asn Lys Val Asn Ser Asp
    210                 215                 220

Ala Tyr Val Phe Val Gly Ser Ser Arg Tyr Ser Lys Lys Phe Lys Pro
225                 230                 235                 240

Glu Ile Ala Ile Arg Pro Lys Val Arg Asp Gln Glu Gly Arg Met Asn
                245                 250                 255

Tyr Tyr Trp Thr Leu Val Glu Pro Gly Asp Lys Ile Thr Phe Glu Ala
            260                 265                 270

Thr Gly Asn Leu Val Val Pro Arg Tyr Ala Phe Ala Met Glu Arg Asn
        275                 280                 285

Ala Gly Ser Gly Ile Ile Ile Ser Asp Thr Pro Val His Asp Cys Asn
```

Thr Thr Cys Gln Thr Pro Lys Gly Ala Ile Asn Thr Ser Leu Pro Phe
305                 310                 315                 320

Gln Asn Ile His Pro Ile Thr Ile Gly Lys Cys Pro Lys Tyr Val Lys
            325                 330                 335

Ser Thr Lys Leu Arg Leu Ala Thr Gly Leu Arg Asn Ile Pro Ser Ile
            340                 345                 350

Gln Ser Arg Gly Leu Phe Gly Ala Ile Ala Gly Phe Ile Glu Gly Gly
            355                 360                 365

Trp Thr Gly Met Val Asp Gly Trp Tyr Gly Tyr His His Gln Asn Glu
            370                 375                 380

Gln Gly Ser Gly Tyr Ala Ala Asp Leu Lys Ser Thr Gln Asn Ala Ile
385                 390                 395                 400

Asp Glu Ile Thr Asn Lys Val Asn Ser Val Ile Glu Lys Met Asn Thr
                405                 410                 415

Gln Phe Thr Ala Val Gly Lys Glu Phe Asn His Leu Glu Lys Arg Ile
            420                 425                 430

Glu Asn Leu Asn Lys Lys Val Asp Asp Gly Phe Leu Asp Ile Trp Thr
            435                 440                 445

Tyr Asn Ala Glu Leu Leu Val Leu Leu Glu Asn Glu Arg Thr Leu Asp
450                 455                 460

Tyr His Asp Ser Asn Val Lys Asn Leu Tyr Glu Lys Val Arg Ser Gln
465                 470                 475                 480

Leu Lys Asn Asn Ala Lys Glu Ile Gly Asn Gly Cys Phe Glu Phe Tyr
            485                 490                 495

His Lys Cys Asp Asn Thr Cys Met Glu Ser Val Lys Asn Gly Thr Tyr
            500                 505                 510

Asp Tyr Pro Lys Tyr Ser Glu Glu Ala Lys Leu Asn Arg Glu Glu Ile
            515                 520                 525

Asp Gly Val Lys Leu Glu Ser Thr Arg Ile Tyr Gln Gly Ala Glu Asn
530                 535                 540

Leu Tyr Phe Gln Gly Gly Ser Gly Tyr Ile Pro Glu Ala Pro Arg Asp
545                 550                 555                 560

Gly Gln Ala Tyr Val Arg Lys Asp Gly Glu Trp Val Leu Leu Ser Thr
            565                 570                 575

Phe Leu Gly His His His His His His His His
            580                 585

<210> SEQ ID NO 53
<211> LENGTH: 1781
<212> TYPE: DNA
<213> ORGANISM: Artificial Sequence
<220> FEATURE:
<223> OTHER INFORMATION: Synthetic

<400> SEQUENCE: 53
ccatggtaag cgctattgtt ttatatgtgc ttttggcggc ggcggcgcat tctgcctttg    60
cggatacact gtgtattggc taccacgcca acaatagcac cgataccgtg gatacagtgc   120
tggagaagaa tgtgaccgtg acccactctg tgaatctgct ggaggataag cacaatggca   180
agctgtgtaa agctgagagg agttgcccct cgcacctggg caatgtaat attgccggct   240 ggattctggg aaatcctgaa tgtgaaagcc tgtctacagc cagcagctgg tcttatatcg   300
tggaaacccc tagcagcgac aatggcacct gttaccctgg cgacttcatc gattacgagg   360
agctgagaga acagctgtct agcgtgtcca gcttcgagag attcgagatc ttccctaaga   420

```
caagcagctg gcctaatcac gattctaata agggagtgac agccgcctgt cctcatgccg    480
gagccaagtc cttttacaag aacctgatct ggctggtgag aaagaagaga ggcctgtttg    540
gagccatcgc cggctttatt gagtacatca cgacaaggg caaagaagtg ctggtgctgt    600
ggggaatcca ccaccctagc aaggagtcta cacagaaggc cattgatggc gttacaaata    660
aggtcaattc tgatgcctat gtgtttgtgg gcagcagcag atacagcaaa aagttcaagc    720
ctgaaattgc cattagaccc aaagtgagag atcaggaagg cagaatgaat tactactgga    780
ccctggtgga acctggcgat aagatcacat ttgaggccac cggaaatctg gtggtgccta    840
gatatgcatt tgctatggag agaaatgctg gctctggcat cattatctct gatacccctg    900
tgcacgactg taataccacc tgtcagacac taagggcgc cattaatacc agcctgccct    960
tccagaatat tcaccctatc accatcggca agtgtcctaa gtatgtgaag agcaccaagc   1020
tgagactggc taccggtctg agaaatatcc ctagcatcca gagcagaggc ctgtttggag   1080
ccatcgccgg ctttattgag ggaggatgga ccggaatggt ggatggctgg tacggctatc   1140
accaccagaa tgagcaggga tccggatatg ccgccgatct gaagtctaca cagaacgcca   1200
tcgacgagat cacaaacaag gtgaacagcg tgatcgagaa gatgaacacc cagtttacag   1260
ctgtgggcaa ggagttcaac cacctggaga agagaatcga gaacctgaac aagaaagtgg   1320
acgacggctt cctggatatt tggacctaca atgccgagct gctcgtgctc ctggagaatg   1380
agagaaccct ggactaccac gacagcaatg tgaagaacct gtacgagaag gtgagaagcc   1440
agctgaagaa caatgccaag gagatcggca acggctgctt tgagttctac cacaagtgtg   1500
acaacacctg tatggagtct gtgaagaacg gcacctacga ctaccctaag tatagcgagg   1560
aggccaagct gaatagagag gagatcgacg gcgtgaaact ggaaagcaca agaatctatc   1620
agggcgctga aaacctgtat tttcagggcg ttctggtta catcccggaa gctccgcgtg   1680
acggtcaggc ttacgttcgt aaagacggtg aatgggttct gctgtctacc ttcctgggtc   1740
accatcatca ccaccatcac catcatcact gataaaagct t                      1781
```

<210> SEQ ID NO 54
<211> LENGTH: 585
<212> TYPE: PRT
<213> ORGANISM: Artificial Sequence
<220> FEATURE:
<223> OTHER INFORMATION: Synthetic

<400> SEQUENCE: 54

```
Met Val Ser Ala Ile Val Leu Tyr Val Leu Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
```

```
            115                 120                 125
Ser Ser Phe Glu Arg Phe Glu Ile Phe Pro Lys Thr Ser Ser Trp Pro
    130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Arg Lys Lys Arg
                165                 170                 175

Gly Leu Phe Gly Ala Ile Ala Gly Phe Ile Glu Gly Tyr Ile Asn Asp
            180                 185                 190

Lys Gly Lys Glu Val Leu Val Leu Trp Gly Ile His His Pro Ser Thr
        195                 200                 205

Ser Ala Asp Gln Gln Ser Leu Tyr Gln Asn Ala Asp Ala Tyr Val Phe
    210                 215                 220

Val Gly Ser Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Ala Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ile Glu Asn Leu Tyr Phe Gln Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
    450                 455                 460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Glu Ile Asp Gly Val Lys
        515                 520                 525

Leu Glu Ser Thr Arg Ile Tyr Gln Gly Ala Glu Asn Leu Tyr Phe Gln
    530                 535                 540
```

Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly His
                565                 570                 575

His His His His His His His His
            580                 585

<210> SEQ ID NO 55
<211> LENGTH: 1769
<212> TYPE: DNA
<213> ORGANISM: Artificial Sequence
<220> FEATURE:
<223> OTHER INFORMATION: Synthetic

<400> SEQUENCE: 55

```
ccatggtaag cgctattgtt ttatatgtgc ttttggcggc ggcggcgcat tctgcctttg      60
cggatacact gtgtattggc taccacgcca acaatagcac cgataccgtg gatacagtgc    120
tggagaagaa tgtgaccgtg acccactctg tgaatctgct ggaggataag cacaatggca    180
agctgtgtaa gctgagagga gttgcccctc tgcacctggg caaatgtaat attgccggct    240
ggattctggg aaatcctgaa tgtgaaagcc tgtctacagc cagcagctgg tcttatatcg    300
tggaaacccc tagcagcgac aatggcacct gttaccctgg cgacttcatc gattacgagg    360
agctgagaga acagctgtct agcgtgtcca gcttcgagag attcgagatc ttccctaaga    420
caagcagctg gcctaatcac gattctaata agggagtgac agccgcctgt cctcatgccg    480
gagccaagtc ctttacaag aacctgatct ggctggtgag aaagaagaga ggcctgttcg    540
gcgctatcgc cggcttcatt gagggataca tcaacgacaa gggcaagaa gtgctggtgc    600
tgtggggaat ccaccaccct agcacaagcg ccgatcagca gagcctgtac cagaatgccg    660
atgcctatgt gtttgtgggc agcagcagat acagcaaaaa gttcaagcct gaaattgcca    720
ttagacccca agtgagagat caggaaggca gaatgaatta ctactggacc ctggtggaac    780
ctggcgataa gatcacattt gaggccaccg gaaatctggt ggtgcctaga tatgcatttg    840
ctatggagag aaatgctggc tctggcatca ttatctctga taccctgtg cacgactgta    900
ataccacctg tcagacacct aagggcgcca ttaataccag cctgcccttc agaatattc    960
accctatcac catcggcaag tgtcctaagt atgtgaagag caccaagctg agactggcta   1020
ccggtctgag aaatatcgaa aacctgtatt ttcaaggcct gtttggagcc atcgccggct   1080
ttattgaggg aggatggacc ggaatggtgg atggctggta cggctatcac caccagaatg   1140
agcagggatc cggatatgcc gccgatctga gtctacaca gaacgccatc gacgagatca   1200
caaacaaggt gaacagcgtg atcgagaaga tgaacaccca gtttacagct gtgggcaagg   1260
agttcaacca cctggagaag agaatcgaga acctgaacaa gaaagtggac gacggcttcc   1320
tggatatttg gacctacaat gccgagctgc tcgtgctcct ggagaatgag agaaccctgg   1380
actaccacga cagcaatgtg aagaacctgt acgagaaggt gagaagccag ctgaagaaca   1440
atgccaagga gatcggcaac ggctgctttg agttctacca caagtgtgac aacacctgta   1500
tggagtctgt gaagaacggc acctacgact accctaagta tagcgaggag gccaagctga   1560
atagagagga gatcgacggc gtgaaactgg aaagcacaag aatctatcag ggcgctgaaa   1620
acctgtattt tcagggcggt tctggttaca cccggaagc tccgcgtgac ggtcaggctt   1680
acgttcgtaa agacggtgaa tgggttctgc tgtctacctt cctgggtcac catcatcacc   1740
accatcacca tcatcactga taaaagctt                                     1769
```

<210> SEQ ID NO 56
<211> LENGTH: 593
<212> TYPE: PRT
<213> ORGANISM: Artificial Sequence
<220> FEATURE:
<223> OTHER INFORMATION: Synthetic

<400> SEQUENCE: 56

```
Met Val Ser Ala Ile Val Leu Tyr Val Leu Leu Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Lys Thr Ser Ser Trp Pro
    130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
                165                 170                 175

Ser Tyr Pro Lys Leu Ser Lys Ser Tyr Ile Asn Asp Lys Gly Lys Glu
            180                 185                 190

Val Leu Val Leu Trp Gly Ile His His Pro Ser Thr Ser Ala Asp Gln
        195                 200                 205

Gln Ser Leu Tyr Gln Asn Ala Asp Ala Tyr Val Phe Val Gly Ser Ser
    210                 215                 220

Arg Tyr Ser Lys Lys Phe Lys Pro Ser Leu Leu Thr Glu Val Glu Thr
225                 230                 235                 240

Pro Thr Arg Asn Gly Trp Glu Cys Lys Cys Ser Asp Ser Gly Arg Met
                245                 250                 255

Asn Tyr Tyr Trp Thr Leu Val Glu Pro Gly Asp Lys Ile Thr Phe Glu
            260                 265                 270

Ala Thr Gly Asn Leu Val Val Pro Arg Tyr Ala Phe Ala Met Glu Arg
        275                 280                 285

Asn Ala Gly Ser Gly Ile Ile Ile Ser Asp Thr Pro Val His Asp Cys
    290                 295                 300

Asn Thr Thr Cys Gln Thr Pro Lys Gly Ala Ile Asn Thr Ser Leu Pro
305                 310                 315                 320

Phe Gln Asn Ile His Pro Ile Thr Ile Gly Lys Cys Pro Lys Tyr Val
                325                 330                 335

Lys Ser Thr Lys Leu Arg Leu Ala Thr Gly Leu Arg Asn Ser Pro Gln
            340                 345                 350

Arg Glu Arg Arg Lys Lys Arg Gly Leu Phe Gly Ala Ile Ala Gly Phe
        355                 360                 365
```

```
Ile Glu Gly Gly Trp Thr Gly Met Val Asp Gly Trp Tyr Gly Tyr His
            370                 375                 380

His Gln Asn Glu Gln Gly Ser Gly Tyr Ala Ala Asp Leu Lys Ser Thr
385                 390                 395                 400

Gln Asn Ala Ile Asp Glu Ile Thr Asn Lys Val Asn Ser Val Ile Glu
                405                 410                 415

Lys Met Asn Thr Gln Phe Thr Ala Val Gly Lys Glu Phe Asn His Leu
            420                 425                 430

Glu Lys Arg Ile Glu Asn Leu Asn Lys Lys Val Asp Asp Gly Phe Leu
            435                 440                 445

Asp Ile Trp Thr Tyr Asn Ala Glu Leu Leu Val Leu Leu Glu Asn Glu
            450                 455                 460

Arg Thr Leu Asp Tyr His Asp Ser Asn Val Lys Asn Leu Tyr Glu Lys
465                 470                 475                 480

Val Arg Ser Gln Leu Lys Asn Asn Ala Lys Glu Ile Gly Asn Gly Cys
                485                 490                 495

Phe Glu Phe Tyr His Lys Cys Asp Asn Thr Cys Met Glu Ser Val Lys
                500                 505                 510

Asn Gly Thr Tyr Asp Tyr Pro Lys Tyr Ser Glu Ala Lys Leu Asn
            515                 520                 525

Arg Glu Glu Ile Asp Gly Val Lys Leu Glu Ser Thr Arg Ile Tyr Gln
            530                 535                 540

Gly Ala Glu Asn Leu Tyr Phe Gln Gly Gly Ser Gly Tyr Ile Pro Glu
545                 550                 555                 560

Ala Pro Arg Asp Gly Gln Ala Tyr Val Arg Lys Asp Gly Glu Trp Val
                565                 570                 575

Leu Leu Ser Thr Phe Leu Gly His His His His His His His His
            580                 585                 590

His

<210> SEQ ID NO 57
<211> LENGTH: 21
<212> TYPE: PRT
<213> ORGANISM: Artificial Sequence
<220> FEATURE:
<223> OTHER INFORMATION: Synthetic

<400> SEQUENCE: 57

Ser Leu Leu Thr Glu Val Glu Thr Pro Thr Arg Asn Gly Trp Glu Cys
1               5                   10                  15

Lys Cys Ser Asp Ser
            20

<210> SEQ ID NO 58
<211> LENGTH: 1793
<212> TYPE: DNA
<213> ORGANISM: Artificial Sequence
<220> FEATURE:
<223> OTHER INFORMATION: Synthetic

<400> SEQUENCE: 58
ccatggtaag cgctattgtt ttatatgtgc ttttggcggc ggcggcgcat tctgcctttg    60
cggatacact gtgtattggc taccacgcca acaatagcac cgataccgtg gatacagtgc   120
tggagaagaa tgtgaccgtg acccactctg tgaatctgct ggaggataag cacaatggca   180
agctgtgtaa gctgagagga gttgcccctc tgcacctggg caaatgtaat attgccggct   240
```

```
ggattctggg aaatcctgaa tgtgaaagcc tgtctacagc cagcagctgg tcttatatcg    300
tggaaacccc tagcagcgac aatggcacct gttaccctgg cgacttcatc gattacgagg    360
agctgagaga acagctgtct agcgtgtcca gcttcgagag attcgagatc ttccctaaga    420
caagcagctg gcctaatcac gattctaata agggagtgac agccgcctgt cctcatgccg    480
gagccaagtc cttttacaag aacctgatct ggctggtgaa gagggcaac agctaccca    540 agctgtctaa gagctacatc aacgacaagg gcaaagaagt gctggtgctg tggggaatcc    600
accaccctag cacaagcgcc gatcagcaga gcctgtacca gaatgccgat gcctatgtgt    660 tgtgggcag cagcagatac agcaaaaagt tcaagccttc cctgctgacc gaggtggaga    720
cccccaccag gaacggctgg gagtgcaagt gctccgactc cggcagaatg aattactact    780
ggaccctggt ggaacctggc gataagatca catttgaggc caccggaaat ctggtggtgc    840
ctagatatgc atttgctatg gagagaaatg ctggctctgg catcattatc tctgataccc    900
ctgtgcacga ctgtaatacc acctgtcaga cacctaaggg cgccattaat accagcctgc    960
ccttccagaa tattcaccct atcaccatcg gcaagtgtcc taagtatgtg aagagcacca   1020
agctgagact ggctaccggt ctgagaaata gccctcagag ggagagacgc aagaagagag   1080
gcctgtttgg agccatcgcc ggcttttatt agggaggatg accggaatg gtggatggct   1140 ggtacggcta tcaccaccag aatgagcagg atccggata tgccgccgat ctgaagtcta   1200
cacagaacgc catcgacgag atcacaaaca aggtgaacag cgtgatcgag aagatgaaca   1260
cccagtttac agctgtgggc aaggagttca accacctgga aagagaatc gagaacctga   1320 acaagaaagt ggacgacggc ttcctggata tttggaccta caatgccgag ctgctcgtgc   1380
tcctggagaa tgagagaacc ctggactacc acgacagcaa tgtgaagaac ctgtacgaga   1440
aggtgagaag ccagctgaag aacaatgcca aggagatcgg caacggctgc tttgagttct   1500
accacaagtg tgacaacacc tgtatggagt ctgtgaagaa cggcacctac gactacccta   1560
agtatagcga ggaggccaag ctgaatagag aggagatcga cggcgtgaaa ctggaaagca   1620
caagaatcta tcagggcgct gaaaaacctgt attttcaggg cggttctggt tacatcccgg   1680
aagctccgcg tgacggtcag gcttacgttc gtaaagacgg tgaatgggtt ctgctgtcta   1740
ccttcctggg tcaccatcat caccaccatc accatcatca ctgataaaag ctt          1793
```

<210> SEQ ID NO 59
<211> LENGTH: 593
<212> TYPE: PRT
<213> ORGANISM: Artificial Sequence
<220> FEATURE:
<223> OTHER INFORMATION: Synthetic

<400> SEQUENCE: 59

```
Met Val Ser Ala Ile Val Leu Tyr Val Leu Leu Ala Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95
```

-continued

```
Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
            115                 120                 125

Ser Ser Phe Glu Arg Phe Glu Ile Phe Pro Lys Thr Ser Ser Trp Pro
            130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
                165                 170                 175

Ser Tyr Pro Lys Leu Ser Lys Ser Tyr Ile Asn Asp Lys Gly Lys Glu
            180                 185                 190

Val Leu Val Leu Trp Gly Ile His His Pro Ser Ser Leu Leu Thr Glu
            195                 200                 205

Val Glu Thr Pro Thr Arg Asn Gly Trp Glu Cys Lys Cys Ser Asp Ser
            210                 215                 220

Asp Ala Tyr Val Phe Val Gly Ser Ser Arg Tyr Ser Lys Lys Phe Lys
225                 230                 235                 240

Pro Glu Ile Ala Ile Arg Pro Lys Val Arg Asp Gln Glu Gly Arg Met
                245                 250                 255

Asn Tyr Tyr Trp Thr Leu Val Glu Pro Gly Asp Lys Ile Thr Phe Glu
            260                 265                 270

Ala Thr Gly Asn Leu Val Val Pro Arg Tyr Ala Phe Ala Met Glu Arg
            275                 280                 285

Asn Ala Gly Ser Gly Ile Ile Ile Ser Asp Thr Pro Val His Asp Cys
            290                 295                 300

Asn Thr Thr Cys Gln Thr Pro Lys Gly Ala Ile Asn Thr Ser Leu Pro
305                 310                 315                 320

Phe Gln Asn Ile His Pro Ile Thr Ile Gly Lys Cys Pro Lys Tyr Val
                325                 330                 335

Lys Ser Thr Lys Leu Arg Leu Ala Thr Gly Leu Arg Asn Ser Pro Gln
            340                 345                 350

Arg Glu Arg Arg Lys Lys Arg Gly Leu Phe Gly Ala Ile Ala Gly Phe
            355                 360                 365

Ile Glu Gly Gly Trp Thr Gly Met Val Asp Gly Trp Tyr Gly Tyr His
            370                 375                 380

His Gln Asn Glu Gln Gly Ser Gly Tyr Ala Ala Asp Leu Lys Ser Thr
385                 390                 395                 400

Gln Asn Ala Ile Asp Glu Ile Thr Asn Lys Val Asn Ser Val Ile Glu
                405                 410                 415

Lys Met Asn Thr Gln Phe Thr Ala Val Gly Lys Glu Phe Asn His Leu
            420                 425                 430

Glu Lys Arg Ile Glu Asn Leu Asn Lys Lys Val Asp Asp Gly Phe Leu
            435                 440                 445

Asp Ile Trp Thr Tyr Asn Ala Glu Leu Leu Val Leu Leu Glu Asn Glu
            450                 455                 460

Arg Thr Leu Asp Tyr His Asp Ser Asn Val Lys Asn Leu Tyr Glu Lys
465                 470                 475                 480

Val Arg Ser Gln Leu Lys Asn Asn Ala Lys Glu Ile Gly Asn Gly Cys
                485                 490                 495

Phe Glu Phe Tyr His Lys Cys Asp Asn Thr Cys Met Glu Ser Val Lys
            500                 505                 510
```

```
Asn Gly Thr Tyr Asp Tyr Pro Lys Tyr Ser Glu Glu Ala Lys Leu Asn
        515                 520                 525

Arg Glu Glu Ile Asp Gly Val Lys Leu Glu Ser Thr Arg Ile Tyr Gln
    530                 535                 540

Gly Ala Glu Asn Leu Tyr Phe Gln Gly Gly Ser Gly Tyr Ile Pro Glu
545                 550                 555                 560

Ala Pro Arg Asp Gly Gln Ala Tyr Val Arg Lys Asp Gly Glu Trp Val
                565                 570                 575

Leu Leu Ser Thr Phe Leu Gly His His His His His His His His
            580                 585                 590

His

<210> SEQ ID NO 60
<211> LENGTH: 1793
<212> TYPE: DNA
<213> ORGANISM: Artificial Sequence
<220> FEATURE:
<223> OTHER INFORMATION: Synthetic

<400> SEQUENCE: 60
```

| | | | | | |
|---|---|---|---|---|---|
| ccatggtaag | cgctattgtt | ttatatgtgc | ttttggcggc | ggcggcgcat | tctgcctttg | 60 |
| cggatacact | gtgtattggc | taccacgcca | acaatagcac | cgataccgtg | gatacagtgc | 120 |
| tggagaagaa | tgtgaccgtg | acccactctg | tgaatctgct | ggaggataag | cacaatggca | 180 |
| agctgtgtaa | gctgagagga | gttgcccctc | tgcacctggg | caaatgtaat | attgccggct | 240 |
| ggattctggg | aaatcctgaa | tgtgaaagcc | tgtctacagc | cagcagctgg | tcttatatcg | 300 |
| tggaaacccc | tagcagcgac | aatggcacct | gttaccctgg | cgacttcatc | gattacgagg | 360 |
| agctgagaga | acagctgtct | agcgtgtcca | gcttcgagag | attcgagatc | ttccctaaga | 420 |
| caagcagctg | gcctaatcac | gattctaata | agggagtgac | agccgcctgt | cctcatgccg | 480 |
| gagccaagtc | cttttacaag | aacctgatct | ggctggtgaa | gaagggcaac | agctacccta | 540 |
| agctgtctaa | gagctacatc | aacgacaagg | gcaaagaagt | gctggtgctg | tggggaatcc | 600 |
| accaccctag | ctccctgctg | accgaggtgg | agacccccac | caggaacggc | tgggagtgca | 660 |
| agtgctccga | ctccgatgcc | tatgtgtttg | tgggcagcag | cagatacagc | aaaaagttca | 720 |
| agcctgaaat | tgccattaga | cccaaagtga | gagatcagga | aggcagaatg | aattactact | 780 |
| ggaccctggt | ggaacctggc | gataagatca | catttgaggc | caccggaaat | ctggtggtgc | 840 |
| ctagatatgc | atttgctatg | gagagaaatg | ctggctctgg | catcattatc | tctgataccc | 900 |
| ctgtgcacga | ctgtaatacc | acctgtcaga | cacctaaggg | cgccattaat | accagcctgc | 960 |
| ccttccagaa | tattcaccct | atcaccatcg | gcaagtgtcc | taagtatgtg | aagagcacca | 1020 |
| agctgagact | ggctaccggt | ctgagaaata | gccctcagag | ggagagacgc | aagaagagag | 1080 |
| gcctgtttgg | agccatcgcc | ggctttattg | agggaggatg | gaccggaatg | gtggatggct | 1140 |
| ggtacggcta | tcaccaccag | aatgagcagg | gatccggata | tgccgccgat | ctgaagtcta | 1200 |
| cacagaacgc | catcgacgag | atcacaaaca | aggtgaacag | cgtgatcgag | aagatgaaca | 1260 |
| cccagtttac | agctgtgggc | aaggagttca | accacctgga | aagagaatc | gagaacctga | 1320 |
| acaagaaagt | ggacgacggc | ttcctggata | tttggaccta | caatgccgag | ctgctcgtgc | 1380 |
| tcctggagaa | tgagagaacc | ctggactacc | acgacagcaa | tgtgaagaac | ctgtacgaga | 1440 |
| aggtgagaag | ccagctgaag | aacaatgcca | aggagatcgg | caacggctgc | tttgagttct | 1500 |
| accacaagtg | tgacaacacc | tgtatggagt | ctgtgaagaa | cggcacctac | gactacccta | 1560 |

-continued

```
agtatagcga ggaggccaag ctgaatagag aggagatcga cggcgtgaaa ctggaaagca    1620
caagaatcta tcagggcgct gaaaacctgt attttcaggg cggttctggt tacatcccgg    1680
aagctccgcg tgacggtcag gcttacgttc gtaaagacgg tgaatgggtt ctgctgtcta    1740
ccttcctggg tcaccatcat caccaccatc accatcatca ctgataaaag ctt           1793
```

<210> SEQ ID NO 61
<211> LENGTH: 591
<212> TYPE: PRT
<213> ORGANISM: Artificial Sequence
<220> FEATURE:
<223> OTHER INFORMATION: Synthetic

<400> SEQUENCE: 61

```
Met Val Ser Ala Ile Val Leu Tyr Val Leu Leu Ala Ala Ala Ala His
1               5                   10                  15

Ser Ala Phe Ala Asp Thr Leu Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Lys His Asn Gly Lys Leu Cys Lys Leu
    50                  55                  60

Arg Gly Val Ala Pro Leu His Leu Gly Lys Cys Asn Ile Ala Gly Trp
65                  70                  75                  80

Ile Leu Gly Asn Pro Glu Cys Glu Ser Leu Ser Thr Ala Ser Ser Trp
                85                  90                  95

Ser Tyr Ile Val Glu Thr Pro Ser Ser Asp Asn Gly Thr Cys Tyr Pro
            100                 105                 110

Gly Asp Phe Ile Asp Tyr Glu Glu Leu Arg Glu Gln Leu Ser Ser Val
        115                 120                 125

Ser Ser Phe Glu Arg Phe Glu Ile Phe Pro Lys Thr Ser Ser Trp Pro
    130                 135                 140

Asn His Asp Ser Asn Lys Gly Val Thr Ala Ala Cys Pro His Ala Gly
145                 150                 155                 160

Ala Lys Ser Phe Tyr Lys Asn Leu Ile Trp Leu Val Lys Lys Gly Asn
                165                 170                 175

Ser Tyr Pro Lys Leu Ser Lys Ser Tyr Ile Asn Asp Lys Gly Lys Glu
            180                 185                 190

Val Leu Val Leu Trp Gly Ile His His Pro Ser Thr Ser Ala Asp Gln
        195                 200                 205

Gln Ser Leu Tyr Gln Asn Ala Asp Ala Tyr Val Phe Val Gly Ser Ser
    210                 215                 220

Arg Tyr Ser Lys Lys Phe Lys Pro Ser Leu Leu Thr Glu Val Glu Thr
225                 230                 235                 240

Pro Thr Arg Asn Gly Trp Glu Cys Lys Cys Ser Asp Ser Gly Arg Met
                245                 250                 255

Asn Tyr Tyr Trp Thr Leu Val Glu Pro Gly Asp Lys Ile Thr Phe Glu
            260                 265                 270

Ala Thr Gly Asn Leu Val Val Pro Arg Tyr Ala Phe Ala Met Glu Arg
        275                 280                 285

Asn Ala Gly Ser Gly Ile Ile Ile Ser Asp Thr Pro Val His Asp Cys
    290                 295                 300

Asn Thr Thr Cys Gln Thr Pro Lys Gly Ala Ile Asn Thr Ser Leu Pro
305                 310                 315                 320

Phe Gln Asn Ile His Pro Ile Thr Ile Gly Lys Cys Pro Lys Tyr Val
```

Lys Ser Thr Lys Leu Arg Leu Ala Thr Gly Leu Arg Asn Ser Pro Glu
              325                 330                 335

Asn Leu Tyr Phe Gln Gly Leu Phe Gly Ala Ile Ala Gly Phe Ile Glu
            340                 345                 350

Gly Gly Trp Thr Gly Met Val Asp Gly Trp Tyr Gly Tyr His His Gln
        355                 360                 365

Asn Glu Gln Gly Ser Gly Tyr Ala Ala Asp Leu Lys Ser Thr Gln Asn
    370                 375                 380

Ala Ile Asp Glu Ile Thr Asn Lys Val Asn Ser Val Ile Glu Lys Met
385                 390                 395                 400

Asn Thr Gln Phe Thr Ala Val Gly Lys Glu Phe Asn His Leu Glu Lys
            405                 410                 415

Arg Ile Glu Asn Leu Asn Lys Lys Val Asp Asp Gly Phe Leu Asp Ile
        420                 425                 430

Trp Thr Tyr Asn Ala Glu Leu Leu Val Leu Leu Glu Asn Glu Arg Thr
    435                 440                 445

Leu Asp Tyr His Asp Ser Asn Val Lys Asn Leu Tyr Glu Lys Val Arg
450                 455                 460

Ser Gln Leu Lys Asn Asn Ala Lys Glu Ile Gly Asn Gly Cys Phe Glu
            465                 470                 475                 480

Phe Tyr His Lys Cys Asp Asn Thr Cys Met Glu Ser Val Lys Asn Gly
        485                 490                 495

Thr Tyr Asp Tyr Pro Lys Tyr Ser Glu Glu Ala Lys Leu Asn Arg Glu
    500                 505                 510

Glu Ile Asp Gly Val Lys Leu Glu Ser Thr Arg Ile Tyr Gln Gly Ala
            515                 520                 525

Glu Asn Leu Tyr Phe Gln Gly Gly Ser Gly Tyr Ile Pro Glu Ala Pro
545                 550                 555                 560

Arg Asp Gly Gln Ala Tyr Val Arg Lys Asp Gly Glu Trp Val Leu Leu
            530                 535                 540

Ser Thr Phe Leu Gly His His His His His His His His His
            565                 570                 575

<210> SEQ ID NO 62
<211> LENGTH: 1787
<212> TYPE: DNA
<213> ORGANISM: Artificial Sequence
<220> FEATURE:
<223> OTHER INFORMATION: Synthetic

<400> SEQUENCE: 62
ccatggtaag cgctattgtt ttatatgtgc ttttggcggc ggcggcgcat tctgcctttg      60
cggatacact gtgtattggc taccacgcca acaatagcac cgataccgtg gatacagtgc    120
tggagaagaa tgtgaccgtg acccactctg tgaatctgct ggaggataag cacaatggca    180
agctgtgtaa gctgagagga gttgcccctc tgcacctggg caaatgtaat attgccggct    240
ggattctggg aaatcctgaa tgtgaaagcc tgtctacagc cagcagctgg tcttatatcg    300
tggaaacccc tagcagcgac aatggcacct gttaccctgg cgacttcatc gattacgagg    360
agctgagaga acagctgtct agcgtgtcca gcttcgagag attcgagatc ttccctaaga    420
caagcagctg gcctaatcac gattctaata agggagtgac agccgcctgt cctcatgccg    480
gagccaagtc cttttacaag aacctgatct ggctggtgaa gaagggcaac agctaccctg    540
agctgtctaa gagctacatc aacgacaagg gcaaagaagt gctggtgctg tgggaatcc     600

```
accaccctag cacaagcgcc gatcagcaga gcctgtacca gaatgccgat gcctatgtgt    660
ttgtgggcag cagcagatac agcaaaaagt tcaagccttc cctgctgacc gaggtggaga    720
cccccaccag gaacggctgg gagtgcaagt gctccgactc cggcagaatg aattactact    780
ggaccctggt ggaacctggc gataagatca catttgaggc caccggaaat ctggtggtgc    840
ctagatatgc atttgctatg gagagaaatg ctggctctgg catcattatc tctgataccc    900
ctgtgcacga ctgtaatacc acctgtcaga cacctaaggg cgccattaat accagcctgc    960
ccttccagaa tattcaccct atcaccatcg gcaagtgtcc taagtatgtg aagagcacca   1020
agctgagact ggctaccggt ctgagaaata gccctgaaaa cctgtatttt caaggcctgt   1080
ttggagccat cgccggcttt attgagggag gatggaccgg aatggtggat ggctggtacg   1140
gctatcacca ccagaatgag cagggatccg gatatgccgc cgatctgaag tctacacaga   1200
acgccatcga cgagatcaca aacaaggtga acagcgtgat cgagaagatg aacacccagt   1260
ttacagctgt gggcaaggag ttcaaccacc tggagaagag aatcgagaac ctgaacaaga   1320
aagtggacga cggcttcctg gatatttgga cctacaatgc cgagctgctc gtgctcctgg   1380
agaatgagag aaccctggac taccacgaca gcaatgtgaa gaacctgtac gagaaggtga   1440
gaagccagct gaagaacaat gccaaggaga tcggcaacgg ctgctttgag ttctaccaca   1500
agtgtgacaa cacctgtatg gagtctgtga agaacggcac ctacgactac cctaagtata   1560
gcgaggaggc caagctgaat agagaggaga tcgacggcgt gaaactggaa agcacaagaa   1620
tctatcaggg cgctgaaaac ctgtattttc agggcggttc tggttacatc ccggaagctc   1680
cgcgtgacgg tcaggcttac gttcgtaaag acggtgaatg ggttctgctg tctaccttcc   1740
tgggtcacca tcatcaccac catcaccatc atcactgata aaagctt                 1787
```

<210> SEQ ID NO 63
<211> LENGTH: 514
<212> TYPE: PRT
<213> ORGANISM: Artificial Sequence
<220> FEATURE:
<223> OTHER INFORMATION: Synthetic

<400> SEQUENCE: 63

```
Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
                20                  25                  30

Gln Ile Glu Val Thr Asn Ala Thr Glu Leu Val Gln Ser Ser Ser Thr
            35                  40                  45

Gly Lys Ile Cys Asn Asn Pro His Arg Ile Leu Asp Gly Ile Asp Cys
        50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
                100                 105                 110

Ala Ser Ser Gly Thr Leu Glu Phe Ile Thr Glu Gly Phe Thr Trp Thr
            115                 120                 125

Gly Val Thr Gln Asn Gly Gly Ser Asn Ala Cys Lys Arg Gly Pro Gly
        130                 135                 140

Ser Gly Phe Phe Ser Arg Leu Asn Trp Leu Thr Lys Ser Gly Ser Thr
```

```
            145                 150                 155                 160
Tyr Pro Val Leu Asn Val Thr Met Pro Asn Asn Asp Asn Phe Asp Lys
                165                 170                 175

Leu Tyr Ile Trp Gly Ile His His Pro Ser Thr Asn Gln Glu Gln Thr
                180                 185                 190

Ser Leu Tyr Val Gln Ala Ser Gly Arg Val Thr Val Ser Thr Arg Arg
            195                 200                 205

Ser Gln Gln Thr Ile Ile Pro Asn Ile Gly Ser Arg Pro Trp Val Arg
        210                 215                 220

Gly Leu Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Asp Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr Arg Gly Leu Phe Gly Ala Ile Ala
                325                 330                 335

Gly Phe Ile Glu Asn Gly Trp Glu Gly Met Ile Asp Gly Trp Tyr Gly
            340                 345                 350

Phe Arg His Gln Asn Ser Glu Gly Thr Gly Gln Ala Ala Asp Leu Lys
        355                 360                 365

Ser Thr Gln Ala Ala Ile Asp Gln Ile Asn Gly Lys Leu Asn Arg Val
    370                 375                 380

Ile Glu Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Arg Arg Gln Leu Arg Glu Asn Ala Glu Glu Met Gly Asn
    450                 455                 460

Gly Cys Phe Lys Ile Tyr His Lys Cys Asp Asn Ala Cys Ile Glu Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp

<210> SEQ ID NO 64
<211> LENGTH: 512
<212> TYPE: PRT
<213> ORGANISM: Artificial Sequence
<220> FEATURE:
<223> OTHER INFORMATION: Synthetic

<400> SEQUENCE: 64
```

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Lys
        195                 200                 205

Lys Phe Lys Pro Glu Ile Ala Ile Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Leu Lys Ser Thr
        355                 360                 365

Gln Asn Ala Ile Asp Glu Ile Thr Asn Lys Val Asn Ser Val Ile Glu
    370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415
```

```
Asp Ile Trp Thr Tyr Asn Ala Glu Leu Val Leu Leu Glu Asn Glu
                420                 425                 430

Arg Thr Leu Asp Tyr His Asp Ser Asn Val Arg Asn Leu Tyr Glu Lys
            435                 440                 445

Val Arg Ser Gln Leu Lys Asn Asn Ala Lys Glu Ile Gly Asn Gly Cys
        450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Ala Lys Leu Asn
                485                 490                 495

Arg Glu Glu Ile Asp Gly Val Lys Leu Glu Ser Thr Arg Ile Tyr Gln
            500                 505                 510
```

<210> SEQ ID NO 65
<211> LENGTH: 511
<212> TYPE: PRT
<213> ORGANISM: Artificial Sequence
<220> FEATURE:
<223> OTHER INFORMATION: Synthetic

<400> SEQUENCE: 65

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
    50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Asn Thr
        115                 120                 125

Asn Gly Val Thr Ala Ala Cys Ser His Glu Gly Lys Ser Ser Phe Tyr
    130                 135                 140

Arg Asn Leu Leu Trp Leu Thr Glu Lys Glu Gly Ser Tyr Pro Lys Leu
145                 150                 155                 160

Lys Asn Ser Tyr Val Asn Lys Lys Gly Lys Glu Val Leu Val Leu Trp
                165                 170                 175

Gly Ile His His Pro Pro Asn Ser Lys Glu Gln Gln Asn Leu Tyr Gln
            180                 185                 190

Asn Glu Asn Ala Tyr Val Ser Val Val Thr Ser Asn Tyr Asn Arg Arg
        195                 200                 205

Phe Thr Pro Glu Ile Ala Glu Arg Pro Lys Val Arg Asp Gln Ala Gly
    210                 215                 220

Arg Met Asn Tyr Tyr Trp Thr Leu Leu Lys Pro Gly Asp Thr Ile Ile
225                 230                 235                 240

Phe Glu Ala Asn Gly Asn Leu Ile Ala Pro Met Tyr Ala Phe Ala Leu
                245                 250                 255

Ser Arg Gly Phe Gly Ser Gly Ile Ile Thr Ser Asn Ala Ser Met His
            260                 265                 270
```

-continued

```
Glu Cys Asn Thr Lys Cys Gln Thr Pro Leu Gly Ala Ile Asn Ser Ser
            275                 280                 285

Leu Pro Tyr Gln Asn Ile His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Ile Asp Gly Trp Tyr Gly Tyr His His
            340                 345                 350

Gln Asn Glu Gln Gly Ser Gly Tyr Ala Ala Asp Gln Lys Ser Thr Gln
            355                 360                 365

Asn Ala Ile Asn Gly Ile Thr Asn Lys Val Asn Thr Val Ile Glu Lys
    370                 375                 380

Met Asn Ile Gln Phe Thr Ala Val Gly Lys Glu Phe Asn Lys Leu Glu
385                 390                 395                 400

Lys Arg Met Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
            435                 440                 445

Lys Ser Gln Leu Lys Asn Asn Ala Lys Glu Ile Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asp Tyr Pro Lys Tyr Ser Glu Glu Ser Lys Leu Asn Arg
                485                 490                 495

Glu Lys Val Asp Gly Val Lys Leu Glu Ser Met Gly Ile Tyr Gln
                500                 505                 510
```

COMPOSITIONS OF INFLUENZA HEMAGGLUTININ WITH HETEROLOGOUS EPITOPES AND/OR ALTERED MATURATION CLEAVAGE SITES AND METHODS OF USE THEREOF

CROSS-REFERENCE TO RELATED APPLICATIONS

This application is a continuation of U.S. Ser. No. 15/556,555 having an international filing date of 2 Feb. 2017, which is the national phase of PCT application PCT/US2017/016251 having an international filing date of 2 Feb. 2017, which claims benefit of U.S. provisional application No. 62/290,894 filed 3 Feb. 2016. The contents of the above patent applications are incorporated by reference herein in their entirety.

INCORPORATION BY REFERENCE OF SEQUENCE LISTING

The present application is being filed along with a Sequence Listing in electronic format. The Sequence Listing is provided as a file entitled 758252000101SeqList.TXT, created 13 May 2019, size: 186,044 bytes. The information in the electronic format of the Sequence Listing is incorporated by reference in its entirety.

TECHNICAL FIELD

This invention is in the field of immunology and virology. More particularly it relates to compositions of recombinant influenza hemagglutinin (HA) proteins with altered and heterologous epitopes and/or altered maturation cleavage sites.[1]

[1] The following abbreviations are applicable. HA, hemagglutinin; NA, neuraminidase; NAbs, neutralizing antibodies; bNAbs, broadly neutralizing antibodies; TEV, tobacco etch virus; DNA, deoxyribonucleic acid; cDNA, complementary DNA; RNA, ribonucleic acid; kb, kilobase; kDa, kilo Dalton; CHO cells, Chinese hamster ovary cells; HEK 293 cells, human embryonic kidney 293 cells; VLP, virus-like particle; BEVS, baculovirus expression vector system; AcNPV, *Autographa californica* nuclear polyhedrosis virus; BmNPV, *Bombyx mori* nuclear polyhedrosis virus; TIPS, titerless infected-cells preservation and scale-up; BIIC, baculovirus infected insect cells; PCR, polymerase chain reaction; FBS, fetal bovine serum; PDB, Protein Data Bank which is on the World Wide Web at (rcsb.org/pdb/home/home.do); MOI, multiplicity of infection; MCS, maturation cleavage site; HPAI, high pathogenic avian influenza; HI, HA inhibition; WT, wild type; TIV, trivalent inactivated influenza vaccines; PBS, phosphate buffered saline.

BACKGROUND ART

Influenza, commonly known as "the flu", is an infectious respiratory disease caused by infection of human or zoonotic influenza viruses. Outbreaks of influenza occur annually during the cold months of each year, commonly known as "flu season". These annual epidemics cause 3-5 million cases of severe illness and up to 500,000 deaths worldwide, although most symptoms of influenza infections are mild (World Health Organization: Influenza (Seasonal) on the World Wide Web at who.int/mediacentre/factsheets/fs211/en/). Each century, there are several influenza pandemics when influenza viruses infect a large proportion of human population and inflict significant morbidity and mortality around the world. The 1918 Spanish flu pandemic that killed 3 to 5 percent of the world's population is the most deadly pandemic in recorded history.

Current Strategies to Elicit Stem Domain Reactive Antibodies

Elicitation of broadly neutralizing antibodies (bNAbs) against all influenza viruses has been the ultimate goal of flu vaccine design. Majority of the isolated bNAbs recognize conserved epitopes in the HA stem domain. However, antibodies elicited by natural influenza virus infection or current flu vaccines mostly recognize the antigenic sites that surround the receptor binding site in the HA globular head domain due to the immunodominance of these antigenic sites. These antibodies are generally strain-specific as a result of the high variability of these antigenic sites among influenza virus strains. Thus current flu vaccines do not induce universal immunity against flu viruses.

Hemagglutinin (HA) is an integral membrane glycoprotein. It is the most abundant protein in influenza virus lipid bilayer envelope. About 500 molecules of HA are estimated on the surface of a virion. HA is the only protein required for adsorption and penetration of virus into host cells. It binds to host cell receptors and enables fusion between the virion lipid envelope and the host cell membrane. Through its ability to bind host cell receptors, HA determines the host range of an influenza strain.

HA is synthesized as a single chain precursor named HA0 in the endoplasmic reticulum (Stevens, J., et al., *Science* (2006) 312:404-410). The HA0 precursor has a signal peptide at its N-terminus and a membrane anchor sequence at its C-terminus. The N-terminal signal peptide is removed during the process when HA is transported across and anchored into the host cell membrane. HA is assembled into trimers of identical subunits in the endoplasmic reticulum and is then exported to the cell surface via the Golgi network. HA0 is cleaved at the C-terminal end of the maturation cleavage site (MCS) by specific host trypsin-like protease and converts to the mature form consisting of two disulfide-bond linked polypeptides, HA1 and HA2. HA1 is the larger N-terminal portion and HA2 is the smaller C-terminal portion of HA0. HA2 has the transmembrane region with a short C-terminal intracellular tail and anchors the HA to the membrane. Each mature HA has a total molecular weight of about 70 kDa with HA1 about 45 kDa and HA2 about 25 kDa. The atomic structures of the extracellular portion of HAs from many influenza strains have been determined. The structural model of a mature HA is shown in FIGS. 1A-1B. All HAs, either as HA0 or the mature form, have the same overall trimeric structure with a globular head on a stem. Each HA monomer is anchored on membrane by a single C-terminal transmembrane region with a short hydrophilic cytoplasmic tail.

The globular head domain is made entirely of the HA1 and contains immunodominant epitopes. The stem domain is mostly made of the HA2 and contains conserved regions that are subdominant immunogenically. The globular head domain has an eight-stranded β-sheet structure at its core with surface loops and helices. The membrane proximal stem domain is composed of left-handed superhelix of a triple coiled-coil structure of residues from both HA1 and HA2. Each HA monomer has multiple glycosylation sites with a total carbohydrate of about 13 kDa of molecular weight or 19% of the total HA molecular weight. Most glycosylation is in the stem domain near the membrane surface. HA is also modified by palmitoylation of cysteine residues on the cytoplasmic tail (Veit, M., et al., *J. Virol* (1991) 65:2491-2500).

To circumvent the immunodominance of the globular head domain, immunogens have been designed based on the HA stem domain without the globular head domain (headless HAs). These attempts have been largely unsuccessful due to the difficulty of production of such molecules with proper tertiary structure (Krammer, F. and Palese, P. *Curr Opin Virol* (2013) 3:521-530; Eckert, D. M., and Kay, M. S., PNAS (2010) 107:13563-13564). HA2 by itself has been expressed in *E. coli* in soluble form that folds into its most stable post-fusion low-pH-induced conformation (Chen, J., et al., *PNAS* (1995) 92:12205-12209). By incorporating designed mutations to destabilize the low pH conformation of HA2, another HA2 construct (HA6) based on H3 HA was expressed in *E. coli* and refolded into the desired neutral pH pre-fusion conformation (Bommakanti, G., et al., *PNAS* (2010) 107:13701-13706). HA6 was highly immunogenic in mice and protected mice against the infection by homologous influenza A viruses. However, sera from HA6 immunized mice failed to neutralize virus in vitro, which could be due to limitation of the assay that only detect virus-neutralizing activity of the antibodies recognizing the globular head domain. Another "headless" HA stem domain construct with the HA2 and the region of HA1 in the stem domain has been described (Steel, J., et al., *mBio* (2010) 1:e00018-10). This immunogen protected mice against homologous influenza challenge and elicited antisera cross-reactive to heterologous HAs from within the same group. As with HA6, the antisera did not show neutralizing activity in vitro. These designs are all based on protein minimization by eliminating immunodominant regions.

Recently, through structure-based rational design and reiterative bNAb selection of construct libraries, stable trimeric H1 HA stem-only immunogens (headless mini-HAs) were made (Impagliazzo, A., et al., *Science* (2015) 349: 1301-1306; Yassing, H., M., et al., *Nat Med* (2015) 21:1065-1070; Patent application WO2014/191435_A1). These stem-only mini-HA immunogens elicited expected antibodies against HA stem domain. Mice and ferrets immunized with these mini-HA immunogens were protected from lethal challenge of highly pathogenic H5 virus. In addition, a mini-HA immunogen elicited H5 neutralizing antibodies in cynomolgus monkeys. These mini-HA immunogens were selected for their binding to specific bNAbs. The lengthy reiterative bNAb selection process needs to be repeated for a different type of bNAbs. Although conformations of the bNAb epitopes were preserved in these mini-HA immunogens, the overall structures were different from the stem domain of native HA. Due to these structural changes, it is unlikely these headless mini-HA immunogens can be assembled into influenza viruses or influenza virus-like particles (VLPs). In addition, these headless mini-HA immunogens do not have the receptor binding site for host cell binding.

Chimeric HAs have been designed to direct the host immune response to the stem domain. Most neutralizing antibodies induced by pandemic H1N1 infection were broadly cross-reactive against epitopes in the HA stem domain and globular head domain of multiple influenza strains (Wrammert, J., et al., *J Exp Med* (2011) 208:181-193). Immunization with HA derived from H5N1 influenza strains (a group 1 HA) that is not circulating in humans substantially increases HA stem-specific responses to group 1 circulating seasonal strains (Ellebedy, A. H., et al., *PNAS* (2014) 111:13133-13138; Nachbagauer, R., et al., *J Virol* (2014) 88:13260-13268; Whittle, J. R. R., et al., *J. Virol* (2014) 88:4047-4057). After each emergence of pandemic influenza virus strains in 1957, 1968, and 2009, existing seasonal virus strains were replaced in the human population by the novel pandemic strains.

It is hypothesized that exposure to new pandemic influenza virus strains with divergent globular head domains lead to affinity matured memory responses to the conserved epitopes in the stem domains (Palese, P. and Wang, T. T., *mBio* (2011) 2:e00150-11). In support of this hypothesis, engineered recombinant chimeric HA of H6, H9, or H5 globular head domain and H1 stem domain generated high titer stem-specific neutralizing antibodies (Pica, N., et al., *PNAS* (2012) 109:2573-2578; Krammer, F., et al., *J. Virol* (2013) 87:6542-6550). In these cases, the globular head domain of H1 HA was replaced by the globular head domain of H6, H9, or H5 from the same group 1 HA to which most of the human population is naïve. These replacements were made by replacing the H1 HA sequence between cysteine 52 and cysteine 277 of HA1 with the corresponding sequence of H6, H9, or H5. Cysteine 52 and cysteine 277 form a disulfide bond in the hinge region between the globular head domain and the stem domain. Similar chimeric HAs were made with H3 stem domain to develop vaccines for group 2 influenza strains (Krammer, F., et al., *J. Virol* (2014) 88:2340-2343; Margine, I., et al., *J. Virol* (2013) 87:10435-10446). Immunizing animals with these chimeric HAs induced stem-specific antibodies with broad neutralizing activity against each group of viruses. Human population has preexisting immunity to circulating H1 (group 1), H3 (group 2), and influenza B virus strains. Vaccination with a chimeric HA boosted antibody levels against the stem domains that are common to HAs of the circulating strains and the chimeric HA. Only a primary response was induced against the novel globular head domain on the chimeric HA to which humans are naïve. Subsequent boost with a second chimeric HA that possesses the same stem domain but a different head domain further increased stem-specific antibody levels. The results suggest changing the host exposure to the immunodominant epitopes in the globular head domain can increase the broadly protective immune responses against the immunosubdominant epitopes in the stem domain.

The six-amino-acid loop of antigenic Site B of A/WSN/33(H1N1) hemagglutinin can be replaced by the homologous antigenic Site B residues of HAs from A/Japan/57 (H2N2) and A/Hong Kong/8/68(H3N2) (Li, S., et al., *J. Virol* (1992) 66: 399-404). These replacements do not interfere with the receptor binding function of HA. Recombinant influenza viruses with these chimeric HAs were replicated in MDCK (Madin-Darby Canine Kidney Epithelial Cells) cell culture. Viruses with chimeric HAs of A/WSN/33(H1N1) and A/Hong Kong/8/68(H3N2) induced antibodies against both A/WSN/33(H1N1) and A/Hong Kong/8/68(H3N2). These results suggest that the immunodominant antigenic sites of a HA can be replaced by the homologous corresponding immunodominant antigenic sites of other HAs from different strains. These replacements change the antigenic specificity of the resulting chimeric HAs.

In the foregoing paragraphs, therefore, the immunodominant epitopes in one influenza strain were replaced by the homologous immunodominant epitopes from another strain.

Another strategy is to dampen the immunodominant epitopes and refocus the host immune response towards the stem domain. The immunodominant antigenic sites in the globular head domain can be shielded by introducing additional glycosylation sites for hyperglycosylation (Eggink, D., et al., *J. Virol* (2014) 88:699-704, Patent application US2014/0004149_A1). The hyperglycosylation in globular head domain did not change the binding affinity of stem-reactive antibodies. Immunization of mice with the hyperglycosylated HA induced high titers of stem-reactive antibodies and protection against morbidity and mortality upon challenge with distinct seasonal viruses. Patent application US2013/0315929_A1 disclosed another method to dampen the immunodominant epitopes in the globular head domain by replacing some residues of those epitopes with other amino acids with less likelihood of being part of an epitope. The results suggest shielding immunodominant epitopes in the globular head domain can increase the broadly protective immune responses against the immunosubdominant epitopes in the stem domain.

HA as Carrier to Present Foreign Epitopes

Influenza HA has been used as a carrier for epitopes of V3-loop of HIV-1 envelope protein. Insertion of immunodominant epitope peptides of 12 to 22 residues in length from HIV-1 envelope protein gp120 to the HA immunodominant antigenic site, either the Site A or Site B, produced chimeric HAs with individual HIV-1 epitope in the globular head domain. No residues of Site A and Site B were removed. The immunodominant HIV-1 epitopes were inserted into the sites. The chimeric HAs induced immune responses to the HIV-1 V3-loop epitope in animals (Kalyan, N. K., et al., *Vaccine* (1994) 12:753-760; U.S. Pat. No. 5,591,823_A; Li, S., et al., *J. Virol* (1993) 67:6659-6666). The immunogenicity of the inserted epitopes appeared to be enhanced by HA since a very low dose of a chimeric HA protein was sufficient to induce antibodies specific to the inserted epitope. These results suggest that immunodominant foreign epitopes from proteins other than HA can be inserted to the immunodominant antigenic sites of HA. These chimeric HA molecules with inserted foreign immunodominant epitopes can induce immune responses to the inserted foreign immunodominant epitopes.

DISCLOSURE OF THE INVENTION

This invention is directed to modified forms of influenza hemagglutinin protein, to vaccines, virus-like particles, and viruses that contain it as well as recombinant methods and materials for its production. In general, these modifications include replacement of the immunodominant regions of the globular head domain of HA protein with alternative epitopes for generating antibodies and/or modification of the maturation cleavage site (MCS) in the stem domain of the HA protein. Cleavage of HA0 between MCS and the fusion peptide to generate the free N-terminus of HA2 is essential for cell entry. By altering the MCS so as to prevent its cleavage by animal proteases, a virus where the MCS has already been cleaved permits infection of host cells where the virus may multiply, but its progeny are uninfective. Thus, the presence of any epitopes including those occupying the immunodominant sites is amplified without further infection of the host by the progeny viruses.

In one aspect, the invention is directed to a flu vaccine which comprises a modified HA or a virus or virus-like particle which contains it, wherein an immunodominant region of the HA protein contains a conserved alternative epitope of the same influenza strain or another influenza strain inserted into this region. This provides a more successful immunogenic form of the inserted alternative epitope that is immunosubdominant in its native position. Alternative epitopes are those not derived from the globular head domain of other HAs. Typically they are from the HA stem domains or from non-HA influenza proteins, such as M2.

In another aspect, the invention is directed to a modified influenza virus (which could also be used as a vaccine) which has been modified to contain an MCS that is not cleaved by animal proteases. As noted above, this permits amplification of the virus without engendering infective forms thereof. Such a virus can be further modified by replacing one or more immunodominant regions with an alternative or heterologous epitope which may be an influenza epitope or a foreign epitope including, for example, epitopes characteristic of other viruses, bacteria or tumor associated antigens.

In still other aspects, the invention is directed to recombinant materials and methods for preparing the proteins, viruses or virus-like particles of the modified HA protein and methods to generate antibodies using these proteins, virus-like particles or modified viruses.

BRIEF DESCRIPTION OF THE DRAWINGS

FIG. 1A shows HA trimer with one HA monomer in ribbon drawing and the other two in backbone drawing. The orientation with respect to the membrane, the position of the globular head domain, and the stem domain are indicated. HA1 is shown as light shaded ribbon and HA2 is shown as dark shaded ribbon. FIG. 1B shows the single HA monomer with the positions of HA1 and HA2, as well the N- and C-termini of HA1 and HA2. The fusion peptide is circled.

FIG. 2A shows a ribbon drawing as in FIG. 1. The H3 HA immunodominant antigenic sites A, B, C, D, and E are shown in dark shades. FIG. 2B is the top view of FIG. 2A above the globular head domain distal to the membrane.

FIG. 3A shows a ribbon drawing as in FIG. 1. The H1 HA immunodominant antigenic sites Ca1, Ca2, Cb, Sa, and Sb are shown in dark shades. FIG. 3B is the top view of FIG. 3A above the globular head domain distal to the membrane. Many of these immunodominant antigenic sites surround the host cell receptor binding site as indicated by an arrow.

FIG. 4A is a schematic drawing of nucleic acid features of the constructs. Positions of restriction sites for subcloning are labeled. FIG. 4B is a schematic drawing of the protein features of the constructs in relative proportion to the nucleic acid shown in FIG. 4A. GP67ss represents the GP67 secretion signal (signal peptide) at the N-terminus. HA1 represents HA HA1. MCS represents HA maturation cleavage site which is part of HA1. HA2 represents HA HA2. TEV represents TEV cleavage site. Foldon represents foldon sequence. His represents 10-histidine-tag (10×His-tag) at the C-terminus.

FIG. 6A shows the model of CR8020Sa4. FIG. 6B shows the model of CR8020Ca.

MODES OF CARRYING OUT THE INVENTION

Figure 1A:
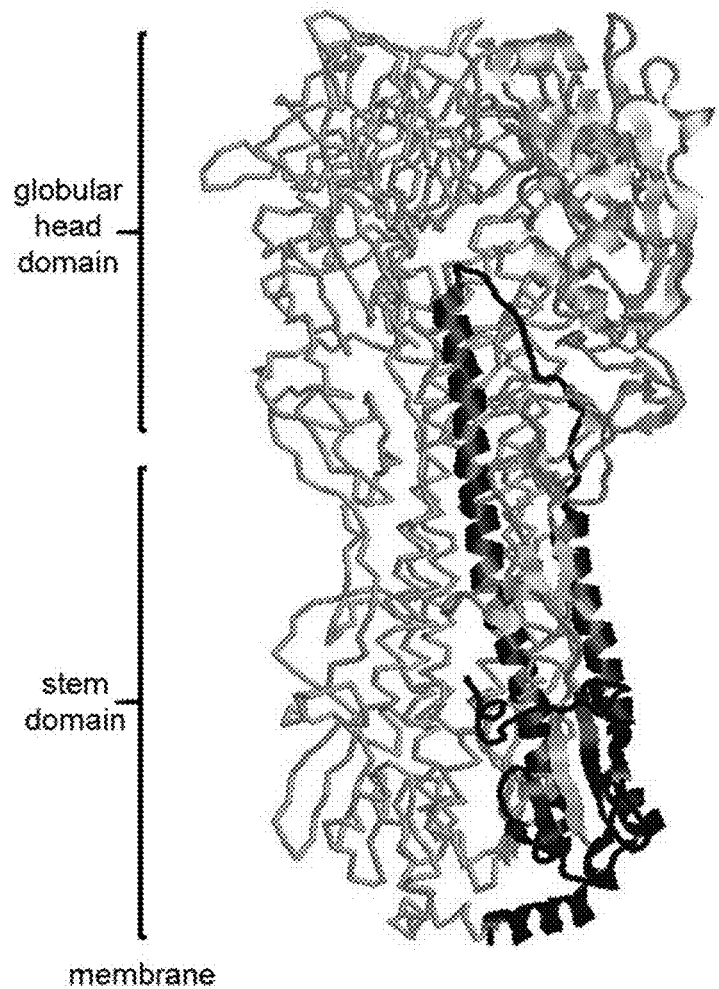
FIGS. 1A-1B illustrate the X-ray crystal structure of the extracellular portion of a mature HA of A/California/07/2009, a swine origin influenza A virus H1N1 strain (PDB: 3LZG). This structure is used to guide the construct designs in this invention. The peptide sequence of this HA is used for making the parental wild type (WT) H1 HA construct.
Figure 1B:
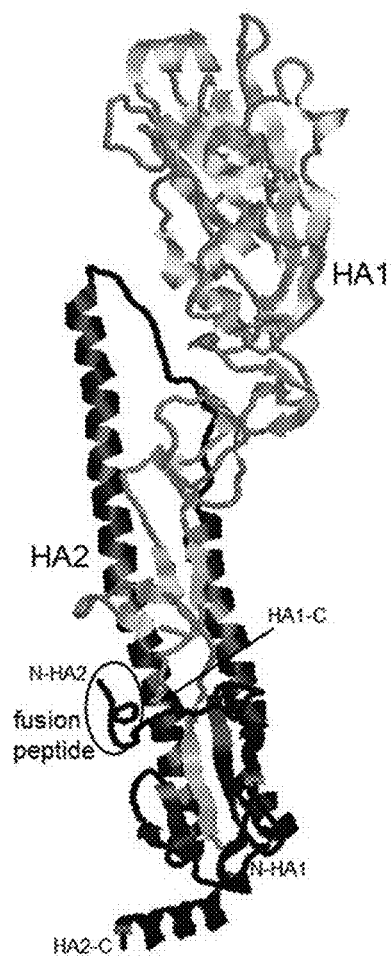

As this invention is directed to modifications of HA protein, further description of this protein and its function in addition to that provided above may be helpful.

Protease cleavage of HA0 is a prerequisite for the infectivity of influenza A viruses. The distribution of these proteases in the host is one of the determinants of tissue tropism and, as such, pathogenicity. Several trypsin-like proteases have been identified in respiratory track and lung that cleave majority of HAs with monobasic maturation cleavage sites (Kido, H., et al., *J. Biol Chem* (1992) 267: 13573-13579; Peitsch, C., et al., *J. Virol* (2014) 88:282-291; Zhirnov, O., P., et al., *J. Virol* (2002) 76: 8682-8689). These proteases are serine proteases. One of them is trypsin-like protease Clara, first isolated from rat bronchiolar epithelial Clara cells. Narrow tissue distribution of these proteases that cleave HA0 restricts influenza virus infection to the respiratory tracks and lungs in mammals.

The proteases responsible for HA maturation are not yet well characterized. Like trypsin, these proteases cleave the peptide bond C-terminal to a basic residue such as arginine (R) or lysine (K). The maturation cleavage site (MCS) is located at the C-terminal end of HA1 and cleavage at the C-terminus of MCS is essential for infectivity.

A polybasic sequence in the maturation cleavage sites of H5 and H7 subtypes leads to cleavage susceptibility by a broader range of cellular proteases such as furin and subtilisin-type proteases, which correlates with broader tissue tropism and higher pathogenicity of these viruses in mammals (Stieneke-Gröber, A., et al., *EMBO J* (1992) 11:2407-2414; Maines, T. R., et al., *J. Virol* (2005) 79:11788-11800).

Many highly pathogenic avian influenza (HPAI) subtypes are H5 and H7. During HPAI outbreaks in human, reported case-fatality rates are higher than those of pandemic and seasonal influenza viruses (Morens, D. M., et al., *Nature* (2012) 486:335-340). These polybasic sequences in the MCS also lead to viral replication in multiple organs of avian species, resulting in high mortality in these avian species.

The HAs of seasonal flu viruses and nonpathogenic avian influenza viruses are cleaved extracellularly by specific proteases in respiratory tract and lung which limit their tissue tropism. On the other hand, the HAs of highly pathogenic viruses are cleaved intracellularly by ubiquitously occurring proteases. These highly pathogenic viruses undergo multiple-cycle replication in various tissues to cause systemic infections (Steinhauer, D. A., *Virus. Virol* (1999) 258:1-20; Taubenberger, J. K., *PNAS* (1998) 95:9713-9715). The 1918 pandemic strain of human influenza virus also utilizes a broad range of cellular proteases and use its neuraminidase (NA) to recruit plasminogen for HA cleavage (Goto, H. and Kawaoka, Y. *PNAS* (1998) 95:10224-10228; Chaipan, C., et al., *J. Virol* (2009) 83:3200-3211).

Cleavage of HA0 generates HA2 with a new free N-terminus which is essential for virion fusion with host cells. The cleaved form is the mature form of HA with full function of receptor binding and membrane fusion. HA0 has the ability to bind receptors but does not mediate membrane fusion. Both the precursor and the mature form of HA exist on the surface of virions. Viruses with only HA0 have no fusion activity and do not cause infection.

The N-terminal twelve residues of HA2 is called the "fusion peptide" (Skehel, et al., *Biochem Soc Trans* (2001) 29:623-626). The fusion peptide has a hydrophobic sequence. In HA0, MCS and the fusion peptide form a surface loop. After cleavage, the newly generated N-terminal fusion peptide inserts into the HA trimer interface. Following binding to host cell receptors, the attached influenza virions are endocytosed by the host cells into endosomes. The fusion potential of mature HA is activated at endosomal pH, between pH 5 and 6 depending on the particular influenza virus strain. Extensive changes in HA structure at low pH result in extrusion of the fusion peptide towards the cell membrane. Insertion of fusion peptide into the host endosomal membrane leads to fusion of the surrounding host endosomal membrane with the viral membrane containing the C-terminal membrane anchor region of HA. Fusion releases the viral RNA segments into the cytoplasm of the host cell to enter into the host cell nucleus, where viral replication occurs.

Figures 3A, 3B:
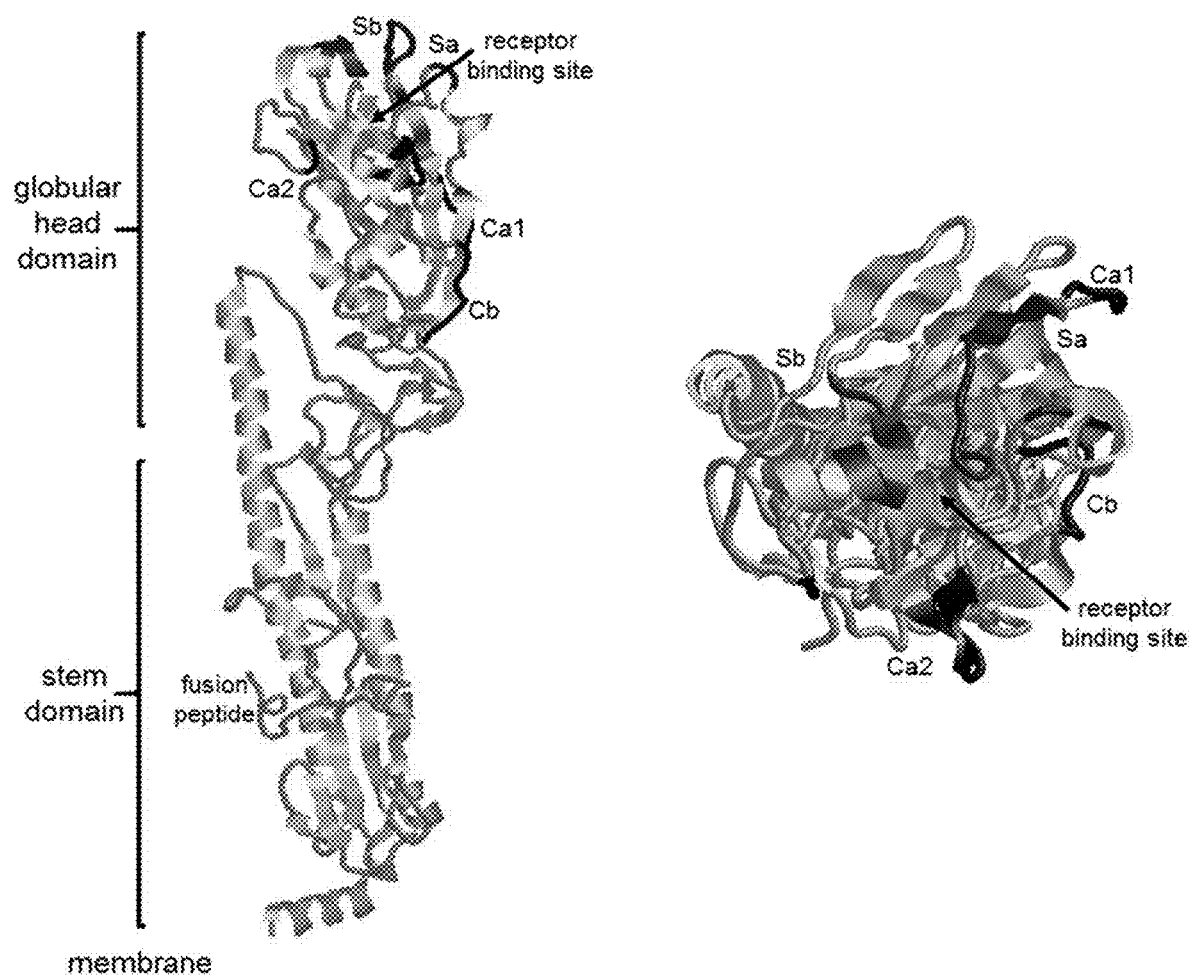
FIGS. 3A-3B illustrate the approximate positions of the immunodominant antigenic sites of H1 HA mapped to the H1 HA monomer of A/California/07/2009.

HA determines the host range of an influenza virus strain. HA binds to terminal sialic acid of host cell surface glycoproteins and glycolipids. HAs from human influenza strains bind almost exclusively to sialyloligosaccharides terminated by SAα2,6Gal, whereas HA from avian and equine influenza strains bind SAα2,3Gal. Human has mostly SAα2,6Gal sialyloligosaccharides and avian species have mostly SAα2,3Gal sialyloligosaccharides. As schematically shown in FIGS. 3A-3B, the host receptor binding sites on HA are located in the globular head domain that is exclusively made of HA1. The receptor specificity of influenza virus HA has been well characterized. The amino acid residues responsible for the recognition of SAα2,6Gal or SAα2,3Gal have been mapped. It has been shown that a single amino acid residue substitution in the receptor binding pocket changes the receptor binding specificity (Rogers, G. N., et al., *Nature* (1983) 304:76-78). Different isolates of 1918 influenza pandemic virus had different receptor binding specificity as a result of a single amino acid substitution in the receptor binding site of HA (Glaser, L., et al., *J Virol* (2005) 79:11533-11536). The strain A/South Carolina/1/18 HA preferentially binds the human cellular receptor SAα2,6Gal, whereas the strain A/New York/1/18 HA binds both human cellular receptor SAα2,6Gal and avian cellular receptor SAα2,3Gal, revealing the dynamic nature of host adaptation of influenza viruses.

Even though a single mutation in the receptor binding site of HA changes the receptor binding specificity from avian to human, efficient transmission of H5 avian influenza virus strain in human requires several other changes in HA outside the receptor binding site and changes in other influenza proteins (Imai, M., et al., *Nature* (2012) 486:420-428; Herfst, S., et al., *Science* (2012) 336:1534-1541; Chen, L-M., et al., *Virol* (2012) 422:105-113; Russell, C. A., et al., *Science* (2012) 336:1541-1547). Together with other changes, as few as four amino acid substitutions in H5 HA are sufficient to enable the transmission of mutant avian H5 virus among ferrets through respiratory droplets. In addition to understanding of influenza virus transmission across species, these studies established laboratory procedures to study non-mammalian influenza virus transmission in mammals, which can be used to evaluate universal influenza vaccine candidates.

Description of Anti-Flu Antibodies and Antigenic Sites of HA

As the most abundant protein of influenza virus lipid bilayer envelope, HA is the major antigen of influenza virus and harbors the primary epitopes for neutralizing antibodies. Most human anti-flu antibodies are against HA and NA. Sixty percent (60%) of the influenza-reactive antibodies elicited by vaccination react to HA (Wrammert, J., et al., *Nature* (2008) 453:667-671). Majority of HA-reacting antibodies recognize the antigenic sites that surround the receptor binding site in the globular head domain. Some of these antibodies are virus-neutralizing antibodies. These neutralizing antibodies (NAbs) generally interfere with HA binding to host cells and show HA inhibition (HI) activity. They are generally strain-specific due to the high variability of these antigenic sites, and thus lack the much-desired broad neutralizing activity (Wang, T. T., and Palese, P., *Nat Struct Mol Biol* (2009) 16:233-234).

The widespread infection of influenza viruses is the result of the ability of the virus to alter its antigenic properties. The changes of antigenic properties of influenza viruses are the result of the low fidelity replication of the viral genome by the error-prone viral RNA-dependent RNA polymerase complex. The high mutation rate leads to antigenic drift, a gradual change of antigenic properties of HA. Antigenic drift occurs in all types of influenza viruses. Sequence analyses of HA genes show that most of the changes in amino acid sequences are located in the HA1 even though silent nucleic acid sequence changes are spread over the entire HA gene (Palese, P., and Young, J. F., *Science* (1982) 215:1468-1474). HA2 is more conserved than HA1.

The segmented nature of viral genome also leads to re-assortment of viral genome segments when viruses of two different strains co-infect a host at the same time. A new strain of virus emerges from this re-assortment with different viral surface proteins that lead to antigenic shift, an abrupt change of antigenic properties of HA. Antigenic shift occurs only in Influenza A viruses. Antigenic drift and antigenic shift enable influenza viruses to escape from neutralization by existing antibodies.

H3 Influenza

The first detailed structure of an influenza HA determined over 35 years ago shed light on the antibody-binding sites of HA and presents a molecular explanation to antigenic drift and antigenic shift (Wilson, I. A., et al., *Nature* (1981) 289:366-373; Wiley, D. C., et al., *Nature* (1981) 289:373-378; Wiley, D. C., and Skehel, J. J., *Ann Rev Biochem* (1987) 6:365-394).

Figure 2A:
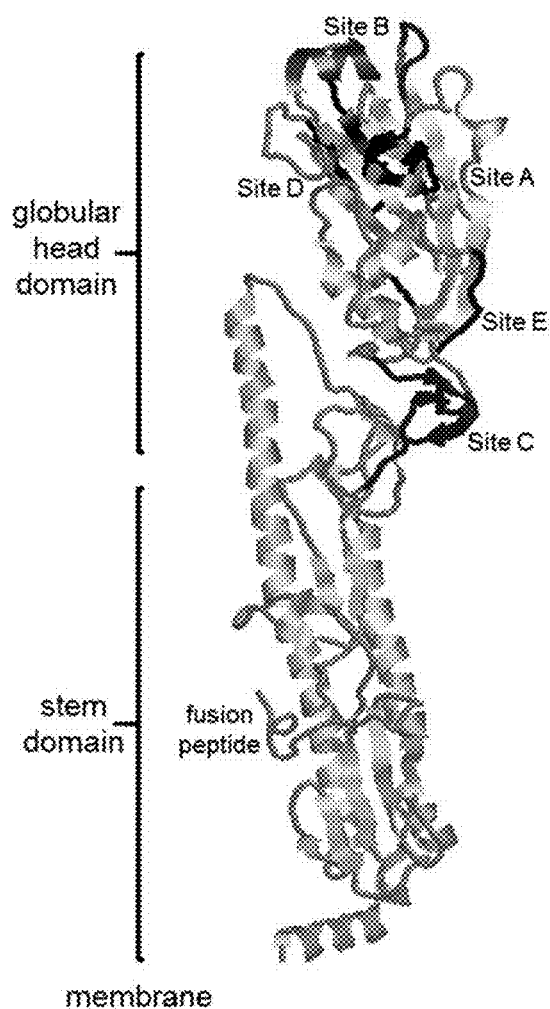
FIGS. 2A-2B illustrate the approximate positions of the immunodominant antigenic sites of H3 HA mapped to the H1 HA monomer of A/California/07/2009.
Figure 2B:
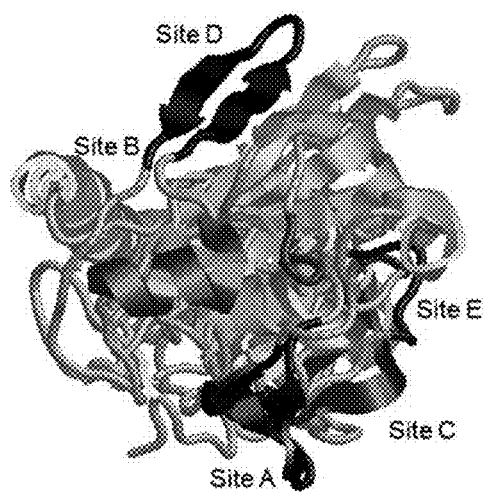
Figure 5:
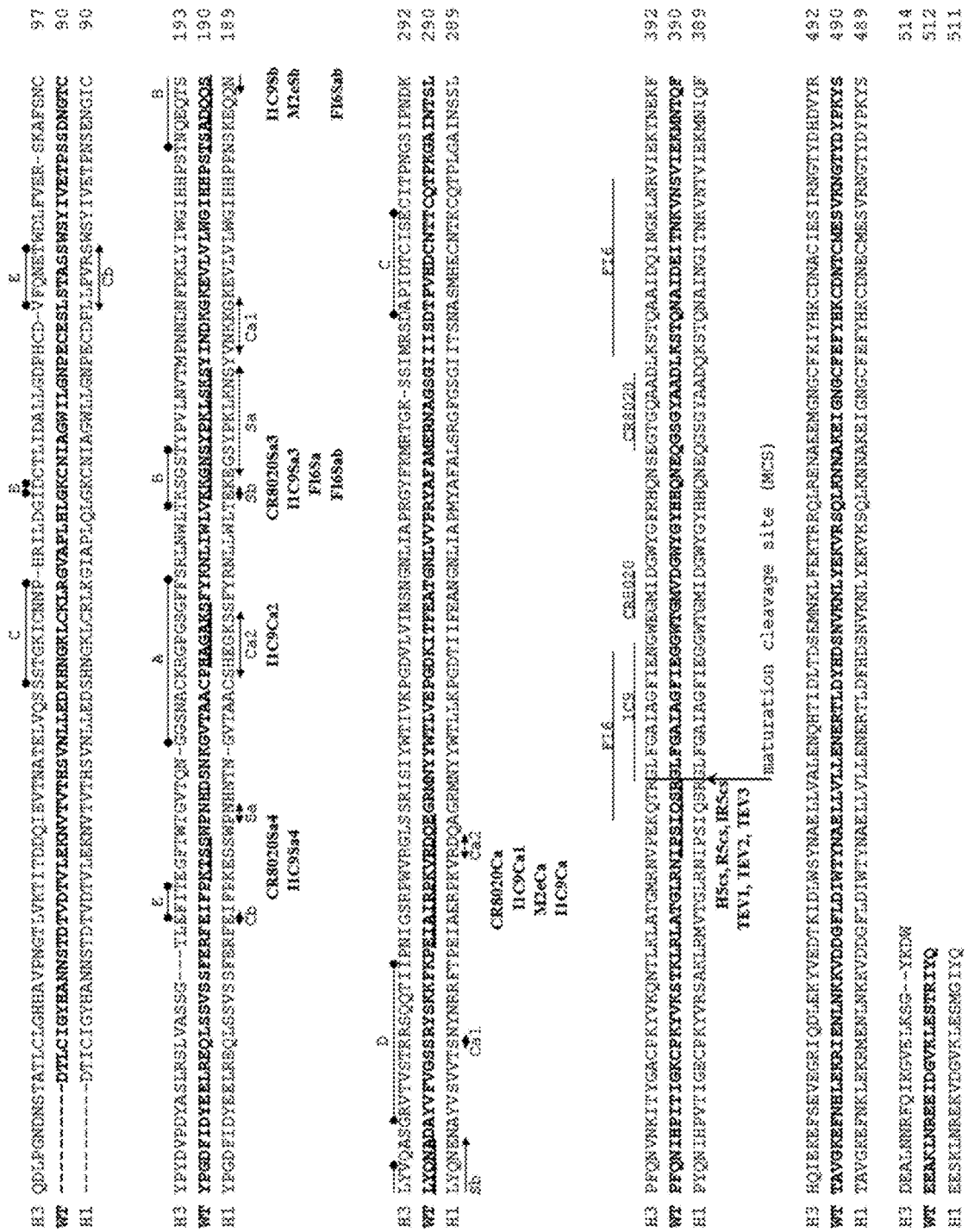
FIG. 5 contains sequences H3 (SEQ ID NO: 63), WT (SEQ ID NO: 64) and H1 (SEQ ID NO: 65) and illustrates the positions where the heterologous epitopes are placed in the HA globular head domain and where the altered maturation cleavage sites are. The parental construct peptide sequence (WT) is aligned with HA sequences of H3 (A/Aichi/2/1968 H3N2) and H1 (A/Puerto Rico/8/1934 H1N1). The amino acid positions of each sequence are labeled on the right based on HA0 numbering with the first residue after signal sequence removal as position 1. The maturation cleavage site (MCS) is indicated by an arrow and a vertical line. The immunodominant antigenic sites A, B, C, D and E of H3 HA are marked above the H3 sequence. The immunodominant antigenic sites Ca1, Ca2, Cb, Sa and Sb of H1 HA are marked below the H1 sequence. The underlined sequences in WT are replaced by the heterologous epitopes indicated below the sequences. Altered maturation cleavage sites are indicated below the maturation cleavage site (MCS). The native immunosubdominant antigenic sites for broadly neutralizing antibodies (bNAbs), FI6, 1C9, and CR8020, are marked by lines above the sequences, respectively.

Comparison of HA sequences of antigenically distinct viruses identified immunodominant antigenic sites in the globular head domain of H3 HA, a group 2 subtype HA. The descriptions of immunodominant antigenic sites of H3 HA are substantiated by others (Both, G. W., et al., *J. Virol* (1983) 48:52-60). The approximate positions of these antigenic sites in a HA structure are schematically shown in FIGS. 2A-2B. The sequence positions of these antigenic sites are shown in FIG. 5. Site A is located in the surface loop of residues 133 to 148 of the HA of A/Aichi/2/1968 H3N2 strain (numbering as H3 in FIG. 5). This loop, known as the 140-loop, projects from the globular head domain and is on the lower rim of the receptor binding pocket. Site B is located on the top of the globular head domain and comprises the surface α helix of residues 187 to 196 and adjacent surface loop of residues 155 to 160 along the upper rim of the receptor binding pocket. Site C surrounds the disulfide bond between Cys52 and Cys277. Crossing of the loop (residues 46 to 55) centered at Cys52 and the loop (residues 271 to 280) centered at Cys277 forms a bulge at the hinge between the globular head domain and the stem domain. Site D resides in the interface region between the HA monomer subunits of an HA trimer. It centers at two β-strands of residues 200 to 214 in the eight-stranded β-sheet structure in the core of the globular head domain. Residues at the turns of the other β-strands may also be part of Site D. Site D is mostly buried in the HA trimer interface. It is not clear how Site D functions as an antigenic site. Site E is located between Site A and Site C on the side of the globular head domain and is made of surface loops of residues 62 to 63, residues 78 to 83, and the β-strand of residues 119 to 122 on the edge of the eight-stranded β-sheets. Together these residues of Site E form a continuous surface on the side of the globular head domain. Comparing the amino acid substitutions and antigenic properties of influenza viruses that emerged during the period from 1968 to 2003 showed that substitutions responsible for major antigenic changes were located exclusively in Site A and Site B (Smith, D. J., et al., *Science* (2004) 305:371-376; Koel, B. F., et al., *Science* (2013) 342:976-979). Substitutions in Sites C, D and E appeared to cause minor antigenic changes. The results suggest that most strain-specific neutralizing antibodies bind to Site A and Site B in the periphery of the receptor binding site of the globular head domain.

H1 Influenza

Genetic analyses of antigenically distinct group 1 H1 HA of viral strain A/PR/8/34 identified distinct antigenic sites in the globular head domain, termed Ca1, Ca2, Cb, Sa and Sb sites (Caton, A. J., et al., *Cell* (1982) 31:417-427; Gerhard, W., et al., *Nature* (1981) 290:713-717). The approximate positions of these antigenic sites in the HA structure are schematically shown in FIGS. 3A-3B. The sequence positions of these antigenic sites are shown in FIG. 5. Ca1 site is located at the turns of the β-strands of the eight-stranded β-sheet structure. One of the turns of residues 165 to 169 (numbering as H1 in FIG. 5) is surface exposed. Residue 207 of Ca1 site is at the turn connecting the two β-strands corresponding to the Site D of H3 HA. Ca1 site of H1 HA generally corresponds to Site D of H3 HA. Ca2 site is also made of two segments that are separated in the primary structure but together in the tertiary structure. One segment of Ca2 is in the surface loop of residues 136 to 141 at the corresponding position of the Site A of H3 HA. Another segment of Ca2 is made of residues 220 to 221 on a long surface loop. Ca2 site is on the opposite side of Ca1 in the globular head domain of a HA monomer but is adjacent to Ca1 site of another HA monomer in a HA trimer. Ca1 site of one HA monomer forms a continuous surface with the Ca2 site of another HA monomer in the trimer structure. Cb site is a linear epitope of residues 70 to 75 that form a surface loop next to the eight-stranded β-sheet structure. It corresponds to Site E of H3 HA. Sites Sa and Sb can be considered as subsites that correspond to Site B of H3 HA. Site Sa of residues 154 to 163 overlaps with the loop corresponding to Site B loop of H3 HA. Another segment of Sa site is a nearby turn of residues 124 to 125. Site Sb corresponds to Site B α-helix of H3 HA and mostly has the α-helix residues 188 to 194.

Broadly Neutralizing Antibodies and Conserved Epitopes

Natural influenza virus infection or vaccination with trivalent inactivated influenza vaccines (TIV) also elicit low levels of antibodies against conserved HA epitopes that are mostly located in the membrane proximal stem domain (Ellebedy, A. H., et al., *PNAS* (2014) 111:13133-13138). These antibodies recognize epitopes conserved among many strains of influenza viruses. Those that provide protection against several strains are termed broadly neutralizing antibodies (bNAbs). These bNAbs generally do not have HA inhibition activity and do not prevent HA binding to host cell surface receptors. The first cross-strain antibodies C179 has been characterized over 20 years ago (Okuno, Y., et al., *J. Virol* (1993) 67:2552-2558). It recognizes a conformational epitope of residues 318 to 322 (TGLRN) of HA1 and residues 47 to 58 (GITNKVNSVIEK) of HA2 that are conserved among H1 and H2 strains. C179 inhibits the fusion activity of HA and thus results in virus neutralization.

Many bNAbs have been detected or isolated from patients infected with influenza viruses (Ekiert, D. C., and Wilson, I. A., *Curr Opin Virol* (2012) 2:134-141). The bNAbs have been demonstrated to neutralize group 1, group 2, or both group 1 and group 2 influenza A viruses. Many of the antigenic epitopes recognized by bNAbs have been identified and characterized. These epitopes are either a linear segment of HA sequence or conformational epitopes with multiple linear segments of HA sequence. Many of the epitopes to bNAbs are located in the less variable stem domain of HA proteins. These epitopes include but are not limited to the fusion peptides and the peptide sequences around the MCS.

Many bNAbs and their epitopes have been structurally characterized. For example, bNAb FI6 recognizes residues of the MCS and the fusion peptide in HA0 (Corti, D., et al., *Science* (2011) 333:850-856). Peptide mapping of HA identified two peptides as FI6 epitopes, RKKRGLFGAIAGFIE consisting of the MCS and most of the fusion peptide and KESTQKAIDGVTNKVNS of a helix coiled-coil peptide in HA2. The proposed neutralization mechanism of FI6 is to inhibit membrane fusion as well as to prevent HA maturation by blocking access of protease to the MCS of HA0. Another bNAb F10 recognizes a conformational epitope around the fusion peptide in the mature form of HA (Su, J., et al., *Nat Struct Mol Biol* (2009) 16:265-273). F10 inhibits all group 1 influenza A viruses presumably by preventing membrane fusion.

Monoclonal bNAb 1C9 inhibits cell fusion in vitro (U.S. Pat. No. 8,540,995; Prabhu, N., et al., *J. Virol* (2009) 83:2553-2562). 1C9 recognizes a linear epitope of GLFGA-IAGF, the N-terminus of the fusion peptide of the H5 HA2 of HPAI H5N1 (Immune Epitope Database web address: iedb.org/assay details.php?assayId=1599077). 1C9 shows protection in mice against infection by highly pathogenic avian influenza (HPAI) H5N1 virus. Monoclonal bNAbs have also been isolated from memory B cells (Hu, W., et al., *Virol* (2013) 435:320-328). Several of these monoclonal antibodies recognize a linear epitope of FIEGGWTGMVDGWYGYHH of HA2 from 2009 pandemic H1N1 influenza virus. This epitope is C-terminal to the 1C9 epitope of the fusion peptide. The sequences of the 14 residues of HA fusion peptides are highly conserved across influenza A and B viruses.

The conserved nature of HA fusion peptides has been explored to develop universal influenza vaccine. A peptide conjugate vaccine, based on the highly conserved sequence of the HA0 of the influenza B virus that includes the last 9 amino acid residues of HA1 that contains the MCS and the fusion peptide of HA2 at both sides of the scission bond, elicited a protective immune response against lethal challenge with virus strains of antigenically distinct lineages of influenza B viruses (Bianchi, E., et al., *J. Virol* (2005) 79:7380-7388).

Monoclonal bNAb CR6261 recognizes a highly conserved region in HA2 helix A and HA1 residues in the stem domain (Ekiert, D. C., et al., *Science* (2009) 324:246-251). CR6261 neutralizes group 1 influenza viruses by preventing conversion of HA to the post-fusion conformation. CR6261 belongs to bNAbs that use the same $V_H$1-69 germline antibody heavy chain. Another $V_H$1-69 monoclonal antibody, CR8020 neutralizes group 2 influenza viruses. CR8020 binds HA at the base of the stem domain in close proximity (~15 to 20 Å) to the membrane, analogous to those antibodies against HIV that recognize the membrane-proximal external region (MPER) from the HIV gp41 subunit (Ekiert, D. C., et al., *Science* (2011) 333:843-850). The two main components of CR8020 epitope consist of the C-terminal portion (HA2 residues 15 to 19, EGMID of H3) of the fusion peptide and the outermost strand (HA2 residues 30 to 36, EGTGQAA of H3) of the 5-stranded β sheet near the base of the stem domain. These two components are 10 residues apart in the primary structure of H3. Most bNAbs that bind to the stem domain of HA neutralize either group 1 (H1, H2, H5, H6, H8, H9, H11, H12, H13, and H16) or group 2 (H3, H4, H7, H10, H14, and H15) of HAs of influenza A viruses. These antibodies do not inhibit HA binding to host cells but may prevent fusion of viral membrane and host cell membrane.

The HA receptor binding site is a pocket at the top of the globular head domain (Wilson, I. A., et al., *Nature* (1981) 289:366-373; Wiley, D. C., and Skehel, J. J., *Ann Rev Biochem* (1987) 56:365-394). This pocket is formed by amino acid residues highly conserved across many influenza strains. The rim of the pocket is formed by the immunodominant antigenic sites, such as Site A and Site B in H3 as described above. Cloning of human monoclonal antibodies (mAbs) from healthy human subjects identified bNAbs that recognize conserved residues in close proximity to the receptor binding site in the globular head domain of HA from H1, H2, and H3 strains (Krause, J. C., et al., *J. Virol* (2011) 85:10905-10908; Krause, J. C., et al., *J. Virol* (2012)

86:6334-6340). Structural studies revealed that at least some of these bNAbs mimic the interaction of the sialic acid to the receptor binding pocket (Whittle, J. R. R., et al., *PNAS* (2011) 108:14216-14221; Ekiert, D. C., et al., *Nature* (2012) 489:526-532).

Stem-reactive antibodies are rare in natural infection and even less in immunization with current seasonal flu vaccines. Only a subset of these antibodies are neutralizing antibodies. Due to the conserved nature of the stem domain, most of the neutralizing antibodies are bNAbs. Cloning from antibody libraries made from human subjects can now routinely identify these rare broadly neutralizing stem-reactive antibodies (Kashyap, A. K., et al., *PNAS* (2008) 105: 5986-5991; Wrammert, J., et al., *Nature* (2008) 453:667-671). The rare occurrence of these stem-reactive antibodies leads to the hypothesis that these epitopes in the stem domain are immunosubdominant whereas the epitopes in the globular head domain are immunodominant to which most antibodies are directed (Krammer, F., and Palese, P., *Nature Rev Drug Disc* (2015) 14:167-182). Repeated exposure to prevalent seasonal flu viruses or immunization with seasonal flu vaccines leads to production of antibodies against the immunodominant antigenic sites in the globular head domain. It has been suggested that the presence of the immunodominant epitopes in the globular head domain may skew secondary responses away from the stem domain (Russell, C. J., *N Engl J Med* (2011) 365:1541-1542). Individuals who have been infected with current strains or vaccinated against them may have a harder time mounting a universal response than those who are immunologically naïve.

M2 Protein and its Epitope

M2 is a single-pass transmembrane protein that forms a homotetramer proton channel in the viral envelope (Lamb. R. A., et al., *Cell* (1985) 40:627-633; Pielak, R. M., and Chou, J. J., *Biochim Biophys* Acta (2011) 1808:522-529). It exists in much lower abundance compared to HA (1:10 to 1:100 ratio of M2:HA) in the viral envelope. M2 proton channel function is important to regulating the pH of viral interior for releasing viral proteins into the cytosol of host cells and to regulating the pH of the Golgi lumen for HA transport to the cell surface. Influenza A virus M2 (AM2) protein has 97 residues with an extracellular N-terminal domain of residues 1 to 23 known as M2e, a transmembrane (TM) domain of residues 24 to 46, and an intracellular C-terminal domain of residues 47 to 97. The TM domains from four M2 molecules form a four-helix bundle that functions as a pH-sensitive proton channel to regulate pH across the viral membrane during cell entry and across the trans-Golgi membrane of infected cells during virus assembly and exit. The large cytoplasmic domain is crucial for a stable tetramer formation and plays a role in virus assembly, through its association with the M1 protein of virion inner shell. Except for the HXXXW sequence motif in the TM domain that is essential for proton channel function, the M2 proteins of influenza A, B and C viruses share almost no sequence homology. However, the 10 N-terminal extracellular residues of AM2 are conserved in all influenza A viruses.

The influenza A virus M2 (AM2) is the target of the antiviral drugs amantadine and rimantadine which block the AM2 proton channel. The drug rimantadine, which stabilizes the closed state of the proton channel, binds to a lipid-facing pocket near the C-terminal end of the channel domain. Amantadine is an antiviral drug with activity against influenza A viruses, but not influenza B viruses. The use of these channel blockers has been discontinued due to widespread drug resistance as a result of mutations in the channel domain of AM2. Many of these mutations give rise to somewhat attenuated viruses that are less transmissible than wild type (WT) viruses. These drug resistant mutants can revert to WT in the absence of drug selection pressure.

M2 protein is an integral membrane protein expressed abundantly on the surface of host cells infected with influenza viruses (Lamb, R. A., et al., *Cell* (1985) 40:627-633). It is suggested that M2 is a cell surface antigen for cytotoxic T lymphocyte (CTL) response to influenza virus. Infection of influenza A viruses only elicit low titers of antibodies against M2 (Feng, J., et al., *Virol J* (2006) 3:102-115). The high degree of structural conservation of M2e could in part be the consequence of a poor M2e-specific antibody response and thus the absence of pressure for change. Anti-M2 antibody responses were more robust among individuals with preexisting antibodies to M2 protein (Zhong, W., et al., *J. Infect Dis* (2014) 209:986-994). The anti-M2 antibodies induced as a result of infection with 2009 pandemic H1N1 influenza A virus were cross-reactive to M2 protein of seasonal influenza A viruses. Treating mice with anti-M2e antibodies significantly delayed progression of the disease and led to isolation of M2e escape mutants, suggesting the potential of using M2e as a vaccine against influenza A virus infection (Zharikova, D., et al., *J. Virol* (2005) 79:6644-6654).

A DNA vaccine based on the fusion of M2e with HA has been described (Park, K. S., et al., *Vaccine* (2011) 29:5481-5487). This fusion protein has one human M2e peptide and one avian M2e peptide positioned at the N-terminus of HA protein through a 20-residue linker between each other. The expression of the encoded M2e-HA fusion protein was confirmed. Mice immunized with the M2e-HA fusion DNA vaccine showed enhanced T cell response to M2e and complete protection from lethal challenge of heterologous avian influenza virus.

A recombinant fusion protein comprising of four tandem repeats of M2e genetically fused to the C-terminus of *Mycobacterium tuberculosis* HSP70 (mHSP70) protein showed protection against multiple strains of influenza viruses in mice (Ebrahimi, S. M., et al., *Virology* (2012) 430:63-72). The M2e peptide, SLLTEVETPIRNEWGCRC-NDSSD, has been conjugated to a cationic liposome delivery vehicle along with peptides from other influenza proteins and the BM2, the homolog of M2e of Influenza B virus as vaccine (Patent Application US2010/086584_A1). The vaccine elicited immune response against M2e in mice. Mice vaccinated with the M2e peptide containing vaccine were protected from lethal influenza virus challenge. An inactivated influenza vaccine supplemented with M2e VLP conferred improved and long-lasting cross protection against antigenically different influenza A viruses in mice (Song, J-M., et al., *PNAS* (2011) 108:757-761).

Modification of Immunodominant Regions

This invention includes genetically modified recombinant influenza hemagglutinin (HA) genes and proteins that result from replacing the immunodominant regions of the globular head domain of HA with alternative epitopes or inserting the alternative epitopes therein to direct the host immune response to these epitopes. Some of these epitopes are recognized by bNAbs to HAs. The invention is also directed to modified HA proteins and genes with modified MCSs and to combinations of these modifications.

In one embodiment, modified recombinant HAs have the immunodominant antigenic sites of the globular head domain replaced by the extracellular domain of the M2 protein (M2e), or M2e is inserted into the immunodominant antigenic sites.

Guided by the three dimensional structures of HA proteins, a specific surface peptide or such surface peptides of immunodominant regions are replaced by a heterologous peptide or several heterologous peptides of other regions of the same HA or a heterologous peptide or several heterologous peptides from a HA of another subtype or strain of influenza virus. These heterologous peptides may be inserted into the immunodominant regions. In addition, the specific surface peptide or peptides of HA are replaced by heterologous peptides from other proteins that are not related to HA, or such peptides are inserted therein. These heterologous peptides are either natural proteins or artificially designed. They may not be recognized by currently known antibodies.

The immunodominant regions of HA are on the surface of the globular head domain of HA. These surface regions to be modified are surface-exposed helices, β-strands, or loops. These surface regions are preferably immunodominant antigenic sites and epitopes or parts of such antigenic sites and epitopes or next to such antigenic sites and epitopes.

In some embodiments, the immunodominant regions of HA globular head domain are replaced by peptides of the immunosubdominant epitopes of HA that are recognized by bNAbs to HAs. In other embodiments, the immunodominant regions of HA globular head domain are replaced by peptides of the immunosubdominant epitopes that are recognized by antibodies that neutralize a group of influenza viruses. These immunosubdominant epitopes are selected from the HA stem domain, or include the HA fusion peptide or the HA maturation cleavage site.

The recombinant modified HA proteins of this invention are expressed in cell culture and secreted into the cell culture media at levels similar to recombinant wild-type HA. These designs are applicable to any influenza HA of all strains of influenza A, B and C viruses, including but not limited to the influenza viruses that infect human, and the influenza viruses that infect other mammalian and avian species. In one embodiment, these modified HA proteins can be used as immunogens to make vaccines against influenza virus infection in human or animals.

These immunodominant regions may be changed by site-directed mutagenesis. The solvent-exposed residues of an antigenic site are identified by the three-dimensional structures of HA proteins. A solvent-exposed residue or several solvent-exposed residues of an antigenic site are changed by site-directed mutagenesis or replaced with a peptide containing the specific changes of these residues. The new site has the same secondary structure as the original site.

Illustrative HA with Antigenic Sites Replaced by Heterologous Epitopes

Based on the HA structure as illustrated in FIGS. 3A-3B, several positions in HA are selected to illustrate the feasibility of replacing immunodominant antigenic sites in the globular head domain by heterologous peptides from the stem domain of HA, for example.

Peptide KTSS of residues 119 to 122 (numbering as WT in FIG. 5) is a surface-exposed helical structure near the Sa site residues 124 to 125. The Sa site is on the side of the globular head domain of HA trimer and away from the receptor binding site. Modification at this site is unlikely to change the receptor binding site and hence the host receptor binding by the modified HA. The four-residue peptide KTSS is replaced by bNAb epitopes of the stem domain. HAGAKS of residues 137-142 at the Ca2 site that corresponds to the Site A of H3 HA, is a major immunodominant site. KKGNSYPKLSKS at residues 153 to 164 is a surface loop at the Sa site that corresponds to the Site B of H3 HA. The N-terminal part of this peptide KKGNS at residues 153 to 157 is replaced in some constructs. TSADQQSLYQNA at residues 184 to 195 of Sb site forms the helix at the top of the HA globular head domain.

The surface loop of the Sa site and helix of the Sb site are adjacent to each other in the globular head domain of HA and correspond to the Site B of H3. Together the Sa site and Sb site can accommodate a conformational epitope with loop and helix structures. However, since these sites are near the receptor binding site, replacement of these peptides may destroy the receptor binding site. EIAIRPKVRDQE at residues 213 to 224 of Ca2 site is a loop near the interface between two HA monomers. This loop has contacts with the β-strands of the adjacent HA monomer that corresponds to the Site D of H3 HA. Part of the loop is surface-exposed. Ca2 site is located within this peptide. In some constructs, this peptide is partially replaced.

In addition, the heterologous peptides can be placed in or near any other antigenic sites as illustrated in FIG. 5, and surface loops or helices as illustrated in FIGS. 1A-1B to FIGS. 3A-3B. Furthermore, a heterologous peptide can be inserted into any of these positions without any deletion of residues of the antigenic sites.

Figures 6A, 6B:
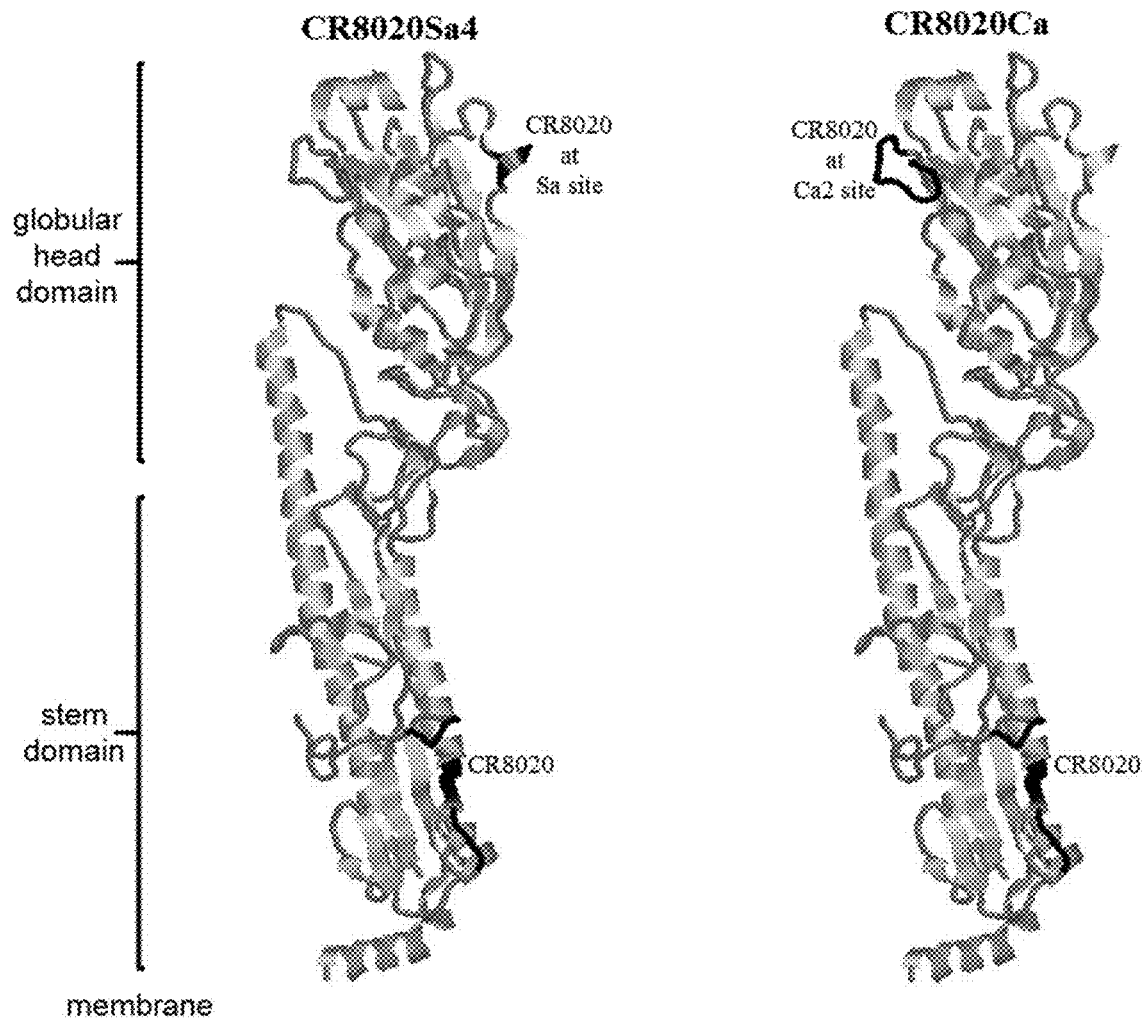
FIGS. 6A-6B illustrate models of HA monomer with the composite CR8020 epitope placed at the immunodominant antigenic sites of the globular head domain. The HA monomer is shown in a ribbon drawing as in FIGS. 1A-1B. The immunodominant antigenic sites that are replaced by composite CR8020 epitope are shown in dark shade. The original native CR8020 epitopes in the stem domain are also shown in dark shade.
Figure 7A:
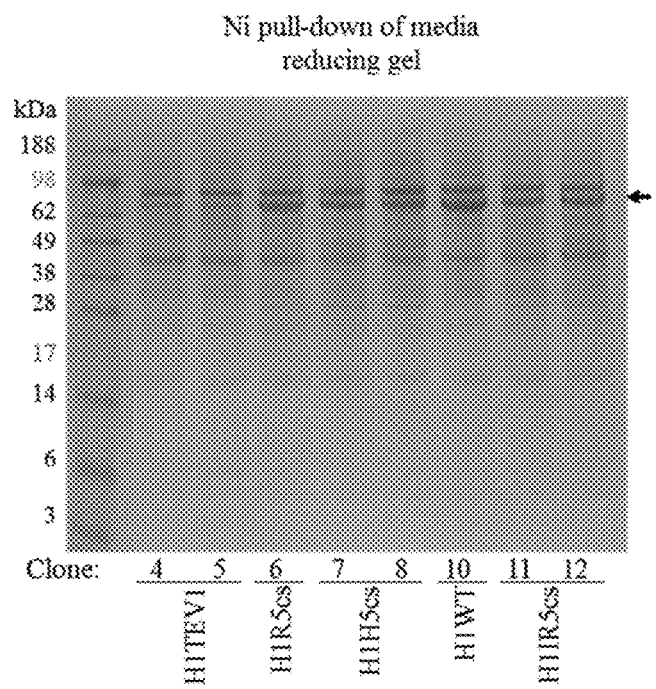
FIGS. 7A-7E show the expression data of HA constructs described in this invention. Cell culture medium of SF9 cells infected with recombinant baculovirus of the indicated construct was harvested and captured by Ni-NTA resin (Ni pull-down). The Ni-NTA resin was washed with 1×PBS to remove unbound proteins. Proteins bound to the Ni-NTA resin were analyzed by SDS-PAGE with Coomassie® staining (FIGS. 7A, B, C, and D) or anti-His Western blot (FIG. 7E). The arrow indicates the full-length HA0.
Figure 7B:
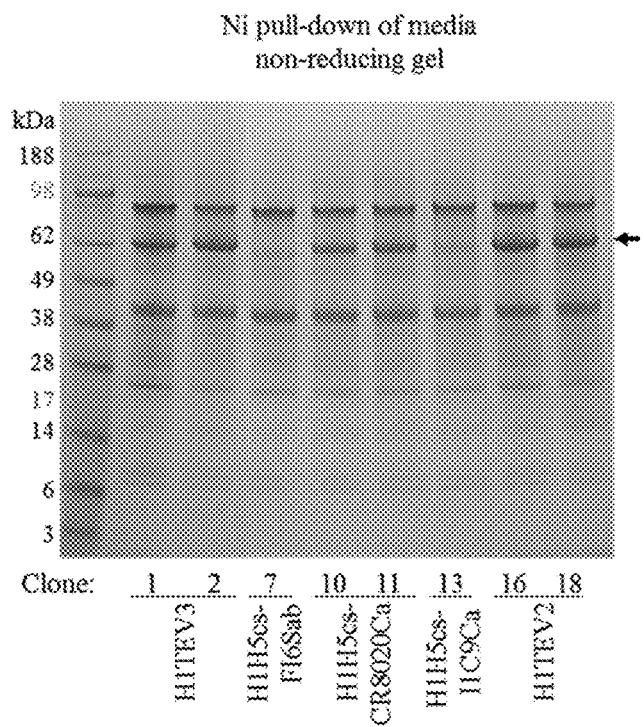
Figure 7C:
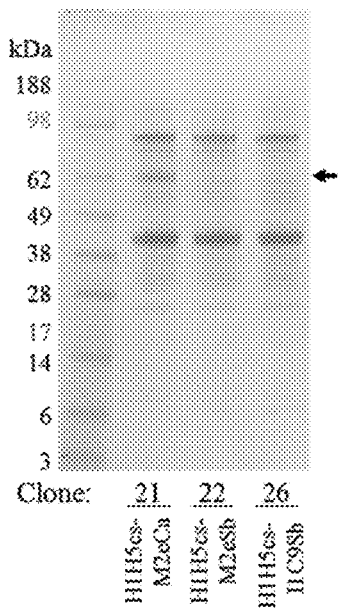
Figure 7D:
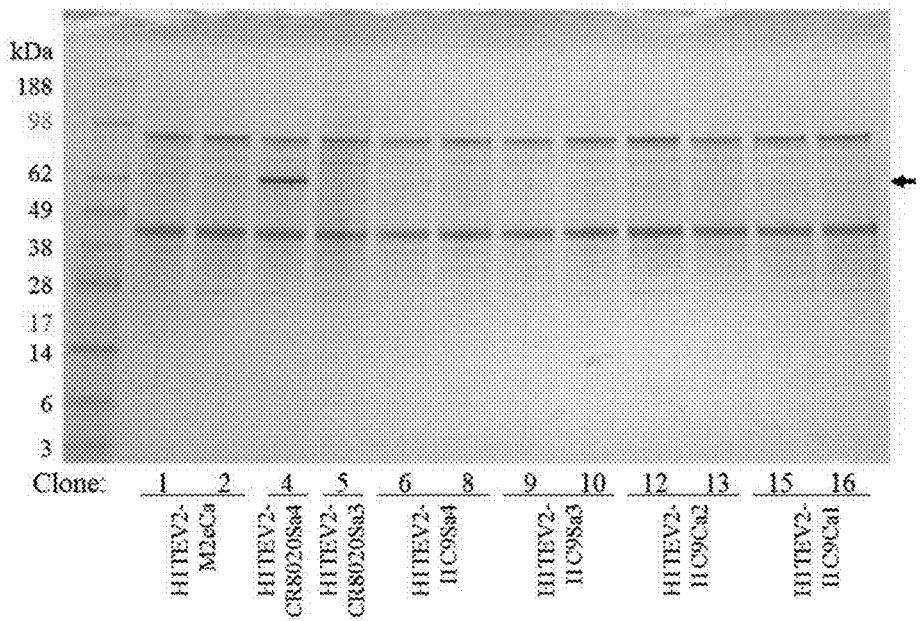
Figure 7E:
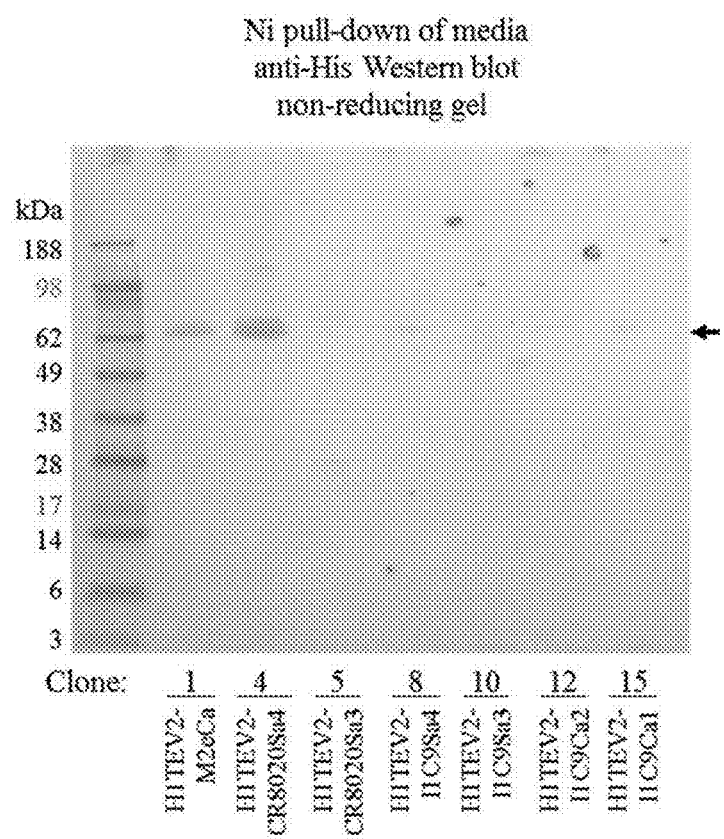

The bNAb CR8020 epitope is located in the stem domain. As shown in FIG. 5 and FIGS. 6A-6B, the CR8020 epitope has two main components consisting of the outermost β strand (HA2 residues 30 to 36, EGTGQAA of H3 HA, SEQ ID NO:26) of the 5-stranded β-sheet near the base of the stem domain and the C-terminal portion (HA2 residues 15 to 19, EGMID of H3 HA, SEQ ID NO:25) of the fusion peptide. These two components are separated by 10 amino acid residues in primary structure. A composite CR8020 epitope EGMIDYEGTGQAA (SEQ ID NO:27) is designed in which the two epitope components are linked by a tyrosine (Y). This composite CR8020 epitope is used as a heterologous peptide to replace the immunodominant sites.

Another bNAb 1C9 epitope is the fusion peptide in the N-terminus of HA2 present in the stem domain. A modified 1C9 epitope peptide of GIFGAIAGFIEG (SEQ ID NO:36) was designed as a peptide to be displayed in an immunodominant site. This modified 1C9 peptide, denoted as I1C9, has isoleucine (I) substitution of leucine (L) at the position 2 of the H5 fusion peptide recognized by bNAb 1C9. This I1C9 fusion peptide is present in swine H1 HA and HAs of some H6 and H9 viruses. This I1C9 peptide is placed at different immunodominant sites. Multiple constructs have been made with I1C9 to an antigenic site with shifted positions.

The bNAb FI6 epitope is a conformational epitope containing two peptides that form a continuous surface on the tertiary structure of HA precursor HA0 but separated in the primary structure (FIG. 5). One FI6 epitope peptide RKKRGLFGAIAGFIE is the maturation cleavage site and fusion peptide of HA0. Another FI6 peptide KESTQKAIDGVTNKVNS has a coiled-coil structure in HA2. A construct has been made wherein these two FI6 epitope peptides were placed in the globular head domain. The FI6 epitope peptide RKKRGLFGAIAGFIE is placed at the Sa site of residues 153 to 164 and the coiled-coil FI6 epitope peptide KESTQKAIDGVTNKVNS is placed at the Sb site of residues 184 to 195. In another construct, the FI6 epitope peptide RKKRGLFGAIAGFIE is placed at the Sa site without the second FI6 epitope peptide.

Many bNAb epitopes have been characterized. Any of them can be placed at or near the immunodominant antigenic sites or surface loops in the globular head domain as described above.

In other embodiments, the heterologous peptides are peptides of the extracellular domain of M2 proteins (M2e peptides). M2e peptides are conserved and less variable among influenza A viruses. M2e peptides are also conserved and less variable among influenza B viruses, although the M2e peptides from the influenza A viruses and influenza B viruses are different.

In some embodiments, the heterologous peptides are artificially designed peptides that make specific changes to the immunodominant antigenic sites by site-directed mutagenesis. In some embodiments, an artificial peptide combines desirable features of an immunodominant antigenic site and a heterologous peptide. In some embodiments, an artificial peptide has the residues for interaction with a bNAb and residues of the original immunodominant antigenic sites to maintain the three dimensional structure of the HA globular head domain. These artificial peptides are either rationally designed based on the HA three dimensional structures or by screening a library of randomly generated peptides.

Constructs have been made to place M2e peptide SLLTEVETPTRNGWECKCSDS at either the Ca2 site or the Sb site for expression using baculovirus expression system or mammalian expression system. The M2e peptide can be further optimized based on consensus of sequences from different influenza strains.

HA with Modified Maturation Cleavage Site

This invention includes embodiments wherein the protease susceptibility of the HA maturation cleavage site (MCS) is changed to make the resulting HA susceptible to a different class of proteases and resistant to those trypsin-like proteases that cleave the native HA maturation cleavage sites of all strains of influenza viruses. An altered MCS is designed to be recognized by a specific protease that is not present in known natural hosts of influenza viruses. This makes the resulting HA resistant to maturation in all natural hosts of influenza viruses. In the presence of this specific protease that recognizes this altered maturation cleavage site, these resulting HAs are cleaved to the mature form containing HA1 and HA2. Recombinant influenza viruses made from the resulting HAs in the presence of this specific protease form mature HA and become infectious to natural influenza hosts. However, the viral progeny replicated in infected natural hosts are not infectious due to the lack of the proper proteases in natural hosts.

H1 HA molecules often have a single basic residue in the MCS. This single basic residue is usually an arginine (R) residue, N-terminal to the scission bond. Adding multiple basic residues, such as arginine (R) or lysine (K), in the MCS of a H1 HA increases the infectivity of the recombinant influenza viruses containing the modified HA. Replacing a native H1 MCS with H5 MCS that contains polybasic residues increases the infectivity of the recombinant influenza viruses containing the modified HA (Kong, W-p., et al., *PNAS* (2006) 103:15987-15991). These polybasic residues are more susceptible to cleavage by many intracellular trypsin-like proteases. In some embodiments, H1 HA MCS is modified by replacing it with H5 HA MCS or polybasic residues. The H1 HA MCS is also modified by inserting polybasic residues between the last residue (arginine) of HA1 and the first residue (glycine) of HA2.

Further disclosed are genetically modified recombinant influenza HA genes and proteins with altered MCS sequences. The native MCS is replaced by sequences from the MCS from another HA. The said changes include replacing the native MCS of a HA with another MCS from a different HA that are known to make recombinant influenza viruses more infectious, presumably by making the resulting HA more susceptible to maturation cleavage by unidentified host proteases. In the preferred embodiment, the native MCS of H1 HA is replaced by an MCS of H5 HA, or replaced by polybasic residues of arginine (R) and lysine (K).

Several mammalian proteases such as Factor Xa and enterokinase have their respective cleavage recognition site located completely on the N-terminal side of the scission bond. Their cleavage recognition site can also be used to replace the native HA maturation cleavage site. As in the case of the native HA, the C-terminal side of the scission bond of these protease cleavage sites is a glycine (G). The thrombin cleavage site also has a glycine (G) on the C-terminal side of the scission bond. After thrombin cleavage, a new N-terminus of glycine (G) is generated. All these proteases are present in many natural influenza hosts. However these proteases are usually either not present or in trace amount in cell culture media or cell lines used for recombinant HA production.

TEV protease of tobacco etch virus (TEV) recognizes a cleavage site of ENLYFQG and cleaves between glutamate (Q) and glycine (G). The free N-terminus generated by TEV protease cleavage is glycine (G), the same as N-terminal residue of HA2 after HA maturation. Unlike the MCS of native HA, there are no basic residues in TEV cleavage site. In some embodiments, the entire HA MCS is replaced by the TEV cleavage site, or a few residues of the MCS are replaced by the TEV cleavage site, or only the arginine (R) N-terminal to the scission bond, for example, is replaced by the TEV cleavage site. The HA constructs with the MCSs replaced by TEV cleavage site are expressed using baculovirus expression system or mammalian expression system, and constructs that express to the same level as wild-type HA have been identified.

In the presence of TEV protease that cleaves the modified MCS, the said modified HA undergoes maturation and is converted to HA1 and HA2 with the native N-terminus of fusion peptide. The mature modified recombinant HA has the capability to bind the corresponding host cell receptors and undergo membrane fusion. In the absence of the TEV protease, the newly synthesized said modified HA remains as the uncleaved HA0 precursor. The lack of free N-terminus of fusion peptide prevents the said HA from membrane fusion. The progeny HA protein produced in the infected host cells remains as HA0 and is not processed to the mature functional form due to the lack of TEV protease in the host. The newly made viruses with HA0 do not have the ability of membrane fusion and therefore are non-infectious.

Combinations of Antigenic Sites and Maturation Cleavage Sites

The changes of the antigenic sites in the globular domain of HA and the changes of MCS in the stem domain of HA can be in any kind of combinations. A particular heterologous peptide can be introduced to an antigenic site in the globular head domain of HA proteins with different altered maturation cleavage sites. In addition, two or more heterologous peptides can be introduced to a single HA protein at different antigenic sites. In one embodiment, a genetically modified recombinant influenza HA has M2e peptide replacing an antigenic site in the globular head domain of HA and TEV protease site as the MCS. In another embodiment, a genetically modified recombinant influenza H1 HA has M2e peptide replacing an antigenic site in the globular head domain of HA and H5 MCS in place of H1 native MCS.

Methods of Production

For production of modified HA, the protein is secreted by the cells into the cell culture medium as soluble form and is not an integral membrane protein or is not attached to cell membranes or cell surface. In some embodiments, the native HA signal sequence is used for secretion in insect cells and in mammalian cells. In other embodiments, the native HA signal sequence is replaced by an insect cell signal sequence for secretion in insect cells or a mammalian signal sequence for secretion in mammalian cells. In place of the HA transmembrane domain and intracellular domain, a protease cleavage site is placed at the C-terminal end of the HA extracellular domain, followed by a "foldon" sequence derived from the bacteriophage T4 fibritin to stabilize the HA trimer, and a C-terminal His-tag to facilitate purification. The recombinant HA protein is made either as a full-length uncleaved precursor HA0 with the signal sequence removed or the mature form containing HA1 and HA2 subunits with the wild-type fusion peptide at the N-terminus of HA2. In the preferred embodiment, the final purified genetically modified HA forms a trimer as the wild-type HA.

The genes of the designed recombinant influenza HA are made by de novo gene synthesis. The gene synthesis technologies have been well established and extensively reviewed (Kosuri, S., and Church, G. M., Nat Methods (2014) 11:499-507). Genes of over 10 kb in length have been routinely made by commercial providers. Gene synthesis offers the ability to modify specific HA sequences and the opportunity of codon-optimization according to the expression hosts or specific genetic engineering needs. Restriction sites are designed at specific locations of the synthesized HA genes to facilitate exchange of HA fragments between different constructs. The synthesized HA genes with the signal sequences and the protease sites, foldon sequence, and C-terminal His-tag are incorporated into baculovirus genome with well-established protocols so that the expression of the modified HA proteins is directed by baculovirus polyhedrin promoter. In other embodiments, the same set of HA genes are cloned into mammalian expression vectors for expression in mammalian cells.

In some embodiments, HA constructs are codon-optimized for expression in insect cells using baculovirus vectors. In other embodiments, HA constructs are codon-optimized for expression in mammalian cells, including but not limited to CHO cells (Chinese hamster ovary cells) and HEK 293 cells (human embryonic kidney 293 cells). Codon optimization to any organism is routinely done using commercial software such as Lasergene software package from DNASTAR, Inc. (3801 Regent Street, Madison, Wis. 53705 USA), online web server such as OPTIMIZER (located on the World Wide Web at genomes.urv.es/OPTIMIZER/), or by gene synthesis service providers using their proprietary algorithms. Codon optimization takes into considerations of G/C content, elimination of cryptic splice sites and RNA destabilizing sequence elements, and avoidance of stable RNA secondary structures. Codons are also manually adjusted based on the Codon Usage Database (located on the World Wide Web at kazusa.or.jp/codon/). Due to codon degeneracy, gene sequences can be changed without changing the encoded amino acid sequences. Restriction sites are introduced at specific locations by changing codons without changing amino acid sequences. Using any of these methods, gene sequences, with or without codon optimization to a specific organism, are routinely generated by back translation of protein sequences using a computer algorithm or manually.

Other embodiments include a method to make recombinant non-infectious influenza viruses from the genetically modified HA genes with the MCS changed to the TEV protease recognition site using established cell culture methods. Reverse-genetics systems that allow production of influenza viruses from RNA segments or plasmids with cloned cDNAs have been developed, with or without using helper virus (Luytjes, W., et al., Cell (1989) 59:1107-1113; Neumann, G., et al., PNAS (1999) 96:9345-9350; Fodor, E., et al., J. Virol (1999) 73:9679-9682; de Wit, E., et al., J. Gen Virol (2007) 88:1281-1287). Infectious influenza viruses are made by transient transfection of mammalian cells with influenza RNA segments or plasmids with the cDNA of influenza RNAs. These viruses that are isolated from the cell culture media are used to infect embryonated chicken eggs to produce live infectious influenza viruses for making vaccines. Some of the influenza RNA segments are replaced by a foreign gene. Recombinant influenza A viruses have been made using an influenza C virus HEF protein replacing HA protein (Gao, Q., et al., J. Virol (2008) 82:6419-6426). In these embodiments, the cDNA or RNA of the modified HA is co-transfected to mammalian cells with cDNAs of the other 7 influenza RNAs or the other 7 RNA segments made by standard molecular techniques and gene synthesis. Using an established method or similar methods, multiple identical or different HA proteins can be packaged in a single virion (Uraki, R., et al., J. Virol (2013) 87:7874-7881).

Methods to make recombinant infectious influenza viruses from a genetically modified HA gene use established cell culture methods as described above. In these embodiments, a genetically modified HA gene with H5 HA MCS or polybasic sequence at the MCS is co-transfected to mammalian cells with cDNAs of the other 7 influenza RNAs or the other 7 RNA segments made by standard reverse genetics system as described above. These modified maturation cleavage sites increase the efficiency of HA maturation in influenza natural hosts or in cell culture (Kong, W-p., et al., PNAS (2006) 103:15987-15991). The mature functional HA protein has the ability to bind to host cells and fuse with host cell membrane.

Other embodiments include a method to make recombinant influenza virus-like particles (VLP) from the genetically modified HA genes using established cell culture methods in mammalian cells, in insect cells, and in plant cells (Chen, B. J., et al., J. Virol (2007) 81:7111-7123; Smith, G. E., et al., Vaccine (2013) 31:4305-4313; D'Aoust, M. A., et al., Plant Biotech (2010) 8:607-619).

Other embodiments include a method to make DNA vaccines from the genetically modified HA genes using established methods (Jiang, Y., et al., Antiviral Res (2007) 75:234-241; Alexander, J., et al., Vaccine (2010) 28:664-672; Rao, S. S., et al., PLoS ONE (2010) 5:e9812).

The expression results disclosed herein show that the MCS of H1 HA can be modified without affecting the expression of the resulting HA. Constructs with H5 HAMCS or polybasic MCS have been demonstrated to express to the same level as the wild type H1 HA. Furthermore, the MCS of HA is replaced by TEV protease cleavage site which does not have any basic residues. By changing the position of the TEV protease cleavage site, constructs with TEV cleavage site as the MCS have been made that expressed to the same level as the wild type H1 HA.

The expression results further show that many of the antigenic sites in the globular head domain of HA1 can be replaced by heterologous peptides from the stem domain of the same HA or different HAs. Some of the constructs are expressed to the same level as the wild type HA, whereas other constructs are expressed much less. The nature of the heterologous peptides and the locations of the heterologous peptides in the globular head domain have significant impact on the expression level of each resulting HA construct. More constructs can be made and tested in the same manner for their expression to identify the most optimal expression constructs.

In addition, recombinant HAs are made with replacements of certain immunodominant antigenic sites of HA globular head domain by M2e epitope from influenza M2 protein. Conceivably, any epitope of other influenza proteins can serve as a replacing peptide to replace an immunodominant antigenic site in the HA globular head domain. Furthermore, a heterologous replacing peptide can be derived from another protein not related to influenza viruses. A specific antigenic site in the HA globular head domain can be chosen for a replacing peptide to maintain the native structural feature of the replacing peptide as much as possible to present the replacing peptide to host immune system.

Baculovirus Expression System

Since its introduction about 30 years ago (U.S. Pat. No. 4,745,051; Summers, M. D., and Smith, G. E., (1987) *A Manual of Methods for Baculovirus Vectors and Insect Cell Culture Procedures. Texas Agricultural Experiment Station Bulletin No.* 1555.), baculovirus expression vector system (BEVS) has been used to express many different types of human and viral proteins including intracellular proteins, membrane proteins, and secreted proteins. BEVS has been used to produce virus-like particles (VLPs). BEVS is a eukaryotic expression system that uses insect cells as host, which provides post-translational modifications of proteins similar to mammalian cells (Jarvis, D. L., "Baculovirus Expression Vectors" in *The Baculoviruses*, ed. Miller, L. K. (1997) pp. 389-420 Plenum Press, New York). BEVS based on *Autographa californica* nuclear polyhedrosis virus (AcNPV) has been well established. Many commercial kits are available for producing recombinant baculoviruses. BEVS has been successfully used to produce recombinant vaccines marketed in US. Two FDA approved vaccines, Cervarix™, a recombinant human Papillomavirus bivalent (Types 16 and 18) vaccine in the form of non-infectious virus-like particles (VLPs) against cervical cancer (Patent Application WO2010/012780 A1) and Flublok® (U.S. Pat. Nos. 5,762,939 A and 5,858,368 A), a trivalent influenza vaccine made of membrane bound hemagglutinin precursors (HA0) against influenza, are produced using BEVS.

To express a target protein using BEVS, the gene-of-interest that encodes the target protein is first subcloned into a transfer vector which is an *E. coli* plasmid containing baculovirus sequences flanking the baculovirus polyhedrin gene. Polyhedrin is an abundant viral protein in wild type baculoviruses that is not needed for baculovirus propagation in cell culture. The transfer vector is propagated in *E. coli* and isolated using standard molecular biology techniques (Sambrook, J., et al., (1989) *Molecular Cloning: A Laboratory Manual*, Cold Spring Harbor Laboratory Press, Cold Spring Harbor). The transfer vector with gene-of-interest is recombined with baculovirus genomic DNA to produce a recombinant baculovirus genome either in *E. coli* or in insect cells. The recombinant baculovirus genome directs the production of the recombinant baculoviruses and the expression of the target protein. The original method relies on homologous recombination between the same sequences flanking the polyhedrin gene in transfer vector and in viral genomic DNA in insect cells. The isolated transfer vector DNA is co-transfected with baculovirus genomic DNA into insect cells. Recombinant baculoviruses are selected for the lack of polyhedrin. Current commercial kits, such as BacPAK™ Baculovirus Expression System from Clontech and Bac-Magic™ System from Millipore, use linearized baculovirus genomic DNA that does not produce viable virus without recombination. These kits allow production of recombinant baculoviruses with high efficiency and little contamination of non-recombinant viruses. Recombination to viral genome can also be made in vitro using Gateway recombination reaction (BaculoDirect™ Baculovirus Expression System, Life Technologies). Another method to make recombinant viruses is through site-specific transposition in *E. coli* (Bac-to-Bac System, Life Technologies). The pFastBac-based transfer vector contains transposons that make bacmids (a large plasmid containing the genome of a baculovirus) in *E. coli* (U.S. Pat. No. 5,348,886). The recombination of the gene-of-interest to a bacmid is easily confirmed by polymerase chain reaction (PCR) before transfection of bacmids to insect cells.

Recombinant baculoviruses are propagated in insect cell culture. A small amount of viruses is used to infect insect cells. After a few days, the conditioned media containing amplified viruses are harvested as viral stocks. This amplification process is often repeated several times to generate a large volume of viral stocks. The viral stocks are routinely stored in the dark with refrigeration for months and even years. Supplement of 5-10% fetal bovine serum (FBS) to the viral stocks has been used to preserve the viral stocks and is believed to prolong their shelf lives. The viral stocks are sometimes frozen for long term storage at $-70°$ C. Viruses have also been amplified and stored as baculovirus-infected insect cells (BIIC) (Wasilko, D. J., et al., *Prot Exp Purif* (2009) 65:122-132). The infected insect cells are harvested before their lysis as BIIC stocks and are frozen following standard cell freezing procedure. BIIC stocks are stored in liquid nitrogen or at ultra-low temperature between $-65°$ C. to $-85°$ C. for a long period of time and are used as viral stocks to infect insect cells for protein expression. The frozen BIIC stocks offer longer storage time than viral stocks in liquid form.

The commonly used insect cell lines for BEVS are SF9 and SF21 cells derived from fall armyworm (*Spodoptera frugiperda*) and Hi5 or *T. ni* cells derived from cabbage looper (*Trichoplusia ni*). Other insect cells derived from species of silkworm (*Bombyx mori*), honeycomb moth (*Galleria mellonella*), and gypsy moth (*Lymantria dispar*) have also been used. SF9, SF21, and Hi5 (or *T. ni*) cells have been adapted to suspension culture in serum-free media. These cell lines and media are available from many commercial sources. The cell culture of these cell lines is routinely maintained in shaker flasks in small volumes of up to 1 or 2 liters in shaker incubators in ambient atmosphere without supplement of gas at temperature in the range of 22-28° C. The cell culture is scaled up in stirred tank bioreactors or single-use bioreactors. The conditions for large scale insect cell culture in bioreactors have been well established (WAVE Bioreactor Systems—Cell culture procedures. GE Healthcare). Supplement of oxygen is also routinely used in large scale insect cell culture to increase cell density.

A series of conditions for expression of a particular target protein are tested to optimize the expression of the target protein using different cell lines by varying the virus-to-cell ratio and the harvest time post infection. SF9, SF21, and Hi5 (or *T. ni*) cells are the most common cell lines used for BEVS protein expression. A target protein may express better in one of the cell lines than the others. Some reports show Hi5 (or *T. ni*) cells give more expression of certain secreted proteins. The virus-to-cell ratio, commonly known as multiplicity of infection (MOI), is tested to determine the best infection condition for target protein expression. Culture samples are taken at various time points post infection. Cells and the conditioned media are separated by centrifugation or filtration. Protein expression levels are determined by standard methods. The culture is monitored for cell density, cell viability, and cell size, which provide the information on cell growth and culture conditions. Glucose level, dissolved oxygen, and pH of the culture are sometimes monitored for consumption of nutrients in the media. The condition that leads to the best target protein expression is selected for large scale production of the protein.

Although determination of the titers of viral stocks and MOI is widely used to determine the infection conditions for viral amplification and protein expression using BEVS, the aforementioned TIPS method offers a faster way to determine the best infection conditions for viral amplification and protein expression. Insect cells enlarge in size after infection with recombinant baculoviruses. Cell division also stops after infection. Recombinant baculoviruses cause cell lysis around 48 hours post infection. The cell division is monitored by counting cells as cell density of the culture. Cell lysis is monitored as cell viability by counting live and dead cells in the culture. Viable cell size is measured as the cell diameter. Cell density, cell viability, and viable cell size are routinely measured by many models of cell counting instruments. Cell density and cell viability can also be measured manually using a hemocytometer. Collectively, cell density, cell viability, and viable cell size provide information on infection kinetics. TIPS method uses infection kinetics to determine the optimal condition for expression of a particular target protein using a particular viral stock. It eliminates the time consuming measurements of viral titer for MOI calculation. Consistent viral amplification and protein expression is routinely achieved using TIPS method.

In addition to insect cells, live insects infected with recombinant baculoviruses have been used to express many secreted proteins and membrane proteins. Mature HA has been expressed in larvae of tobacco budworm (*Heliothis virescens*) (Kuroda, K., et al., *J. Virol* (1989) 63:1677-1685).

Expression system based on other types of baculoviruses such as *Bombyx mori* nuclear polyhedrosis virus (BmNPV) has also been developed. BmNPV may have a better biological safety profile over the AcNPV in that it has a narrower host range and will not grow as insect pests in the field. BmNPV-based baculovirus expression system has been used to express functional proteins in cell culture and silkworm (*Bombyx mori*) larvae (Maeda, S., et al., *Nature* (1985) 315:592-594).

BEVS has been routinely used to produce protein complexes and VLPs. Two or more genes are cloned into a single vector for expression of multiple proteins. Two or more viral stocks each directing the expression of a single protein are used for co-infection of insect cells to produce protein complexes or VLPs. Influenza VLPs have been made using baculovirus expression system (Bright, R. A., et al., *PLoS ONE* (2008) 3:e1501).

HA Transfer Vectors for Baculovirus Expression

The genes to be expressed using BEVS are commonly under the control of polyhedrin promoter, a strong late promoter of baculovirus that leads to protein expression before the baculovirus-induced insect cell death. Other early or late promoters are also used for protein expression. To secrete a recombinant target protein into the cell culture media by insect cells, a DNA segment that encodes a signal peptide is engineered at the 5' end in-frame to the gene-of-interest. Two commonly used signal peptides for insect cells are the honeybee melittin signal sequence or the AcNPV envelope surface glycoprotein GP67 signal sequence. Signal Sequence Database (located on the World Wide Web at signalpeptide.de/index.php) lists many other possible signal peptides for consideration. After secretion, the signal peptide is removed by a cellular protease that processes the signal peptide. Although influenza viruses are not insect viruses, HA signal peptides have been used as secretion signal peptides for secretion or membrane insertion of recombinant proteins in BEVS. A HA signal peptide of MKTIIAL-SYIFCLVFA is commonly used for expression of recombinant transmembrane G protein coupled receptors (GPCRs) in insect cells (Rosenbaum, D. M., et al., *Science* (2007) 318:1266-1273; Zou, Y., et al., *PLoS One* (2012) 7: e46039). HA has been expressed in insect cells using its native signal peptide. In that particular case, the total expression was lower than that using an insect cell signal peptide but the expressed HA was in the mature form containing HA1 and HA2 (U.S. Pat. No. 5,858,368 A). The HA signal peptides are not conserved among HAs. For example, the aforementioned HA signal peptide is different from the H1 HA signal peptide of SEQ ID NO:7. Empirical selection of HA signal peptides may improve HA expression in insect cells.

Commercial vectors are available for making recombinant baculoviruses through homologous recombination, using the Bac-to-Bac system or the Gateway system (Life Technologies). Features of these transfer vectors such as promoters and signal sequences can be customized by standard molecular biology techniques. The whole transfer vector can now be fully synthesized by gene synthesis. Gene synthesis allows designs of transfer vectors with specific sequences and features.

Methods to express influenza HA using BEVS have been well established at laboratory scale (Stevens, J., et al., *Science* (2004) 303:1866-1870). For example, a transfer vector contains the HA from the 1918 influenza virus under the control of polyhedrin promoter. The 1918 influenza virus HA expression construct has a GP67 signal peptide instead of the HA signal peptide at the N-terminus for secretion. In place of the transmembrane domain, a thrombin cleavage site is introduced at the C-terminal end of the HA extracellular domain, followed by a "foldon" sequence derived from the bacteriophage T4 fibritin to stabilize the HA trimer, and a C-terminal His-tag to facilitate purification. The foldon sequence and His-tag can be removed by thrombin cleavage. Similar designs of HA expression transfer vectors have been used to express different HAs from many strains of influenza (Stevens, J., et al., *Science* (2006) 312:404-410; Xu, R., et al., *Science* (2010) 328:357-360; Whittle, J. R. R., et al., *PNAS* (2011) 108:14216-14221).

In addition to foldon, other trimerization domains can be used to stabilize the trimer of recombinant HAs. For example, a thermostable HIV-1 glycoprotein 41 (gp41) trimerization domain or the initial 16 of the 31 residues of the GCN4 leucine zipper sequence was used to aid the trimerization of truncated HA constructs (Impagliazzo, A., et al., *Science* (2015) 349:1301-1306; Yassing, H. M., et al., *Nat Med* (2015) 21:1065-1070).

Recombinant HA precursors (HA0) from both influenza A and influenza B viruses, with the transmembrane domain and intracellular domain, have been made using BEVS at commercial scale as disclosed in U.S. Pat. Nos. 5,762,939 A, 5,858,368 A, and 6,245,532 B1. These recombinant HA proteins are the ingredients in Flublok® which has obtained FDA approval as an influenza vaccine. The HA0 in Flublok® is made using a baculovirus chitinase signal peptide (referred to as 61K signal peptide) to replace the HA signal peptide. The recombinant HA is associated with the peripheral membrane of insect cells. It is extracted from membrane using detergent and further purified.

Mammalian Expression

Chinese hamster ovary (CHO) cells and human embryonic kidney 293 (HEK293) cells are commonly used mammalian cell hosts for transient transfection gene expression of recombinant proteins. Both CHO cells and HEK293 cells have suspension cell lines and adherent cell lines. These cells are routinely cultured in media with or without FBS. When cells are cultured without FBS, chemically defined media are often used. All suspension and adherent cell lines can be used to express HA or other secreted proteins.

Transient transfection is a well-established method to introduce DNA into cells for protein expression. Many commercial transfection reagents are available. Similar to the expression optimization process for baculovirus expression, media samples are taken periodically post transfection for analysis of protein expression using standard methods. HA proteins are easily detected by affinity capture through the His-tag in the HA constructs or Western blot using many commercially available anti-HA antibodies. Protein expression usually starts around 48 hours post transfection and may increase over several days post transfection. Supplements are sometimes added post transfection to increase the target protein expression. Other mammalian cell lines such as COS-1, a fibroblast-like cell line derived from African green monkey kidney tissue, have also been used for HA expression. Influenza VLPs have been produced by co-transfection of multiple plasmids containing cDNAs of all 10 influenza virus-encoded proteins (Mena, I., et al., *J. Virol* (1996) 70: 5016-5024; Chen, B. J., et al., *J. Virol* (2007) 81:7111-7123).

Another method to deliver genes to mammalian cells uses recombinant baculovirus known as BacMam for baculovirus gene transfer into mammalian cells (Boyce, F. M., and Bucher, N. L., *PNAS* (1996) 93:2348-2352; Dukkipatia. A., et al., *Protein Expr Purif* (2008) 62:160-170). The baculovirus has been modified by incorporating a mammalian expression cassette into the baculovirus expression vector for transgene expression in mammalian cells. Recombinant BacMam baculoviruses are generated by the standard methods for baculovirus production. Amplified recombinant BacMam baculovirus viral stocks are added to CHO or HEK293 culture for delivery of the mammalian expression cassette to the CHO or HEK293 cells for protein expression. The BacMam platform enables easy transduction of large quantities of mammalian cells.

Gene expression vectors transfected to mammalian cells can be integrated into the cell chromosomes to establish stable cell lines for expression of the target proteins. Stable CHO cell lines are the most common hosts for the production of therapeutic biologics such as monoclonal antibodies. The technology is well suited for large scale production of therapeutic proteins and vaccines. To establish a stable cell line, the cells transfected with an expression vector are subjected to selection based on the selection marker on the expression vector. Multiple copies of the target genes are often integrated into the genome of a stable cell line.

HA Vectors for Mammalian Expression

The HA expression constructs for mammalian expression have the same designs and amino acid sequences as those for baculovirus expression. The codons are optimized for CHO cell expression or HEK293 cell expression. The baculovirus codons also work well for mammalian cells and vice versa. HA signal peptide has been used as signal peptide for secretion or membrane insertion of recombinant proteins in mammalian expression systems. Other commonly used mammalian signal peptides include human IL2 signal peptide, tissue plasminogen activator (tPA) signal peptide, and many other signal peptides found in Signal Sequence Database (located on the World Wide Web at signalpeptide.de/index.php). Many mammalian expression vectors are commercially available. Each vector usually has an enhancer-promoter for high-level expression, a polyadenylation signal and transcription termination sequence for mRNA stability, SV40 origin for episomal replication, antibiotics resistance gene and pUC origin for selection and maintenance in *E. coli*. Commonly used promoters for mammalian expression include CMV (Cytomegalovirus) promoter, hEF1-HTLV promoter, a composite promoter comprising the Elongation Factor-1α (EF-1α) core promoter and the R segment and part of the U5 sequence (R-U5') of the Human T-Cell Leukemia Virus (HTLV) Type 1 Long Terminal Repeat, or other promoters found in MPromDb (Mammalian Promoter Database located on the World Wide Web at mpromdb.wistar.upenn.edu/) or The Eukaryotic Promoter Database (EPD located on the World Wide Web at epd.vital-it.ch/). A transfer vector often has another selection marker for generating stable cell lines.

The following examples are offered to illustrate but not to limit the invention.

EXAMPLE 1

Figure 4A:
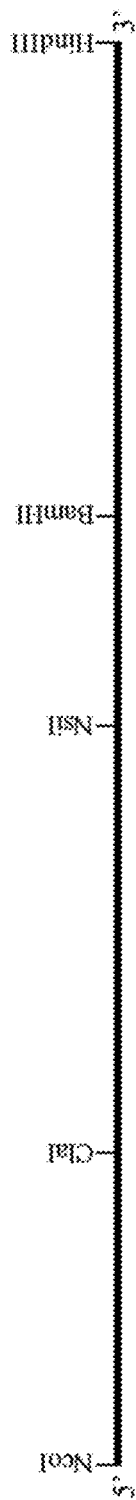
FIGS. 4A-4B illustrate the schematic design of the H1 HA constructs.
Figure 4B:

Construction of Transfer Vectors of H1 HA for Recombinant Baculovirus Production In this example, a parental plasmid that can be modified to prepare the modified HA protein of the invention is described. The basic outlines of this plasmid are shown in FIGS. 4A-4B wherein an insert into a standard plasmid for expression in baculovirus is bracketed by restriction sites for such insert and restriction sites are present which permit replacement of the MCS of the HA protein and replacement of the immunodominant regions in the globular head domain of HA. The encoded protein is fused to an affinity tag of 10 histidines (10×His-tag) for purification which can be removed by virtue of an inserted protease cleavage site after purification. This vector is designated H1WT.

The HA sequence (SEQ ID NO:1) of A/California/07/2009, a swine origin influenza A virus H1N1 strain that was recommended by WHO for 2009 influenza vaccine production (as noted on the World Wide Web at who.int/csr/resources/publications/swineflu/vaccine_recommendations/en/), was used as the parental sequence to incorporate heterologous peptides. This HA sequence has the accession number of UniProt:C3W5X2. All constructs have the same design as illustrated schematically in FIG. 4. The N-terminal HA signal peptide (SEQ ID NO:7) was replaced by GP67 signal peptide MVSAIVLYVLLAAAAHSAFA (SEQ ID NO:2). The C-terminal transmembrane (TM) domain with a sequence of ILAIYSTVASSLVLVVSLGAISFWMCS and intracellular domain with a sequence of NGSLQCRICI of HA was replaced by a TEV cleavage site (SEQ ID NO:4) followed by foldon (SEQ ID NO:5) and 10×His-tag (SEQ ID NO:6), namely GAENLYFQGGSGYIPEAPRDGQAY-VRKDGEWVLLSTFLGHHHHHHHHHH (SEQ ID NO:3), based on the HA construct first described by Stevens, J., et al., *Science* (2006) 312:404-410. The foldon stabilizes the recombinant HA while the 10×His-tag facilitates purification of HA from cell culture media. The foldon and 10×His-tag can be removed by TEV protease that recognizes the TEV cleavage site located between the HA sequence and the foldon sequence. The gene was codon optimized for baculovirus expression and synthesized by standard method (GENEWIZ, South Plainfield, N.J. 07080, USA).

As shown schematically in FIGS. 4A-4B, spaced unique restriction sites, ClaI site, NsiI site, and BamHI site, were introduced into the HA sequence to facilitate sequence change and swapping. The resulting construct GP67-H1WT-TEV-foldon-10His, denoted as "H1WT" (SEQ ID NO:9), was subcloned into a pFastBac plasmid between NcoI site and HindIII site. The sequence between ClaI and NsiI sites encodes most of the immunodominant antigenic sites of the globular head domain. The sequence between NsiI and BamHI site encodes the MCS. The expression of H1WT construct is under the control of baculovirus polyhedrin promoter. The resulting plasmid is the transfer vector for the expression of the recombinant wild type HA of A/California/07/2009. The H1WT construct is the parental construct from which genetically modified HA constructs are made.

To make genetically modified HA with heterologous peptides, the wild type fragments of H1WT were replaced using the aforementioned restriction sites with synthesized DNA fragments that encode specific changes to the HA. To modify the MCS, the NsiI-BamHI fragment of H1WT was replaced by DNA fragments that encode altered maturation cleavage sites. To change the antigenic sites in HA1 globular head domain, the ClaI-NsiI fragment of H1WT was replaced by DNA fragments that encode altered antigenic sites with heterologous peptides. Constructs with different combinations of the maturation cleavage sites and the antigenic sites were made by simple exchanges of the restriction fragments of different plasmids. The resulting constructs were confirmed by DNA sequencing.

EXAMPLE 2

Design and Construction of H1 HA Constructs with Modified Maturation Cleavage Sites In this example, the segment of H1WT between the NsiI and BamH1 restriction sites that bracket the MCS is replaced by alternative sequences that modify this MCS. In several instances, the TEV cleavage site is included in the modified MCS.

Modified maturation cleavage sites were introduced into the transfer vectors of H1 HA described in Example 1. Constructs with modified maturation cleavage sites are listed in Table 1.

The positions of these modifications are illustrated in FIG. 5.

Construct H1H5cs (SEQ ID NO:11) has the MCS of wild type H1 HA (SEQ ID NO:9) replaced by H5 MCS (SEQ ID NO:12). Construct H1R5cs (SEQ ID NO:14) has the MCS of wild type H1 replaced by five arginines. Construct H1IR5cs (SEQ ID NO:16) has four arginines inserted between the HA1 and HA2 sequences while keeping all the native HA1 residues. The NsiI-BamHI fragment with the changes were synthesized and subcloned between NsiI and BamHI sites of H1WT to replace the wild type fragment.

To test whether the H1 HA MCS can be modified to the TEV cleavage site that does not contain any basic residue, several constructs were made by changing the number of residues at the H1 HA MCS. Construct H1TEV1 (SEQ ID NO:18) has 7 residues, PSIQSRG, at the H1 HA MCS replaced by the 7-residue TEV cleavage site of ENLYFQG (SEQ ID NO:4). Construct H1TEV2 (SEQ ID NO:20) has 8 residues, IPSIQSRG, of the H1 HA MCS replaced by SPENLYFQG containing the TEV cleavage site. Construct H1TEV3 (SEQ ID NO:22) has the last 3 residues (QSR) of H1 HA MCS (SEQ ID NO:8) replaced by the TEV cleavage site.

EXAMPLE 3

Design and Construction of H1 HA Constructs with Heterologous Epitopes in the Globular Head Domain In this example, the basic plasmid and the plasmid with modified MCS were modified between the ClaI and NsiI sites by alternative nucleotide sequences where the various immunodominant sites were replaced with heterologous epitopes.

Heterologous epitopes were introduced to the constructs described in Example 1 and Example 2. The heterologous epitopes were inserted around immunodominant antigenic sites of HA globular head domain or replaced the immunodominant antigenic sites of HA globular head domain. Constructs with modified antigenic site(s) are listed in Table 2.

TABLE 1

List of H1 HA Constructs with Altered Maturation Cleavage Site

| List No. | Construct Name | Construct Description | SEQ ID Number |
| --- | --- | --- | --- |
|  | H1MCS[a] | GP67ss-H1MCS-TEV-foldon-10His[b] |  |
| 1 | H1WT[c] | GP67ss-H1WT-TEV-foldon-10His | SEQ ID NO: 9 |
| 2 | H1H5cs | GP67ss-H1H5cs-TEV-foldon-10His | SEQ ID NO: 11 |
| 3 | H1R5cs | GP67ss-H1R5cs-TEV-foldon-10His | SEQ ID NO: 14 |
| 4 | H1IR5cs | GP67ss-H1IR5cs-TEV-foldon-10His | SEQ ID NO: 16 |
| 5 | H1TEV1 | GP67ss-H1TEV1-TEV-foldon-10His | SEQ ID NO: 18 |
| 6 | H1TEV2 | GP67ss-H1TEV2-TEV-foldon-10His | SEQ ID NO: 20 |
| 7 | H1TEV3 | GP67ss-H1TEV3-TEV-foldon-10His | SEQ ID NO: 22 |

[a]Constructs name is based on the maturation cleavage site. H1 denotes H1 HA. MCS denotes a maturation cleavage site.
[b]Constructs are described by their sequence features. GP67ss denotes GP67 signal sequence. TEV-foldon-10His denotes the sequence of TEV cleavage site, foldon sequence, and 10xHis-tag at the C-terminus of the constructs. Schematic drawings of constructs are shown in FIG. 4.
[c]H1WT is the wild-type H1 HA construct with native MCS.

TABLE 2

List of H1 HA Constructs with Modified Immunodominant Antigenic Site in the Globular Head Domain

| List No. | Construct Name | Construct Description | SEQ ID No. |
|---|---|---|---|
|  | H1MCS-AS[a] | GP67ss-H1MCS-AS-TEV-foldon-10His[b] |  |
| 8 | H1H5cs-CR8020Ca | GP67ss-H1H5cs-CR8020Ca-TEV-foldon-10His | SEQ ID NO: 24 |
| 9 | H1TEV2-CR8020Ca | GP67ss-H1TEV2-CR8020Ca-TEV-foldon-10His | SEQ ID NO: 29 |
| 10 | H1TEV2-CR8020Sa3 | GP67ss-H1TEV2-CR8020Sa3-TEV-foldon-10His | SEQ ID NO: 31 |
| 11 | H1TEV2-CR8020Sa4 | GP67ss-H1TEV2-CR8020Sa4-TEV-foldon-10His | SEQ ID NO: 33 |
| 12 | H1TEV2-I1C9Ca1 | GP67ss-H1TEV2-I1C9Ca1-TEV-foldon-10His | SEQ ID NO: 35 |
| 13 | H1TEV2-I1C9Ca2 | GP67ss-H1TEV2-I1C9Ca2-TEV-foldon-10His | SEQ ID NO: 38 |
| 14 | H1TEV2-I1C9Sa3 | GP67ss-H1TEV2-I1C9Sa3-TEV-foldon-10His | SEQ ID NO: 40 |
| 15 | H1TEV2-I1C9Sa4 | GP67ss-H1TEV2-I1C9Sa4-TEV-foldon-10His | SEQ ID NO: 42 |
| 16 | H1H5cs-I1C9Sb | GP67ss-H1H5cs-I1C9Sb-TEV-foldon-10His | SEQ ID NO: 44 |
| 17 | H1H5cs-I1C9Ca | GP67ss-H1H5cs-I1C9Ca-TEV-foldon-10His | SEQ ID NO: 46 |
| 18 | H1H5cs-FI65ab | GP67ss-H1H5cs-FI6Sab-TEV-foldon-10His | SEQ ID NO: 48 |
| 19 | H1WT-FI6Sab | GP67ss-H1WT-FI6Sab-TEV-foldon-10His | SEQ ID NO: 52 |
| 20 | H1TEV1-FI6Sa | GP67ss-H1TEV1-FI6Sa-TEV-foldon-10His | SEQ ID NO: 54 |
| 21 | H1H5cs-M2eCa | GP67ss-H1H5cs-M2eCa2-TEV-foldon-10His | SEQ ID NO: 56 |
| 22 | H1H5cs-M2eSb | GP67ss-H1H5cs-M2eSb-TEV-foldon-10His | SEQ ID NO: 59 |
| 23 | H1TEV2-M2eCa | GP67ss-H1TEV2-M2eCa2-TEV-foldon-10His | SEQ ID NO: 61 |

[a]Constructs name is based on the maturation cleavage site and antigenic site modification. H1 denotes H1 HA. MCS denotes a maturation cleavage site. AS denotes an altered immunodominant antigenic site in the globular head domain of H1 HA with a heterologous epitope. Each AS is indicated by the heterologous epitope and the H1 HA immunodominant antigenic site where the heterologous epitope is placed.
[b]Constructs are described by their sequence features. GP67ss denotes GP67 signal sequence. TEV-foldon-10His denotes the TEV cleavage site, foldon sequence, and 10xHis-tag at the C-terminus of the constructs. Schematic drawing of constructs are shown in FIG. 4A-4B.

The positions of these modifications are illustrated in FIG. 5.

The composite CR8020 epitope peptide of 13 amino acid residues replaced a surface loop of 12 residues EIAIR-PKVRDQE around the antigenic site Ca2. The ClaI-NsiI fragment with composite CR8020 epitope peptide substitution was synthesized and subcloned between ClaI and NsiI sites of H1H5cs to generate a HA construct denoted as H1H5cs-CR8020Ca (SEQ ID NO:24). To make H1TEV2-CR8020Ca (SEQ ID NO:29), the ClaI-NsiI fragment of H1H5cs-CR8020Ca was isolated and subcloned between ClaI and NsiI sites of H1TEV2.

The construct H1TEV2-CR8020Sa3 (SEQ ID NO:31) has the composite CR8020 epitope peptide replacing residues KKGNS of one of the Sa sites, which corresponds to the Site B loop of H3 HA on top of the globular head domain. The ClaI-NsiI fragment with the CR8020 modification was synthesized and subcloned between ClaI and NsiI sites of H1TEV2 to generate a HA construct denoted as H1TEV2-CR8020Sa3.

The construct H1TEV2-CR8020Sa4 (SEQ ID NO:33) has the composite CR8020 epitope peptide replacing a helical structure of residues KTSS near one of the Sa sites. This position is on the side of the globular head domain of HA trimer and away from the receptor binding site. Such a modification is unlikely to change the receptor binding. The ClaI-NsiI fragment with the CR8020 modification was synthesized and subcloned between ClaI and NsiI sites of H1TEV2 to generate a HA construct denoted as H1TEV2-CR8020Sa4.

Models of HA monomer of constructs CR8020Sa4 and CR8020Ca are shown in FIGS. 6A-6B. Each HA monomer has a composite CR8020 epitope peptide in the globular head domain and the native CR8020 epitope in the stem domain.

Several HA constructs with I1C9 epitope peptide of GIFGAIAGFIEG (SEQ ID NO:36) were made. One construct H1TEV2-I1C9Ca1 (SEQ ID NO:35) has I1C9 peptide replacing RPKVRDQE at residues 217 to 224 around Ca2 site. Another construct H1H5cs-I1C9Ca (SEQ ID NO:46) has I1C9 peptide replacing a longer peptide EIAIR-PKVRDQE at residues 213 to 224 of Ca2. Other constructs have I1C9 peptide individually replacing a Ca2 site, HAGAKS, that corresponds to the Site A of H3 HA, an Sa site KKGNS, and an Sa site KTSS. Each of the ClaI-NsiI fragments with the changes was synthesized and subcloned between ClaI and NsiI sites of H1TEV2 to generate a HA construct denoted as H1TEV2-I1C9Ca1 (SEQ ID NO:35), H1TEV2-I1C9Ca2 (SEQ ID NO:38), H1TEV2-1C9Sa3 (SEQ ID NO:40), and H1TEV2-I1C9Sa4 (SEQ ID NO:42), respectively. The ClaI-NsiI fragment with the change of I1C9Ca was synthesized and subcloned between ClaI and NsiI sites of H1H5cs to generate a HA construct H1H5cs-I1C9Ca. The I1C9 peptide also replaced residues TSADQQSLYQNA of Sb site of H1H5cs construct as H1H5cs-I1C9Sb (SEQ ID NO:44) by the same method. The Sb site corresponds to the Site B helix of H3 HA.

The ClaI-NsiI fragment was gene synthesized with the FI6 epitope peptide RKKRGLFGAIAGFIE (SEQ ID NO:49) placed at the Sa site and the coiled-coil FI6 epitope peptide KESTQKAIDGVTNKVNS (SEQ ID NO:50) placed at the Sb site. This ClaI-NsiI fragment with FI6 substitutions was subcloned between ClaI and NsiI sites of H1H5cs and H1WT, resulting constructs H1H5cs-FI6Sab (SEQ ID NO:48) and H1WT-FI6Sab (SEQ ID NO:52), respectively. Another ClaI-NsiI fragment was gene synthesized with the FI6 epitope peptide RKKRGLFGAIAGFIE (SEQ ID NO:49) placed at the Sa site. This fragment replaced the ClaI-NsiI fragment of H1TEV1 to generate construct H1TEV1-FI6Sa (SEQ ID NO:54).

EXAMPLE 4

Design and Construction of H1 HA Constructs with M2e Peptide at Antigenic Sites in Globular Head Domain In this example, again, the nucleotide sequence of ClaI-NsiI fragment was replaced by nucleotide sequences wherein a portion of the Ca2 site or of the Sb site was replaced by the nucleotide sequence encoding the M2e peptide. The constructs with M2e peptides are listed in Table 2. The positions of these modifications are illustrated in FIG. 5.

Gene synthesis generated ClaI-NsiI fragments with M2e peptide (SEQ ID NO:57) replacing EIAIRPKVRDQE at the Ca2 site or replacing helix of residues TSADQQSLYQNA of Sb site. HA constructs with M2e peptide were first made in H1H5cs, in which the ClaI-NsiI fragment of H1H5cs was replaced with individual ClaI-NsiI fragment containing M2e peptide, resulting constructs H1H5cs-M2eCa (SEQ ID NO:56) and H1H5cs-M2eSb (SEQ ID NO:59), respectively. To transfer the ClaI-NsiI fragment of H1H5cs-M2eCa to H1TEV2 construct, the ClaI-NsiI fragment of H1H5cs-M2eCa was isolated and subcloned between ClaI and NsiI sites of H1TEV2, resulting a construct named H1TEV2-M2eCa (SEQ ID NO:61).

EXAMPLE 5

Generation of Recombinant Baculoviruses Using Bac-to-Bac Baculovirus Expression Systems This example describes techniques for preparing insect cells comprising the expression systems contained in the constructs prepared in Examples 1-4.

Recombinant baculoviruses were generated from the pFastBacbased transfer vectors of the constructs following the manufacturer's instruction (Bac-to-Bac Baculovirus Expression Systems, Life Technology, Carlsbad, Calif., USA). Briefly, transfer vectors were transformed to *E. coli* DH10Bac chemically competent cells. White colonies with recombinant bacmids were selected on plates with Blue-gal. Bacmid DNA was isolated by standard alkaline lysis miniprep method following the manufacturer's instruction. Recombinant bacmids were identified by PCR using the M13 Forward (−40) primer (GTTTTCCCAGTCACGAC) and M13 Reverse primer (CAGGAAACAGCTATGAC). Recombinant bacmids gave a PCR product of about 4 kb.

SF9 insect cells attached to 12-well plates were transfected with the recombinant bacmids using Cellfectin® Reagent, other commercially available transfection reagents, or polyethylenimine (PEI). After 4-7 days post transfection or when the SF9 cells enlarged due to virus infection, the cell culture media were harvested as P0 viral stocks. Each P0 viral stock was used to infect 50 ml of SF9 cells at a density of $2\times10^6$ cells/ml in shaker flasks to amplify the viruses. The cultures were monitored using Cedex Cell Counter (Roche Diagnostics Corporation, Indianapolis, Ind., USA). The harvest time was determined by the average viable cell size and cell viability. When the average viable cell sizes were 4-7 μm larger than uninfected cells and viabilities were in the range of 50-70% in 4-5 days post infection, cells were removed by centrifugation and cell culture supernatants were collected and stored at 4° C. in the dark as P1 viral stocks. Sometimes the viral stocks were filtered through 0.2 μm sterile filter to maintain sterility.

To further amplify viral stocks, 500 ml of SF9 cells at a density of $2\times10^6$ cells/ml were infected with 250 μl P1 viral stock. The cultures were monitored using Cedex Cell Counter. When the average viable cell sizes were 4-7 μm larger than uninfected cells and viabilities were in the range of 50-70% in 4-5 days post infection, cells were removed by centrifugation and cell culture supernatants were collected and stored at 4° C. in the dark as P2 viral stocks. Sometimes the viral stocks were filtered through 0.2 μm sterile filter to maintain sterility.

EXAMPLE 6

Expression of Recombinant HA Proteins

This example demonstrates expression in insect cells of the various constructs described in Examples 1-4. Depending on the specific construct, various levels of target protein expression were obtained.

To detect the expression of a recombinant HA, cell culture media of SF9 cells that were infected with the recombinant baculovirus stocks, usually the P1 or P2 viral stocks as described in Example 5, were collected and incubated with Ni-NTA resins (Qiagen, Germantown, Md. USA) for affinity capture through the 10×His-tag of the recombinant HA. After washing the Ni-NTA resin with phosphate buffered saline (1×PBS), the Ni-NTA resins were boiled with gel loading buffer in the presence or absence of a reducing agent for analysis by SDS-PAGE or Western blot using anti-His antibodies. A protein band around 63 kDa on a Coomassie® stained gel or anti-His Western blot indicates the expression of secreted recombinant HA full-length protein.

As shown in FIGS. 7A-7E and FIG. 8, the expression of H1 HA protein of the parental construct H1WT was detected as expected. HA proteins with altered maturation cleavage site of polybasic residues, H1H5cs, H1R5cs, and H1IR5cs, expressed to the same level as H1WT. H1TEV1, with the entire H1 HA maturation cleavage site replaced by the TEV cleavage site, expressed much less than H1WT. By keeping more native residues at the maturation cleavage site, H1TEV2 and H1TEV3 expressed very well comparing to H1WT (FIGS. 7A-E and FIG. 8). Not all substitutions expressed to the same level. By adjusting the location of TEV cleavage site in the constructs, expression level to that of the wild type HA was achieved.

Also shown in FIGS. 7A-E and FIG. 8, placements of the same immunosubdominant bNAb epitope at different immunodominant antigenic sites resulted in different expression levels. Constructs of composite CR8020 epitope peptide at either Sa site (H1TEV2-CR8020Sa4) or at Ca2 site (H1H5cs-CR8020Ca) expressed to the same level as the wild type HA, whereas the H1TEV2-CR8020Sa3 construct did not express well. Thus the exact positions of the heterologous epitope placement could be important for the expression of the resulting HA. The nature of the immunosubdominant bNAb epitopes may impact the expression levels of the resulting HA proteins as well.

Individual placement of I1C9 epitope at several antigenic sites also showed different levels of expression of the resulting HA proteins (FIGS. 7A-E and FIG. 8). Construct H1H5cs-I1C9Ca showed higher expression than construct H1TEV2-I1C9Ca1. The peptide sequences in the antigenic sites replaced by I1C9 epitope peptide in these two constructs are slightly different. Similar to those constructs with TEV cleavage site as MCS, the location of substitution affects the expression level.

Constructs with M2e peptide at Ca2 sites, namely H1H5cs-M2eCa and H1TEV2-M2eCa, gave expression as good as H1WT, regardless of the maturation cleavage sites (FIGS. 7A-E and FIG. 8). However the construct H1H5cs-M2eSb with the M2e peptide at the Sb site did not express well. The Sb site is in a helical structure which may be required for proper folding of HA.

The successful expression of many of the H1 HA constructs demonstrated that the immunodominant antigenic sites of HA globular head domain can be replaced by immunosubdominant bNAb epitopes from the stem domain or by an M2e peptide from anther protein not related to HA. These results revealed the plasticity of the globular head domain and validated the feasibility of making a functional HA to present heterologous epitopes in its globular head domain. Together, Examples 1-6 demonstrated methods to construct HAs with heterologous epitopes and/or altered MCS and to select the modified HAs with good expression.

EXAMPLE 7

Purification of Recombinant HA Proteins

This example demonstrates the purification of the various constructs described in Examples 1-4.

Figure 8:
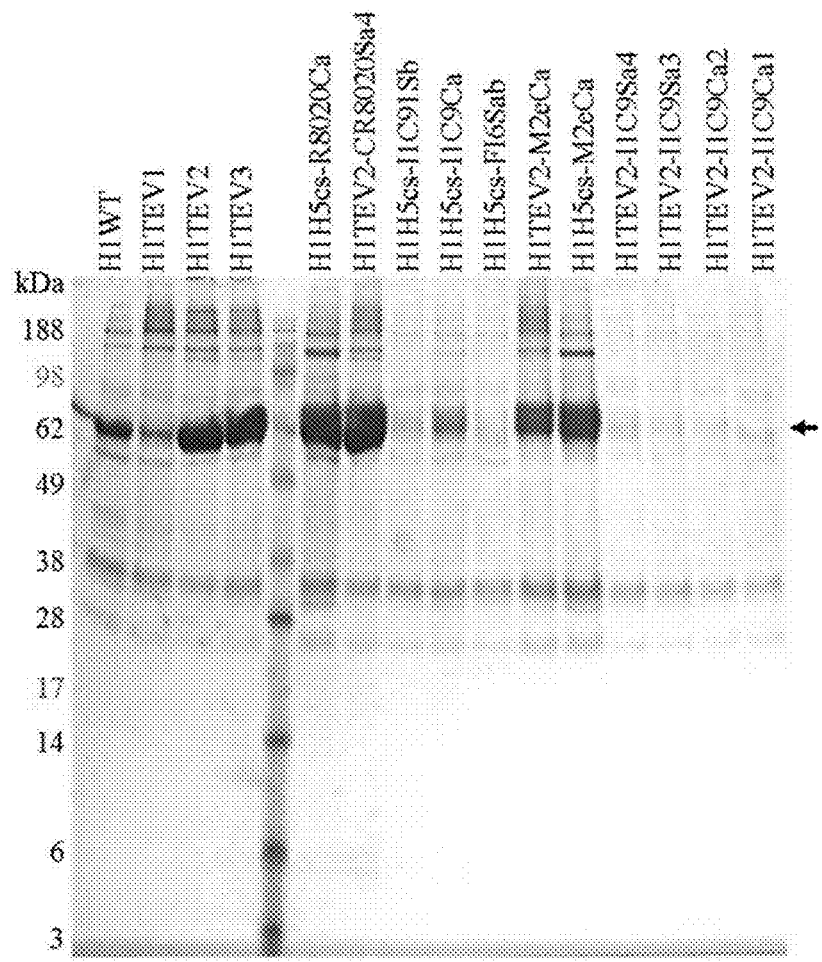
FIG. 8 shows the purified HA constructs used in this invention. Cell culture medium of SF9 cells infected with recombinant baculovirus of the indicated construct was harvested and captured by Ni-NTA resin (Ni pull-down). The Ni-NTA resin was washed with 1×PBS. Bound proteins were eluted with imidazole and analyzed by SDS-PAGE with Coomassie® staining. The arrow indicates the full-length HA0.

In shaker flasks, 50 ml to 1 L of SF9 cells at a density of $2 \times 10^6$ cells/ml were infected with a baculovirus stock at a volumetric ratio of 1-4 ml P1 or P2 viral stock to 1 liter of cells. The culture was monitored using Cedex Cell Counter. The harvest time was determined by the average viable cell size and cell viability. When the average viable cell sizes were 4-7 µm larger than uninfected cells and viabilities were about 80% in 2 to 3 days post infection, cells were removed by centrifugation and conditioned cell culture media were collected and stored at 4° C. The conditioned cell culture media were incubated with Ni-NTA resins with rocking on a rotisserie platform for 2-4 hours at 4° C. The Ni-NTA resins were collected by centrifugation and washed with 1×PBS. The washed Ni-NTA resins were packed into a gravity flow column and further washed with 1×PBS supplemented with 50 mM imidazole. The Ni-NTA resins were then eluted with 400 mM imidazole in 1×PBS by gravity flow. The eluted HA proteins were buffer exchanged to 1×PBS and concentrated by ultrafiltration. The purified HA proteins were analyzed by SDS-PAGE as shown in FIG. 8.

APPENDIX

Description of Influenza Viruses, Types and Hosts

Influenza viruses consist of three genera of Orthomyxoviridae family of viruses, which are influenzavirus A, B and C. Each genus has only a single species of viruses, namely influenza A, B, and C virus, respectively. Influenza A, B, and C viruses are also called type A, B, and C influenza viruses, respectively. Influenza viruses are enveloped negative-sense single stranded RNA viruses. The viral genome is encoded in separate RNA segments. Influenza A and B viruses each has 8 RNA segments that encode 10 proteins. Influenza C viruses each has 7 RNA segments that encode 9 proteins. The 10 characterized proteins of influenza A viruses are PB2, PB1, and PA polymerases, hemagglutinin (HA), nucleoprotein (NP), neuraminidase (NA), matrix proteins M1 and M2, nonstructural proteins NS1 and NS2 (Webster, R. G., et al., *Microbiol Rev* (1992) 56:152-179). Influenza C viruses have a hemagglutinin-esterase-fusion (HEF) protein that combines the functions of HA and NA (Herrler, G., et al., *J. Gen Virol* (1988) 69:839-846). Classification of Influenza A, B and C viruses is based on antigenic differences in their NP and matrix proteins.

Influenza A viruses are small particles of 80-120 nm in diameter that consist of a host-derived lipid bilayer envelope studded with the virus-encoded membrane proteins HA, NA, and M2, an inner shell made of M1 matrix protein, and the nucleocapsids of the viral genome of individual RNA segments at the center (Webster, R. G., et al., *Microbiol Rev* (1992) 56:152-179). The RNA segments are loosely encapsidated by multiple NP molecules. Complexes of the three viral polymerase proteins (PB1, PB2 and PA) are situated at the ends of the nucleocapsids. All RNA segments are necessary for producing an infectious virus particle.

RNA segment 1, the slowest-migrating RNA species by gel electrophoresis, encodes PB2 RNA polymerase. RNA segment 2 encodes PB1 RNA polymerase, plus two other transcripts for PB1-N40 and PB1-F2 proteins by using different reading frames from the same RNA sequence. PB1-N40 and PB1-F2 proteins induce host cell apoptosis. RNA segment 3 encodes PA RNA polymerase that forms the RNA-dependent RNA polymerase complex with PB1 and PB2. RNA segment 4 encodes HA, the major surface antigen of the influenza virion. Each virion has about 500 HA molecules that appears as uniformly distributed spikes on the virion surface (Ruigrok, R. W. H., et al., *J. Gen Virol* (1984) 65:799-902; Murti, K. G., and Webster, R. G., *Virol* (1986) 149:36-43). Binding to the host receptors, HA determines the host range. RNA segment 5 encodes NP nucleoprotein. NP encapsidates viral RNA and is transported to host cell nucleus. NP is abundantly synthesized in infected cells and is the second most abundant protein in the influenza virus virion. It is a major target of the host cytotoxic T-cell immune response. RNA segment 6 encodes neuraminidase (NA), the second major surface antigen of the influenza virus virion. NA is an enzyme that cleaves terminal sialic acid from glycoproteins or glycolipids to release virus particles from host cell receptors. Its function is required for virus spread. Each virion has about 100 NA molecules on its surface. NA forms a tetramer and is located in discrete patches on the virion envelope (Murti, K. G., and Webster, R. G., *Virol* (1986) 149:36-43). RNA segment 7 is bicistronic and encodes both matrix proteins, M1 and M2. M1 forms a shell surrounding the virion nucleocapsids underneath the virion envelope and is the most abundant protein in the influenza virus virion. M2 is made from a different splicing form of the same transcript of M1. M2 is an integral membrane protein and functions as a proton channel to control the pH of the Golgi network during the production of influenza virus in host cells. M2 can be partially replaced by an alternative splicing variant M42. About 3000 matrix protein molecules are needed to make one virion. RNA segment 8 encodes the two nonstructural proteins NS1 and NS2 for virus replication. NS2 is from a different reading frame from NS1. Both proteins are abundant in the infected cell but are not incorporated into progeny virions.

Among the three genera of influenza viruses, influenza A viruses are the most virulent human pathogens and cause the most severe disease in human. Influenza A viruses are classified into subtypes based on the antigenic properties of their surface glycoproteins HA and NA. A total of 18 HA subtypes, named H1 to H18, and 10 NA subtypes, named N1 to N10, have been identified (Tong, S., et al., *PLoS Pathogens* (2013) 9:e1003657). The common nomenclature for influenza A subtypes is derived from different combinations of HA subtype and NA subtype, such as H1N1, H3N2, and H7N9 (*Bull World Health Organ* (1980) 58: 585-591). Waterfowl is the natural reservoir of subtypes H1 to H16 and N1 to N9. Subtypes H17N10 and H18N10 were recently discovered in American fruit bats. In nature, the segmented genome of influenza A viruses allows re-assortment of RNA segments when a host is co-infected with two subtypes of influenza A viruses. RNA segments from two different subtypes can be packaged in a single virion to produce a new subtype. Of these many subtypes of influenza A viruses, only H1N1, H2N2, and H3N2 have developed the capacity for efficient transmission in humans. These three subtypes are the prevalent virus subtypes of the so called seasonal flu viruses. Human population is therefore immunologically naïve to many influenza A subtypes. Occasionally other subtypes influenza A viruses cross species and infect humans to cause pandemic outbreaks with high fatality.

Based on their phylogenetic relationship, influenza A HA subtypes are clustered into two distinct groups. Group 1 includes 10 of the 16 subtypes: H1, H2, H5, H6, H8, H9, H11, H12, H13, and H16. Group 2 accounts for the remaining 6 subtypes: H3, H4, H7, H10, H14, and H15.

Influenza B viruses are antigenically distinct from influenza A viruses. Influenza B viruses co-circulate with type A viruses and cause epidemics in human. Influenza B viruses are stably adapted to humans without a known animal reservoir. Unlike the vast genetic variations of HA of influenza A viruses, only one serotype of HA is reported in influenza B viruses, although three lineages are defined by phylogenetic relationships of the HA genes. Influenza B viruses do not appear to recombine with influenza A viruses as there has been no report of re-assortment of RNA segments between influenza A and influenza B viruses.

Both influenza A and B viruses use terminal sialic acid on host cell surface as the cellular receptor. HAs of both types of viruses share the same structural features and bind to the sialic acid receptor for entry to host cells.

Subtypes of influenza A and influenza B viruses are further classified into strains. There are many different strains of influenza A and influenza B viruses. Each flu season is dominated by a few strains of influenza A and B viruses that usually differ genetically from the strains of the previous flu season. Viruses of one strain isolated at different geographic locations or time of a flu season, known as isolates, often have genetic changes.

Infection of influenza C viruses is generally asymptomatic or causes mild illness involving mostly children or young adults. Influenza C viruses are associated with sporadic cases and minor localized outbreaks. Influenza C viruses pose much less of a disease burden than influenza A and B viruses. Large proportion of human population shows seroconversion, which suggests wide circulation of influenza C viruses in human population. Influenza C viruses have also been isolated from animals. The hemagglutinin-esterase-fusion (HEF) protein of influenza C virus combines the function of HA and NA of the influenza A and B viruses. Unlike HA of influenza A and B viruses, HEF of influenza C virus uses terminal 9-O-acetyl-N-acetylneuraminic acid (9-O—Ac-NeuAc) as the cellular receptor (Herrler, G., et al., *EMBO J*. (1985) 4:1503-1506).

Description of Virus Infection Process and Life Cycle

Influenza viruses are spread from person to person through respiratory droplets or fomites (any object or substance capable of carrying infectious organisms). The viruses infect the epithelial cells of the respiratory tract. After binding to cell surface receptors, the attached virion is endocytosed by the host cell to the endosomes where the low pH triggers a conformational change of HA that leads to insertion of its hydrophobic fusion peptide into the vesicular membrane of the host cell and initiate fusion of the viral and vesicular membranes. Fusion releases the contents of the virion into the cytoplasm of the infected cell. The viral nucleocapsids migrate into the host cell nucleus, and their associated polymerase complexes begin primary transcription of mRNA for translation of viral proteins. At the same time, translation of host mRNAs is blocked. Newly synthesized viral RNAs are encapsidated and viral structural proteins are synthesized and transported to the host cell surface, where they integrate into the host cell membrane. Influenza viruses bud from the apical surface of polarized epithelial cells, such as bronchial epithelial cells, into lumen of lungs and are therefore usually pneumotropic (Roth, M. G., et al., *PNAS* (1979) 76: 6430-6434; Nayak, D. P., et al., *Virus Res* (2009) 143:147-161). Transmission of influenza virus between pigs and humans has been demonstrated. After an individual becomes infected, the immune system develops antibodies against the influenza virus. This is the body's main source of protection.

---

The invention claimed is:

1. A modified hemagglutinin (HA) protein of influenza virus comprising a globular head domain and a stem domain, wherein at least one immunodominant region of the globular head domain of said HA protein contains an influenza stem epitope, wherein said influenza stem epitope comprises one or more stem peptides of the same HA and is recognized by a broadly neutralizing antibody (bnAb) against influenza viruses.

2. The modified HA protein of claim 1, wherein the at least one immunodominant region of the globular head domain contains said influenza stem epitope by insertion into said domain, or contains said stem epitope by replacing said domain with said influenza stem epitope.

3. The modified HA protein of claim 1, wherein the at least one immunodominant region of the globular head domain is at least two, at least three, at least four, or at least five immunodominant regions.

4. The modified HA protein of claim 3, wherein the one or more stem epitopes contained in the at least two, at least three, at least four, or at least five immunodominant regions of the globular head domain are distinct.

5. The modified HA protein of claim 3, wherein the one or more stem epitopes contained in the at least two, at least three, at least four, or at least five immunodominant regions of the globular head domain are identical.

6. The modified HA protein of claim 1, wherein said HA protein is contained in a live or attenuated virus or in a virus-like particle (VLP).

7. A polynucleotide encoding the modified HA protein of claim 1.

8. A recombinant influenza virus, wherein the recombinant virus comprises the polynucleotide of claim 7, such that the modified HA protein is expressed on the surface of the virus.

9. A recombinant host cell comprising the polynucleotide of claim 7.

10. An immunogenic composition comprising the modified HA protein of claim 1.

11. The immunogenic composition of claim 10, wherein the composition comprises a live or attenuated virus or VLP.

12. An immunogenic composition comprising the polynucleotide of claim 7.

13. A method to generate antibodies against influenza viruses, which method comprises administering to a subject the immunogenic composition of claim 10.

14. A method to generate antibodies against influenza viruses, which method comprises administering to a subject the immunogenic composition of claim 12.

* * * * *